United States Patent
Stoop et al.

(10) Patent No.: US 7,476,778 B2
(45) Date of Patent: Jan. 13, 2009

(54) PLANT GALACTINOL SYNTHASE HOMOLOGS

(75) Inventors: Johan M. Stoop, Wilmington, DE (US); Perry G. Caimi, Kennett Square, PA (US)

(73) Assignee: E.I. Du Pont, Wilmington, DE (US)

( * ) Notice: Subject to any disclaimer, the term of this patent is extended or adjusted under 35 U.S.C. 154(b) by 0 days.

(21) Appl. No.: 11/928,675

(22) Filed: Oct. 30, 2007

(65) Prior Publication Data

US 2008/0172758 A1 Jul. 17, 2008

Related U.S. Application Data

(62) Division of application No. 11/149,403, filed on Jun. 8, 2005, now Pat. No. 7,294,756.

(60) Provisional application No. 60/581,851, filed on Jun. 22, 2004.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .................. 800/278; 435/320.1; 435/419; 435/468; 536/23.2; 800/284; 800/295

(58) Field of Classification Search .................. None
See application file for complete search history.

(56) References Cited

U.S. PATENT DOCUMENTS

| | | | |
|---|---|---|---|
| 5,648,210 | A | 7/1997 | Kerr et al. |
| 5,773,699 | A | 6/1998 | Kerr et al. |
| 2004/0038357 | A1 | 2/2004 | Obendorf et al. |

FOREIGN PATENT DOCUMENTS

| | | | |
|---|---|---|---|
| WO | WO 93/02196 | | 2/1993 |
| WO | WO 98/50553 | | 11/1998 |
| WO | WO 01/77306 A2 | | 10/2001 |
| WO | WO 0177306-A 3 | * | 10/2001 |
| WO | WO 02/00904 | | 1/2002 |

OTHER PUBLICATIONS

U.S. Appl. No. 60/578,404, filed Jun. 9, 2004, Biran McGonigle.
U.S. Appl. No. 60/625,835, filed Nov. 8, 2004, Zhan-Bin Liu et al.
P. M. Dey, D-Galactose-Containing Oligosaccharides, Biochemistry of Storage—Carbohydrates in Green Plants, Chapter 2, Academic Press, p. 53-129, 1985.
Richard Gitzelmann et al., The Handling of Soya Alpha-Galactosides by a Normal and a Galactosemic Child, Pediatrics, vol. 36(2):231-235, Aug. 1965.
H. Rutloff et al., Die intestinal-enzymatische Spaltung von Galakto-Oligosacchariden in Darm von Tier und Mensch mit besonderer Berucksichtigung von *Lactobacillus bifidus*, Die Nahrung, vol. 11(1):39-46, 1967.
Edwin L. Murphy et al., Carbon Dioxide Egestion in Human Flatus, J. Agr. Food Chem., vol. 20(4);813-817, 1972.
E. Cristofaro et al., Involvement of the Raffinose Family of Oligosaccharides in Flatulence, Sugars in Nutrition, Chapter 20, Academic Press, p. 313-335, 1974.
N. R. Reddy et al., Flatulence in Rats Following Ingestion of Cooked and Germinated Black Gram and a Fermented Product of Black Gram and Rice Blend, Journal of Food Science, vol. 45:1161-1164, 1980.
Levis W. Handley et al., Relationship between Galactinol Synthase Activity and Sugar Composition of Leaves and Seeds of Several Crop Species, J. Amer. Soc. Hort. Sci., vol,. 108(4):600-605, 1983.
David M. Saravitz et al., Galactinol Synthase Activity and Soluble Sugars in Developing Seeds of Four Soybean Genotypes, Plant Phys., vol. 83:185-189, 1987.
Norbert Sprenger et al., Allocation of raffinose family oligosaccharides to transport and storage pools in Ajuga reptans: the roles of two distinct galactinol synthases, The Plant Journal, vol. 21(3):249-258, 2000.
National Center for Biotechnology Information General Identifier No. 5541885, Apr. 15, 2005, R. G. Jones, Carbon Partitioning in Developing Pea Embryos.
National Center for Biotechnology Information General Identifier No. 15223567, Feb. 23, 2005, Accession No. NP 176053.
National Center for Biotechnology Information General Identifier No. 32345694, Mar. 9, 2005, R. L. Obendorf et al., Soybean galactinol synthase forms fagopyritol B1 but not galactopinitols: Substrate feeding of isolated embryos and heterologous expression.
William D. Hitz et al., Biochemical and Molecular Characterization of a Mutation That Confers a Decreased Raffinosaccharide and Phytic Acid Phenotyye on Soybean Seeds, Plant Physiology, vol. 128:650-660,2002.
R.G. Jones et. al., Putative Galactional Synthase, 1999, XP002349102, Accession No. Q9XGG4.
T. Ueda et. al., A Multifunctional Galactional Synthase Catalyzes the Synthesis of Fagopyritol A1 and Fagopyritol B1 in Buckwheat Seed, Plant Sci., Galactional Synthase, 2005, pp. 681-690, vol. 168, XP002349103, Accession #, Q7XZ08.
Ralph L. Obendorf et. al., Soybean Galactinol Synthase Form Fagopyritol B1 but not Galactopinitols: Substrate Feeding of Isolated Embryos and Heterologous Expression, Seed Science Research, 2004, pp. 321-333, vol. 14.

* cited by examiner

*Primary Examiner*—Anne Marie Grunberg
*Assistant Examiner*—Brendan O. Baggot
(74) *Attorney, Agent, or Firm*—Lori Beandell

(57) ABSTRACT

Isolated nucleic acid fragments encoding galactinol synthase are disclosed. Recombinant DNA construct(s) for use in altering expression of endogenous genes encoding galactinol synthase are also disclosed.

10 Claims, 22 Drawing Sheets

SEQ ID NO:2 MAPELVPTVVKSSAAFTKPA--TLPRRAYVTFLAGNDYVKGVVGLAKGLRKVKTAYPLV
SEQ ID NO:4 APNITTVVANATTEQLPKAHGGSSGRAFVTFLAGNDYVKGVVGLAKGLRKAKSMYPLV
SEQ ID NO:6 MAPNITTV----TDAQAKAA--GGRGRAYVTFLAGNDYVKGVVGLAKGLRKVKSMYPLV
SEQ ID NO:7 MAPEIVQTSTKPVTGFTKL-----KRAYVTFLAGNGDYVKGVIGLAKGLRKVKTAYPLV
SEQ ID NO:8 MAPEINTKLTVPVHSAT-----GGEKRAYVTFLAGTGDYVKGVVGLAKGLRKAKSKYPLV
SEQ ID NO:9 MAPNITTVKTTITDAQAKVA--TDHGRAYVTFLAGNGDYVKGVVGLAKGLRKVKSMYPLV
            *********  *  *    **         ****** ** *  **
            ***

SEQ ID NO:2 VAVLPDVPEEHRKILESQGCIVREIEPVYPPENQTQFAMAYYVINYSKLRIWEFVEYSKM
SEQ ID NO:4 VAVLPDVPEEHRAILKSQGCIVREIEPVYPPKNQTQFAMAYYVINYSKLRIWEFVEYQKM
SEQ ID NO:6 VAVLPDVPEHHRNILTSQGCIVREIEPVYPPKNQTQFAMAYYVINYSKLRIWEFVEFSKM
SEQ ID NO:7 VAVLPDVPEEHREMLESQGCIVREIQPVYPPENQTQFAMAYYVINYSKLRIWEFVEYSKM
SEQ ID NO:8 VAVLPDVPEDHRKQLVDQGCVVKEIEPVYPPENQTEFAMAYYVINYSKLRIWEFVEYNKM
SEQ ID NO:9 VAVLPDVPQDHRNILTSQGCIVREIEPVYPPENQTQFAMAYYVINYSKLRIWEFVEYSKM
            ******  *  *   ******* *******************
            **

FIG. 1A

SEQ ID NO:2 IYLDGDIEVYYENIDHLFDLPDGNFYAVMDCFCEKTWSHTPQYKVGYCQQCPEKVRWP-TE
SEQ ID NO:4 IYLDGDIQVFGNIDHLFDLPNNYFYAVMDCFCEKTWSHTPQFQIGYCQQCPDKVQWP-SH
SEQ ID NO:6 IYLDGDIQVFDNIDHLFDLPDNYFYAVMDCFCFEPTWGHTLQYQIGYCQQCPHKVQWP-TH
SEQ ID NO:7 IYLDGDIQVYYENIDHLFDLPDGYFYAVMDCFCEKTWSHTPQYKIGYCQQCPEKVQWP-KE
SEQ ID NO:8 YLDGDIQVFDNIDHLFDLPNGQFYAVMDCFCEKTWSHSPQYKIGYCQQCPDKVTWPEAK
SEQ ID NO:9 IYLDGDIQVFDNIDHLFDLPDNYFYAVMDCFCEPTWGHTKQYQIGYCQQCPHKVQWP-TH
             ******* * ********* *  *  *******   *   ****** **   *

SEQ ID NO:2 LGQPPSLYFNAGMFVFEPNIATYHDLLKTVQVTTPTSFAEQDFLNMYFKDIYKPIPLNYN
SEQ ID NO:4 FGTKPPLYFNAGMFVYEPNLNTYRHLLQTVQVIKPTSFAEQDFLNMYFKDKYKPIPNVYN
SEQ ID NO:6 FGPKPPLYFNAGMFVYEPNLDTYRDLLQTVQVTKPTSFAEQDFLNMYFKDKYRPIPNVYN
SEQ ID NO:7 MGEPPSLYFNAGMFLFEPSVETYDDLLKTCQVTAPTPFADQDFLNMYFKDIYRPIPLVYN
SEQ ID NO:8 LGPKPPLYFNAGMFVYEPNLSTYHNLLETVKIVPPTLFAEQDFLNMYFKDIYKPIPPVYN
SEQ ID NO:9 FGPKPPLYFNAGMFVYEPNLATYRDLLQTVQVTQPTSFAEQDFLNIYFKDKYRPIPNVYN
  *  ******      *** *     **** *** * **  *

FIG. 1B

SEQ ID NO:2   LVLAMLWRHPENVKLDQVKVVHYCAAGSKPWRYTGKEENMQREDIKMLVKKWWDIYNDAS
SEQ ID NO:4   LVLAMLWRHPENVELDQVQVQVVHYCAAGSKPWRFTGKEENMDREDIKMLMKKWWDIYEDET
SEQ ID NO:6   LVLAMLWRHPENVELEKVKVVHYCAAGSKPWRYTGKEENMEREDIKMLVKKWWDIYEDET
SEQ ID NO:7   LVLAMLWRHPENVELRKVKVVHYCAAGSKPWRYTGKEENMQREDIKMLVQKWLDIYSDSS
SEQ ID NO:8   LVLAMLWRHPENIELDQVKVVHYCAAGAKPWRFTGEEENMDREDIKMLVKKWWDIYNDES
SEQ ID NO:9   LVLAMLWRHPENVELDKVKVVHYCAAGSKPWRYTGKEENMEREDIKMLVKKWWDIYEDET
              ************ *  * ******     ** ****  * ****

SEQ ID NO:2 LDYKPLMNASEAPAADGVDIEQFVQALSEVGHVQYVTAPSAA
SEQ ID NO:4 LDYNN----------NSVNVERFTSVLLDAGGFQFVPAPSAA
SEQ ID NO:6 LDYNN----------PFNVDRFTAALLEVGEVKFVRAPSAA
SEQ ID NO:7 LDYKKNLSGNCETQRNDVE-EPFVQALSEVGRVRYVTAPSAA
SEQ ID NO:8 LDYKNVVIGDSHKKQQTL--QQFIEALSEAGALQYVKAPSAA
SEQ ID NO:9 LDYNN----------PLNVDKFTAALMEVGEVKFVRAPSAA
            ***         *    *   *****

FIG. 1C

PLANT GALACTINOL SYNTHASE HOMOLOGS

This case is a divisional application under 37 CFR § 1.53 (b). Specifically, this application is a divisional of application Ser. No. 11/149,403 filed Jun. 8, 2005, now U.S. Pat. No. 7,294,756, which claims the benefit of Provisional Application No. 60/581,851 filed Jun. 22, 2004, the entire contents of which are hereby incorporated by reference.

FIELD OF THE INVENTION

This invention is in the field of plant molecular biology. More specifically, this invention pertains to isolated polynucleotides comprising nucleic acid fragments encoding galactinol synthase homologs in plants and seeds wherein all or part of such isolated polynucleotides can be used to down-regulate expression of endogenous genes encoding galactinol synthase.

BACKGROUND OF THE INVENTION

Raffinose saccharides are a group of D-galactose-containing oligosaccharide derivatives of sucrose that are widely distributed in plants. Raffinose saccharides are characterized by the general formula: [O-β-D-galactopyranosyl-(1→6)$_n$-α-glucopyranosyl-(1→2)-β-D-fructofuranoside where n=0 through n=4 are known respectively as sucrose, raffinose, stachyose, verbascose, and ajugose. A set of galactosyltransferases is involved in the biosynthesis of raffinose saccharides. Galactinol synthase (EC 2.4.1.123) catalyzes the synthesis of galactinol (O-α-D-gal-actopyranosyl-[1→1]-L-myo-inositol) from UDP-D-Gal and myo-inositol. Raffinose and stachyose are then synthesized by addition of Gal units from galactinol to sucrose and raffinose, respectively. These reversible reactions are mediated by raffinose synthase (EC 2.4.1.82) and stachyose synthase (EC 2.4.1.67). Transfer of a further Gal residue from galactinol to stachyose gives verbascose.

Extensive botanical surveys of the occurrence of raffinose saccharides have been reported in the scientific literature [see Dey (1985) in Biochemistry of Storage Carbohydrates in Green Plants, P. M. Dey and R. A. Dixon, Eds. Academic Press, London, pp. 53-129]. Raffinose saccharides are thought to be second only to sucrose with respect to abundance among the nonstructural carbohydrates in the plant kingdom. In fact, raffinose saccharides may be ubiquitous, at least among higher plants. Raffinose saccharides accumulate in significant quantities in the edible portion of many economically significant crop species. Examples include soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.).

Although abundant in many species, raffinose saccharides are an obstacle to the efficient utilization of some economically important crop species. Raffinose saccharides are not digested directly by animals, primarily because alpha-galactosidase is not present in the intestinal mucosa [Gitzelmann et al. (1965) *Pediatrics* 36:231-236; Rutloff et al. (1967) *Nahrung* 11:39-46]. However, microflora in the lower gut are readily able to ferment the raffinose saccharides resulting in an acidification of the gut and production of carbon dioxide, methane and hydrogen gases [Murphy et al. (1972) *J. Agr. Food. Chem.* 20:813-817; Cristofaro et al. (1974) in Sugars in Nutrition, H. L. Sipple and K. W. McNutt, Eds. Academic Press, New York, Chap. 20, 313-335; Reddy et al. (1980) *J. Food Science* 45:1161-1164]. The resulting flatulence can severely limit the use of leguminous plants in animal, particularly human, diets. It is unfortunate that the presence of raffinose saccharides restricts the use of legumes in human diets because many of these species are otherwise excellent sources of protein and soluble fiber. Varieties of edible beans free of raffinose saccharides would be more valuable for human diets and would more fully use the desirable nutritional qualities of edible leguminous plants.

The biosynthesis of raffinose saccharides has been well characterized [see Dey (1985) in Biochemistry of Storage Carbohydrates in Green Plants, P. M. Dey and R. A. Dixon, Eds. Academic Press, London, pp. 53-129]. The committed reaction of raffinose saccharide biosynthesis involves the synthesis of galactinol from UDP-galactose and myo-inositol. The enzyme that catalyzes this reaction is galactinol synthase (inositol 1-alpha-galactosyltransferase; EC 2.4.1.123). Synthesis of raffinose and higher homologues in the raffinose saccharide family from sucrose is thought to be catalyzed by distinct galactosyltransferases (for example, raffinose synthase and stachyose synthase). Studies in many species suggest that galactinol synthase is the key enzyme controlling the flux of reduced carbon into the biosynthesis of raffinose saccharides [Handley et al. (1983) *J. Amer. Soc. Hort. Sci.* 108: 600-605; Saravitz, et al. (1987) *Plant Physiol.* 83:185-189].

Related galactinol synthase genes already known in the art include sequences disclosed in WO 01/77306 and in U.S. Pat. No. 5,648,210, Kerr et al. (the contents of which are hereby incorporated by reference), and Sprenger and Keller (2000) *Plant J* 21:249-258. Presumably related sequences are also disclosed in WO 98/50553.

There is a great deal of interest in identifying the genes that encode proteins involved in raffinose saccharides in plants. Specifically, the galactinol synthase gene may be used to alter galactinol synthesis and modulate the level of raffinose saccharides in plant cells. Accordingly, the availability of nucleic acid sequences encoding all or a portion of a galactinol synthase would facilitate studies to better understand raffinose synthesis in plants, and provide genetic tools to alter raffinose saccharide synthesis to enhance the nutritional qualities of many edible leguminous plants.

SUMMARY OF THE INVENTION

In a first embodiment, the invention concerns an isolated polynucleotide comprising:
  (a) a nucleotide sequence encoding a polypeptide having galactinol synthase activity, wherein the polypeptide has an amino acid sequence of at least 85% identity, when compared to one of SEQ ID NO: 2 or 4 or 95% identity when compared to one of SEQ ID NO:6, based on the Clustal V method of alignment,
  (b) all or part of the isolated polynucleotide comprising (a) for use in co-suppression or antisense suppression of endogenous nucleic acid sequences encoding polypeptides having galactinol synthase activity, or
  (c) a complement of the nucleotide sequence of (a) or (b), wherein the complement and the nucleotide sequence consist of the same number of nucleotides and are 100% complementary.

In a second embodiment, the instant invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention includes a vector comprising any of the isolated polynucleotides of the present invention.

In a fourth embodiment, the present invention concerns a method for transforming a cell comprising transforming a cell with any of the isolated polynucleotides of the present invention. The cell transformed by this method is also included. Advantageously, the cell is eukaryotic, e.g., a yeast or plant cell, or prokaryotic, e.g., a bacterium.

In a fifth embodiment, the present invention includes a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns an isolated polypeptide having galactinol synthase activity, wherein the polypeptide has an amino acid sequence of at least 85%, 90%, or 95% identity, based on the Clustal V method of alignment, when compared to one of SEQ ID NO: 2 or 4 and wherein the polypeptide has an amino acid sequence of at least 95% identitiy, based on the Clustal V method of alignment, when compared to SEQ ID NO:6.

In a seventh embodiment, the present invention concerns a method for isolating a polypeptide having galactinol synthase activity comprising isolating the polypeptide from a cell or culture medium of the cell, wherein the cell comprises a recombinant DNA construct comprising a polynucleotide of the invention operably linked to at least one regulatory sequence.

In an eighth embodiment, this invention concerns a method for selecting a transformed cell comprising: (a) transforming a host cell with the recombinant DNA construct or an expression cassette of the present invention; and (b) growing the transformed host cell, preferably a plant cell, under conditions that allow expression of the galactinol synthase polynucleotide in an amount sufficient to complement a null mutant in order to provide a positive selection means.

In a ninth embodiment, this invention relates to a method of reducing the raffinose saccharide content of soybean seeds by at least 30%, 40%, 50%, 60%, 70%, 80%, 90%, 95% or 100% or any integer percentage in between 30% to 100%.

In a tenth embodiment, this invention relates to a method of reducing the total stachyose content by at least 36%, 40%, 50%, 60%, 70%, 80%, 90%; 95% or 100% or any integer percentage between 36% to 100%.

In another embodiment, this invention relates to a method of reducing the level of at least one raffinose saccharide in soybean.

BRIEF DESCRIPTION OF THE DRAWINGS AND SEQUENCE LISTING

The invention can be more fully understood from the following detailed description and the accompanying drawings and Sequence Listing, which form a part of this application.

FIG. 1 shows a comparison of the amino acid sequence alignment between the galactinol synthase encoded by the nucleotide sequences derived from soybean clones sdp3c.pk013.c9:fis, srr3c.pk003.h12:fis and srr3c.pk001.i20:fis (SEQ ID NO:2, SEQ ID NO:4 and SEQ ID NO:6, respectively) and the galactinol synthase from *Pisum sativum* (NCBI GenBank Identifier (GI) No. 5541885; SEQ ID NO:7), *Arabidopsis thaliana* (NCBI GenBank Identifier (GI) No. 15223567; SEQ ID NO:8) and *Glycine max* (NCBI GenBank Identifier (GI) No. 32345694; SEQ ID NO:9). Amino acids which are conserved among all sequences are indicated with an asterisk (*) below the conserved residue. The program to maximize alignment of the sequences uses dashes.

Figure 2:
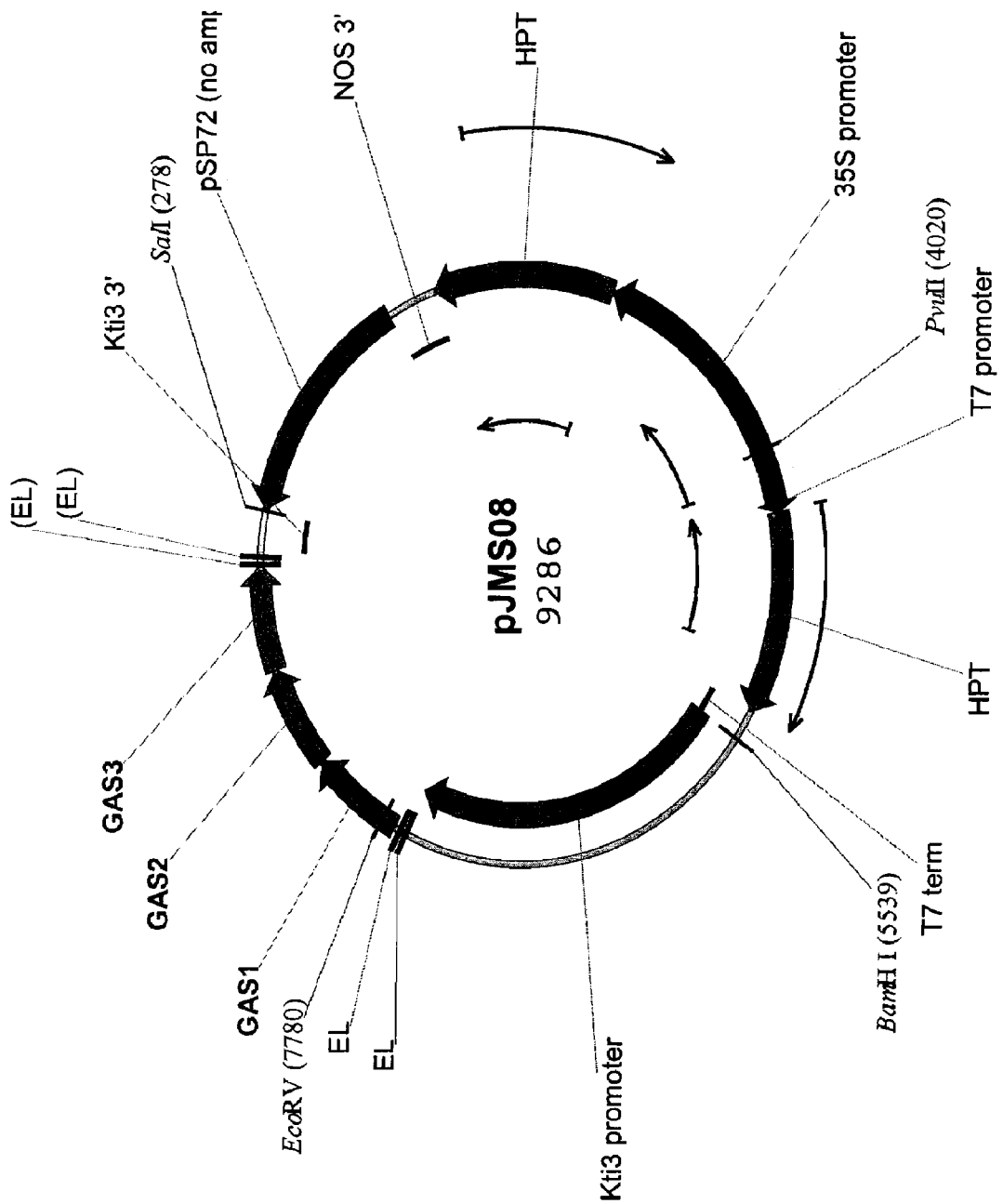
FIG. 2 shows vector pJMS08.

SEQ ID NO:1 is the 1151 bp sequence derived from clone sdp3c.pk013.c9 (FIS) of the soybean nucleotide sequence containing the ORF [nucleotides 71-1090 (Stop)] of the galactinol synthase 3 gene.

SEQ ID NO:2 is the 339 amino acid sequence encoded by the ORF [nucleotides 71-1090 (Stop)] of SEQ ID NO: 1

SEQ ID NO:3 is the 1398 bp sequence derived from clone srr3c.pk003.h12 (FIS) of the soybean nucleotide sequence containing the ORF [nucleotides 94-1089 (Stop)] of the galactinol synthase 4 gene.

SEQ ID NO:4 is the 331 amino acid sequence encoded by the ORF [nucleotides 94-1089 (Stop)] of SEQ ID NO: 3.

SEQ ID NO:5 is the 1417 bp sequence derived from clone srr3c.pk001.i20 (FIS) of the soybean nucleotide sequence containing the ORF [nucleotides 213-1187 (Stop)] of the galactinol synthase 5 gene.

SEQ ID NO:6 is the 324 amino acid sequence encoded by the ORF [nucleotides 213-1187 (Stop)] of SEQ ID NO: 5

SEQ ID NO:7 is the amino acid sequence of the galactinol synthase from *Pisum sativum* (NCBI GenBank Identifier (GI) No. 5541885).

SEQ ID NO:8 is the amino acid sequence of the galactinol synthase from *Arabidopsis thaliana* (NCBI GenBank Identifier (GI) No. 15223567).

SEQ ID NO:9 is the amino acid sequence of the galactinol synthase from *Glycine max* (NCBI GenBank Identifier (GI) No. 32345694).

SEQ ID NO:10 represents the 1406 bp of the soybean nucleotide sequence of the galactinol synthase 1 gene.

SEQ ID NO:11 represents the 1350 bp of the soybean nucleotide sequence galactinol synthase 2 gene.

SEQ ID NO:12 is the forward primer used to amplify part of galactinol synthase 1 as described in Example 6.

SEQ ID NO:13 is the reverse primer used to amplify part of galactinol synthase 1 as described in Example 6.

SEQ ID NO:14 is the 519 bp sequence amplified from the galactinol synthase 1 gene (SEQ ID NO:10) as described in Example 6.

SEQ ID NO:15 is the forward primer used to amplify part of galactinol synthase 2 as described in Example 6.

SEQ ID NO:16 is the reverse primer used to amplify part of galactinol synthase 2 as described in Example 6.

SEQ ID NO:17 is the 519 bp sequence amplified from the galactinol synthase 2 gene (SEQ ID NO:11) as described in Example 6.

SEQ ID NO:18 is the forward primer used to amplify part of galactinol synthase 3 as described in Example 6.

SEQ ID NO:19 is the reverse primer used to amplify part of galactinol synthase 3 as described in Example 6.

SEQ ID NO:20 is the 519 bp sequence amplified from the galactinol synthase 3 gene (SEQ ID NO:1) as described in Example 6.

SEQ ID NO:21 is the forward primer used to isolate and amplify the soybean PM29 promoter as described in Example 10.

SEQ ID NO:22 is the reverse primer used to isolate and amplify the soybean PM29 promoter as described in Example 10.

SEQ ID NO:23 is the 597 bp sequence of the soybean PM29 promoter.

SEQ ID NO:24 is the forward primer used to re-amplify the PM29 promoter as described in Example 11.

SEQ ID NO:25 is the reverse primer used to re-amplify the PM29 promoter as described in Example 11.

SEQ ID NO:26 is the sequence of two copies of the Eag1-ELVISLIVES sequence as described in Example 11.

SEQ ID NO:27 represents the sequence of the complementary strand of SEQ ID NO: 26.

SEQ ID NO:28 represents the sequence of a truncated version of the two copies of the ELVISLIVES (ELEL) linker.

SEQ ID NO:29 is the 8810 bp sequence of vector SH50.

SEQ ID NO:30 is the 4479 bp sequence of vector pKR57.

SEQ ID NO:31 is the 5010 bp sequence of vector pKR63.

SEQ ID NO:32 is the 5414 bp sequence of v pDS1.

SEQ ID NO:33 is the 7085 bp sequence of vector pKR72.

SEQ ID NO:34 is the 5303 bp sequence of vector pDS2.

SEQ ID NO:35 is the 8031 bp sequence of vector pDS3 (orientation 2).

SEQ ID NO:36 is the 9616 bp sequence of vector SH60.

SEQ ID NO:37 is the 1585 bp sequence of the Not1 fragment of vector pJMS10 (FIG. 3) described in Example 13.

The sequence descriptions and Sequence Listing attached hereto comply with the rules governing nucleotide and/or amino acid sequence disclosures in patent applications as set forth in 37 C.F.R. § 1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference.

DETAILED DESCRIPTION OF THE INVENTION

In the context of this disclosure, a number of terms shall be utilized. The terms "polynucleotide," "polynucleotide sequence," "nucleic acid sequence," and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1 or 3 or 5, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

A "recombinant DNA construct" comprises any of the isolated polynucleotides of the present invention operably linked to at least one regulatory sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

The "Clustal V method of alignment" corresponds to the alignment method labeled Clustal V (described by Higgins and Sharp (1989) CABIOS. 5: 151-153) and found in the Megalign program of the LASERGENE bioinformatics computing suite (DNASTAR Inc., Madison, Wis.). The "default parameters" are the parameters preset by the manufacturer of the program and for multiple alignments they correspond to GAP PENALTY=10 and GAP LENGTH PENALTY=10, while for pairwise alignments they are KTUPLE 1, GAP PENALTY=3, WINDOW=5 and DIAGONALS SAVED=5. After alignment of the sequences, using the Clustal V program, it is possible to obtain a "percent identity" by viewing the "sequence distances" table in the same program.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment, which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs:1, 3 or 5 and the complement of such nucleotide sequences may be used to affect the expression and/or function of a galactinol synthase in a host cell. A method of using an isolated polynucleotide to affect the level of expression of a polynucleotide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridization, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers to any gene that is not a native gene, comprising regulatory and coding sequences that are not found together in nature. Accordingly, a recombinant DNA construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or recombinant DNA constructs. A "transgene" is an isolated nucleic acid fragment or recombinant DNA construct that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence, which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Convergent promoters" refers to promoters that are situated on either side of the isolated nucleic acid fragment of interest such that the direction of transcription from each promoter is opposing each other. Any promoter useful in plant transgene expression can be used. The promoters can be the same or different. The promoters are convergent with the isolated nucleic acid fragment being situated between the convergent promoters. It is important that the promoters have similar spatial and temporal activity, i.e., similar spatial and temporal patterns of expression, so that double-stranded RNA is produced in plants or plant organs by the recombinant construct that is stably integrated into the genome of the plant or plant organ. This has been described in U.S. provisional application 60/578,404, filed Jun. 9, 2004 which is filed simultaneously herewith. Also, this is described in U.S. provisional application 60/625,835, filed Nov. 8, 2004.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

Cosuppression technology constitutes the subject matter of U.S. Pat. No. 5,231,020, which issued to Jorgensen et al. on Jul. 27, 1999. The phenomenon observed by Napoli et al. in petunia was referred to as "cosuppression" since expression of both the endogenous gene and the introduced transgene were suppressed (for reviews see Vaucheret et al., Plant J. 16:651-659 (1998); and Gura, Nature 404:804-808 (2000)).

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) Plant J 16:651-659; and Gura (2000) Nature 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) Plant Cell 10:1747-1757).

In addition to cosuppression, antisense technology has also been used to block the function of specific genes in cells. Antisense RNA is complementary to the normally expressed RNA, and presumably inhibits gene expression by interacting with the normal RNA strand. The mechanisms by which the expression of a specific gene are inhibited by either antisense or sense RNA are on their way to being understood. However, the frequencies of obtaining the desired phenotype in a transgenic plant may vary with the design of the construct, the gene, the strength and specificity of its promoter, the method of transformation and the complexity of transgene insertion events (Baulcombe, Curr. Biol. 12(3):R82-84 (2002); Tang et al., Genes Dev. 17(1):49-63 (2003); Yu et al., Plant Cell. Rep. 22(3):167-174 (2003)). Cosuppression and antisense inhibition are also referred to as "gene silencing", "post-transcriptional gene silencing" (PTGS), RNA interference or RNAi. See for example U.S. Pat. No. 6,506,559.

MicroRNAs (miRNA) are small regulatory RNSs that control gene expression. miRNAs bind to regions of target RNAs and inhibit their translation and, thus, interfere with production of the polypeptide encoded by the target RNA. miRNAs can be designed to be complementary to any region of the target sequence RNA including the 3' untranslated region, coding region, etc. miRNAs are processed from highly structured RNA precursors that are processed by the action of a ribonuclease III termed DICER. While the exact mechanism of action of miRNAs is unknown, it appears that they function to regulate expression of the target gene. See, e.g., U.S. Patent Publication No. 2004/0268441 A1 which was published on Dec. 30, 2004.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or pro-peptides present in the primary translation product have been removed. "Precursor protein" or the term "precursor" when used in describing a protein refers to the primary product of translation of mRNA; i.e., with pre- and pro-peptides still present. Pre- and pro-peptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art.

The term "vector" refers to a vehicle used for gene cloning to insert a foreign nucleic acid fragment into the genome of a host cell.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising:
 (a) a nucleotide sequence encoding a polypeptide having galactinol synthase activity, wherein the polypeptide has an amino acid sequence of at least 85% identity, when compared to one of SEQ ID NO: 2 or 4 or 95% identity when compared to one of SEQ ID NO:6, based on the Clustal V method of alignment,
 (b) all or part of the isolated polynucleotide comprising (a) for use in co-suppression or antisense suppression of endogenous nucleic acid sequences encoding polypeptides having galactinol synthase activity, or
 (c) a complement of the nucleotide sequence of (a) or (b), wherein the complement and the nucleotide sequence consist of the same number of nucleotides and are 100% complementary.

This invention also includes the isolated complement of such polynucleotides, wherein the complement and the polynucleotide consist of the same number of nucleotides, and the nucleotide sequence of the complement and the polynucleotide have 100% complementarity.

Nucleic acid fragments encoding at least a portion of several galactinol synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other galactinol synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NOs:1, 3, or 5 and the complement of such nucleotide sequences may be used in such methods to obtain a nucleic acid fragment encoding a substantial portion of an amino acid sequence of a galactinol synthase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may in plant or in organ, tissue or cell culture.

The term "plant organ" refers to plant tissue or group of tissues that constitute a morphologically and functionally distinct part of a plant. The term "genome" refers to the following: 1. The entire complement of genetic material (genes and non-coding sequences) is present in each cell of an organism, or virus or organelle. 2. A complete set of chromosomes inherited as a (haploid) unit from one parent. The term "stably integrated" refers to the transfer of a nucleic acid fragment into the genome of a host organism or cell resulting in genetically stable inheritance.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of galactinol synthase, galactinol, and raffinose saccharides in those cells.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression of the recombinant DNA construct.

Plasmid vectors comprising the instant isolated polynucleotides) (or recombinant DNA constructs) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or recombinant DNA construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In still another embodiment, the present invention concerns a galactinol synthase polypeptide having an amino acid sequence comprising at least 85% identical, based on the Clustal method of alignment, to a polypeptide of SEQ ID NO:2 or 4 or at least 95% identical to a polypeptide of SEQ ID NO:6. The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded galactinol synthase. An example of a vector for high level expression of the instant polypeptides in a bacterial host is provided (Example 5).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several hundred kb; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

This invention also relates to a method of reducing the raffinose saccharide content of soybean seeds by at least 30%, 40%, 50%, 60%, 70%, 80%, 90%, 95% or 100% or any integer percentage in between 30% to 100%.

Raffinose saccharides are a group of D-galactose-containing oligosaccharide derivatives of sucrose that are widely distributed in plants. Raffinose saccharides are characterized by the following general formula: [O-β-D-galactopyranosyl-$(1\rightarrow 6)_n$-α-glucopyranosyl-$(1\rightarrow 2)$-β-D-fructofuranoside where n=0 through n=4 are known respectively as sucrose, raffinose, stachyose, verbascose and ajugose.

More specifically, this invention concerns method for reducing the level of at least one raffinose saccharide in soybean comprising:
  (a) constructing a recombinant DNA construct comprising all or part of at least one isolated polynucleotide comprising a nucleotide sequence encoding a polypeptide having galactinol synthase activity for use in co-suppression or antisense suppression of endogenous nucleic acid sequences encoding polypeptides having galactinol synthase activity operably linked to at least one regulatory sequence; and
  (b) transforming a soybean cell with the recombinant DNA construct of (a); and
  (c) regenerating soybean plants from the transformed cells of step (c); and
  screening seeds obtained from the plants of (c) for an altered level of galactinol synthase in the transformed soybean cell when compared to a corresponding nontransformed soybean cell.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily using *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al. (1988) *BioTechnology* 6:923, Christou et al. (1988) *Plant Physiol.* 87:671-674); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya and pea (Grant et al. (1995) *Plant Cell Rep.* 15:254-258).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) (1987) 84:5354); barley (Wan and Lemaux (1994) *Plant Physiol.* 104:37); *Zea mays* (Rhodes et al. (1988) *Science* 240:204, Gordon-Kamm et al. (1990) *Plant Cell* 2:603-618, Fromm et al. (1990) *BioTechnology* 8:833; Koziel et al. (1993) *BioTechnology* 11: 194, Armstrong et al. (1995) *Crop Science* 35:550-557); oat (Somers et al. (1992) *BioTechnology* 10: 15 89); orchard grass (Horn et al. (1988) *Plant Cell Rep.* 7:469); rice (Toriyama et al. (1986) *Theor. Appl. Genet.* 205:34; Part et al. (1996) *Plant Mol. Biol.* 32:1135-1148; Abedinia et al. (1997) *Aust. J. Plant Physiol.* 24:133-141; Zhang and Wu (1988) *Theor. Appl. Genet.* 76:835; Zhang et al. (1988) *Plant Cell Rep.* 7:379; Battraw and Hall (1992) *Plant Sci.* 86:191-202; Christou et al. (1991) *Bio/Technology* 9:957); rye (De la Pena et al. (1987) *Nature* 325:274); sugarcane (Bower and Birch (1992) *Plant J.* 2:409); tall fescue (Wang et al. (1992) *BioTechnology* 10:691), and wheat (Vasil et al. (1992) *Bio/Technology* 10:667; U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect isolated nucleic acid fragment constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures the standard resource materials which describe specific conditions and procedures for the construction, manipulation and isolation of macromolecules (e.g., DNA molecules, plasmids, etc.), generation of recombinant organisms and screening and isolating of clones (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)) are well known.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones

A cDNA library representing mRNAs from soybean (*Glycine max*) tissue was prepared. The characteristics of the library are described below.

TABLE 1 cDNA Libraries from Soybean

| Library | Tissue | Clone |
|---|---|---|
| sdp3c | Soybean (*Glycine max* [L.]) developing pods 8-9 mm | sdp3c.pk013.c9 |
| srr3c | Soybean (*Glycine max* [L.], Bell) roots control for src3c. | srr3c.pk003.h12:fis srr3c.pk001.i20:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding galactinol synthase were identified by conducting BLAST (Basic Local Alignment Search Tool; Altschul et al. (1993) *J. Mol. Biol.* 215:403-410;) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the GenBank database as described above. ESTs that contain sequences more 5- or 3-prime can be found by using the BLAST algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLAST algorithm searches an amino acid query against a nucleotide database that is translated in all 6 reading frames. This search allows for differences in nucleotide codon usage between different species, and for codon degeneracy.

Example 3

Characterization of cDNA Clones Encoding Galactinol Synthase

The BLASTX search using the EST sequences from the clones listed in Table 2 revealed similarity of the polypeptides encoded by the cDNAs to galactinol synthase from *Pisum sativum* (NCBI GenBank Identifier (GI) No. 5541885, SEQ ID NO:7), *Arabidopsis thaliana* (NCBI GenBank Identifier (GI) No. 15223567, SEQ ID NO:8) and *Glycine max* (NCBI GenBank Identifier (GI) No. 32345694, SEQ ID NO:9). Shown in Table 2 are the BLAST results for the sequences encoding an entire protein ("CGS") derived from the entire cDNA inserts comprising the indicated cDNA clones ("fis"):

TABLE 2

BLAST Results for Sequences Encoding Polypeptides Homologous to Galactinol Synthase

| Clone | Status | BLAST pLog Score (NCBI) |
|---|---|---|
| sdp3c.pk013.c9:fis (SEQ ID NO: 2) | CGS | 149.57 (GI: 5541885) |
| srr3c.pk003.h12:fis (SEQ ID NO: 4) | CGS | 135.89 (GI: 15223567) |
| srr3c.pk001.i20:fis (SEQ ID NO: 6) | CGS | 166.70 (GI: 32345694) |

The sequence of the entire cDNA insert in the clones listed in Table 2 was determined. The data in Table 3 represent a calculation of the percent identity of the amino acid sequences set forth in SEQ ID Nos: 2, 4, and 6 and the sequences of *Pisum sativum* (SEQ ID NO: 7), *Arabidopsis thaliana* (SEQ ID NO: 8) and *Glycine max* (SEQ ID NO: 9).

TABLE 3

Percent Identity of Amino Acid Sequences Deduced From the Nucleotide Sequences of cDNA Clones Encoding Polypeptides Homologous to Galactinol Synthase

| Clone | SEQ ID NO: | Percent Identity to (Accession No.) |
|---|---|---|
| sdp3c.pk013.c9:fis | 2 | 82 (GI: 5541885) |
| srr3c.pk003.h12:fis | 4 | 75 (GI: 15223567) |
| srr3c.pk001.i20:fis | 6 | 92 (GI: 32345694) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a galactinol synthase. These sequences represent new soybean sequences encoding galactinol synthase.

The expression pattern of galactinol synthase 3, 4 and 5 during soybean seed development was analyzed via Lynx MPSS Brenner et al (2000) *Proc Natl Acad Sci USA* 97:1665-70) and is shown in Table 4.

TABLE 4*

| Clone Designation | 15 DAF | 20 DAF | 30 DAF | 40 DAF | 45 DAF | 50 DAF | 55 DAF | mature |
|---|---|---|---|---|---|---|---|---|
| sdp3c.pk013.c9 | — | — | — | 6 | 143 | 796 | 1979 | 1604 |
| srr3c.pk003.h12 | — | — | — | — | 21 | 151 | 152 | 133 |
| srr3c.pk001.i20 | — | — | 13 | — | 45 | 79 | 365 | 329 |

*Lynx MPSS profiles (expressed as adjusted PPM) of galactinol synthase 3 (sdp3c.pk013.c9), galactinol synthase 4 (srr3c.pk003.h12) and galactinol synthase 5 (srr3c.pk001.i20) during soybean seed development (DAF = days after flowering, mature = mature seed).

The results shown in Table 4 demonstrate that expression of all three galactinol synthases are only detectable during the later stages of seed development (45 DAF to mature seed). Galactinol synthase 4 is very lowly expressed compared to galactinol synthase 3 and 5, which show high and intermediate expression levels during late seed development. The pattern of expression between galactinol synthase 3 and 5 also differs: whereas galactinol synthase 3 expression levels increase during the course of late seed development, reaching a plateau in the mature seed, galactinol synthase 5 expression appears to be prominent mainly at 55 DAF and in mature seed.

Example 4

Expression of Recombinant DNA Constructs in Dicot Cells

A seed-specific expression cassette composed of the promoter and transcription terminator from the gene encoding the alpha subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/mL ethidium bromide for visualization of the DNA fragment. The fragment can then be purified from the agarose gel by digestion with GELase (Epicentre Technologies, Madison, Wis.) according to the manufacturer's instructions, ethanol precipitated, dried and resuspended in 20 □L of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Crude, partially purified or purified enzyme, either alone or as a fusion protein, may be utilized in assays for the evaluation of enzymatic activity of the instant polypeptides disclosed herein. Assays may be conducted under well-known experimental conditions which permit optimal enzymatic activity. Assays for galactinol synthase activity are presented by Odegard and Lumen (1995) Plant Physiol. 109: 505-511.

Example 6

Construction of Chimeric Vectors for Seed-targeted Co-suppression of Galactinol Synthase in Transgenic *Glycine max*

Vectors designed for the seed-specific co-suppression of galactinol synthase 1 galactinol synthase 2 and galactinol synthase 3 in soybean were assembled as described below.

Amplification of Partial Galactinol Synthase Polynucleotides

Polynucleotide fragments encoding parts of the galactinol synthase 1 (GAS1 (SEQ ID NO:6 of U.S. Pat. Nos. 5,773,699 and 5,648,210), galactinol synthase 2 (GAS2) in clone ses4d.pk0017.b8 (WO 01/77306) and galactinol synthase 3 (GAS3) in clone sdp3c.pk013.c9 were amplified by standard PCR methods using Pfu Turbo DNA polymerase (Stratagene, La Jolla, Calif.) and the following primer sets. The GAS1 oligonucleotide primers were designed to add a Not I restriction endonuclease site at the Send and a XhoI site to the 3' end (SEQ ID NO:12 and SEQ ID NO:13, respectively). The DNA sequence comprising the 519 bp polynucleotide from soybean GAS1 is shown in SEQ ID NO:14.

The GAS2 oligonucleotide primers were designed to add a XhoI restriction endonuclease site at the Send and a PstI site to the 3' end (SEQ ID NO:15 and SEQ ID NO:16 respectively). The DNA sequence comprising the 519 bp polynucleotide from soybean GAS2 is shown in SEQ ID NO:17.

The GAS3 oligonucleotide primers were designed to add a PstI restriction endonuclease site at the Send and a NotI site to the 3' end (SEQ ID NO:18 and 19, respectively). The DNA sequence comprising the 519 bp polynucleotide from soybean GAS3 is shown in SEQ ID NO:20.

Assembly of Vectors for the Co-suppression of Galactinol Synthase

Preparation of pJMS08: The polynucleotide products for GAS1, GAS2 and GAS3 obtained from the amplifications described above were digested with Not I, Xho1 and PSt1 and assembled into vector pJMS08 (FIG. 2) by the following steps. First, the plasmid KS151 [US patent publication 2003/0036197A1] was digested with Not I. Then, the isolated DNA fragments containing partial sequences of GAS1, GAS2 and GAS3 were inserted into Not I-digested plasmid KS151 to obtain plasmid pJMS08 (FIG. 2).

Plasmid KS151 also comprises nucleotides encoding HPT under the control of the T7 promoter and termination signals and the 35S promoter and Nos 3' terminator (US patent publication 2003/0036197A1). The KTi3 promoter and 3' transcription terminator region have been described by Jofuku et al. ((1989) *Plant Cell* 1:1079-1093). The KTI3 promoter directs strong embryo-specific expression of transgenes.

Figure 3:
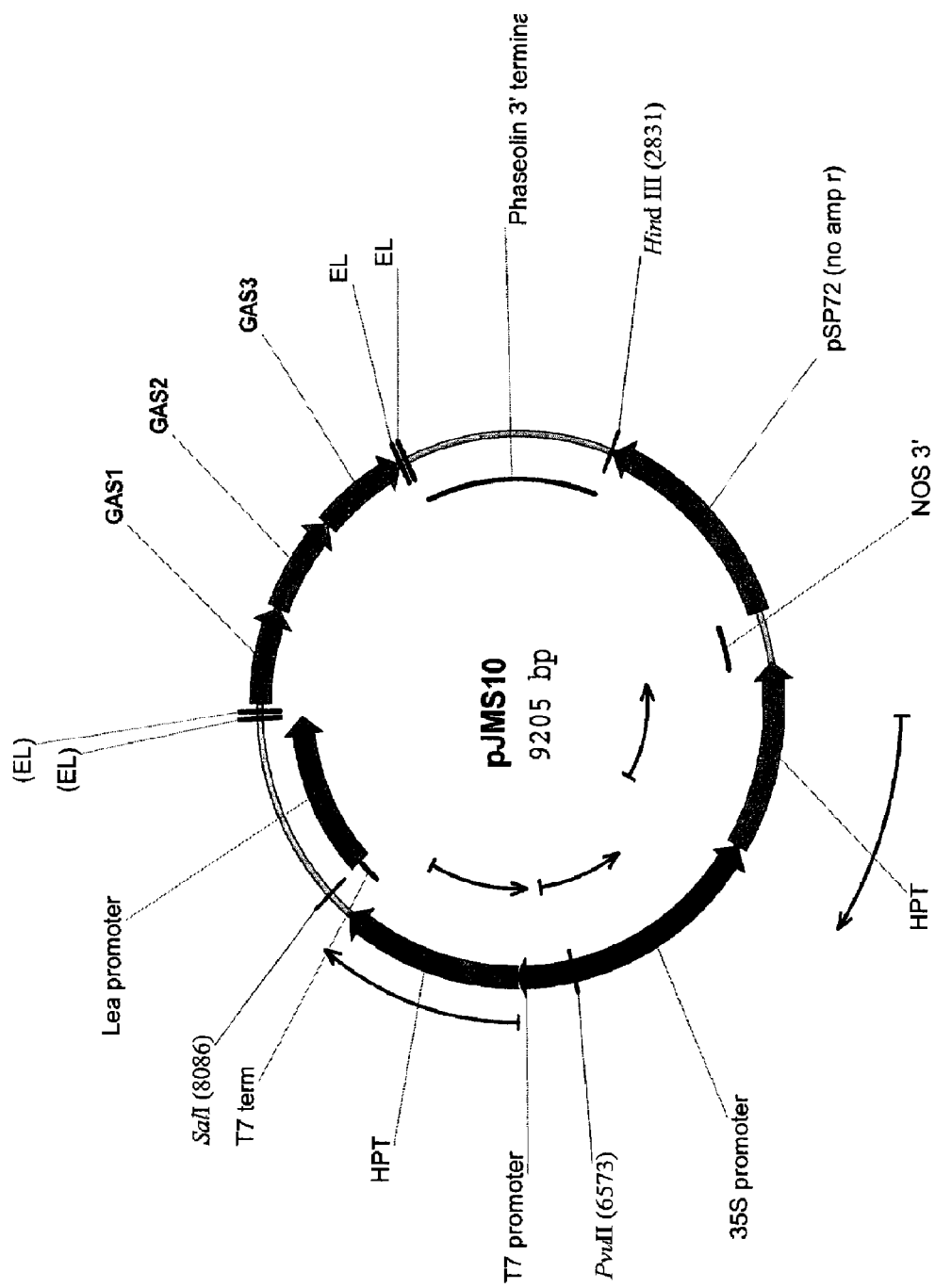
FIG. 3 shows vector pJMS10.

Preparation of pJMS10: The polynucleotide products for GAS1, GAS2 and GAS3 obtained from the amplifications described above were digested with Not I, Xho1 and PSt1 and assembled into vector pJMS10 (FIG. 3) by the following steps. From plasmid KS123 (prepared according to US Application No. 2004/0073975 A1, which published on Apr. 15, 2004) the HindIII cassette containing the beta-conglycinin promoter-phaseolin terminator was removed creating the plasmid KS120. To the unique BamHI site of plasmid KS120 a lea promoter-phaseolin terminator was inserted as a BamHI fragment creating plasmid KS127. The Lea promoter (Lee et al (1992) Plant Physiol. 100:2121-2122; Genbank Accession no. M97285) was amplified from genomic A2872 soybean DNA and a phaseolin 3' end was added as described in US patent publication 2003/0036197 A1. To KS127 an EL linker was added to a unique Not1 site as described in U.S. patent publication 2003/0036197 A1, creating plasmid KS139. To KS139 an EL linker was added to a unique Not1 site as described in US patent publication 2003/0036197 A1, creating plasmid KS147. Plasmid KS147 also comprises nucleotides encoding HPT under the control of the T7 promoter and termination signals and the 35S promoter and Nos 3'. Then, the isolated DNA fragments containing partial sequences of GAS1, GAS2 and GAS3 were inserted into the Not I-digested plasmid KS147 to obtain plasmid pJMS10 (FIG. 3).

Example 7

Construction of Chimeric Vectors for Seed-targeted Co-suppression of Galactinol Synthase in Transgenic *Glycine max*

Vectors designed for the seed-specific co-suppression of galactinol synthase 3, galactinol synthase 4 and galactinol synthase 5 in soybean can be assembled as described below.

Amplification of Partial Galactinol Synthase Polynucleotides

Polynucleotide fragments encoding parts of the galactinol synthase 4 (SEQ ID NO: 3), galactinol synthase 5 (SEQ ID NO:5) and galactinol synthase 3 (SEQ ID NO:1) are amplified by standard PCR methods using Pfu Turbo DNA polymerase (Stratagene, La Jolla, Calif.). Appropriate primer sets are chosen, giving polynucleotide fragments of similar length as described for GAS1, 2 and 3 (Example 6), which is well within the routine skill in the art.

Assembly of Vectors for the Co-suppression of Galactinol Synthase

The assembly of vectors containing GAS 3, 4, and 5 for the co-suppression of galactinol synthase is performed essentially as described for GAS1, 2 and 3 in Example 6.

Transformation into soybean somatic embryos and carbohydrate analysis will be performed as described below for GAS1, 2, and 3.

It is expected, that a similar reduction in Raffinose Saccharides in soybean seeds will be observed using GAS 3, 4, 5 as the one observed with GAS1, 2, and 3.

Example 8

Transformation of Soybean Somatic Embryos with Galactinol Synthase Co-suppression Vectors To study the possibility of reducing Raffinose Family Oligosaccharides (RFOs), soybean somatic embryos were transformed with the seed-specific expression vectors pJMS08 (FIG. 2) or pJMS10 (FIG. 3) by the method of particle gun bombardment (Klein, T. M. et al. (1987) Nature (London) 327:70-73; U.S. Pat. No. 4,945,050). Soybean somatic embryos from the Jack cultivar were induced as follows. Cotyledons (3 mm in length) were dissected from surface sterilized, immature seeds and were cultured for an additional 6-10 weeks in the light at 26° C. on a Murashige and Skoog media containing 7 g/L agar and supplemented with 10 mg/mL 2,4-D. Globular stage somatic embryos, which produced secondary embryos, were then excised and placed into flasks containing liquid MS medium supplemented with 2,4-D (10 mg/mL) and cultured in the light on a rotary shaker. After repeated selection for clusters of somatic embryos that multiplied as early, globular staged embryos, the soybean embryogenic suspension cultures were maintained in 35 mL liquid media on a rotary shaker, 150 rpm, at 26° C. with fluorescent lights on a 16:8 hour day/night schedule. Cultures were subcultured every two weeks by inoculating approximately 35 mg of tissue into 35 mL of liquid medium.

Soybean embryogenic suspension cultures were then transformed by the method of particle gun bombardment using a DuPont Biolistic™ PDS1000/HE instrument (helium retrofit). To 50 µL of a 60 mg/µL 1 mm gold particle suspension were added (in order): 5 µL of 1 mg/µL DNA (pJMS01 plus pJMS02, pRM02 plus pRM03, pRM01, or pRM04), 20 µL of 0.1 M spermidine, and 50 µL of 2.5 M CaCl$_2$. The particle preparation was then agitated for three minutes, spun in a microfuge for 10 seconds and the supernatant removed. The DNA-coated particles were then washed once in 400 µL 70% ethanol and resuspended in 40 µL of anhydrous ethanol. The DNA/particle suspension was sonicated three times for one second each. Five µL of the DNA-coated gold particles was then loaded on each macro carrier disk.

Approximately 300-400 mg of a two-week-old suspension culture was placed in an empty 60×15-mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos.

These immature soybean embryos were dried-down (by transferring them into an empty small petridish that was seated on top of a 10 cm petridish containing some agar gel to allow slow dry down) to mimic the last stages of soybean seed development.

Dried-down embryos are capable of producing plants when transferred to soil or soil-less media. Storage products produced by embryos at this stage are similar in composition to storage products produced by zygotic embryos at a similar stage of development and most importantly the storage product profile is predictive of plants derived from a somatic embryo line (WO 94/11516, published May 26, 1994)).

Example 9

Carbohydrate Analysis of Transgenic Soybean Somatic Embryos

The carbohydrate composition of transgenic somatic embryos identified in Example 6 as containing the pJMS08 or pJMS10 cassettes was measured by high performance anion exchange chromatography/pulsed amperometric detection (HPAE/PAD). Fresh individual somatic embryos from transgenic lines were rapidly washed in water, dried on a paper towel, and transferred into 1.5 mL microcentrifuge tubes. Ethanol (80%) was added to the tubes and the samples were heated to 70° C. for 15 minutes. The samples were centrifuged at 14,000 rpm for 5 minutes at 4° C. and the supernatant collected. The pellet was re-extracted two additional times with 80% ethanol at 70° C. The supernatants were combined, dried down in a speedvac, and the pellet re-suspended in water.

For HPAE analysis, the extracts were filtered through a 0.2 µm Nylon-66 filter (Rainin, Emeryville, Calif.) and analyzed by HPAE/PAD using a DX500 anion exchange analyzer (Dionex, Sunnyvale, Calif.) equipped with a 250×4 mm Carbo-Pac PA1 anion exchange column and a 25×4 mm CarboPac PA guard column. Soluble carbohydrates were separated with a 25 minute linear gradient of 0.5 to 170 mM NaAc in 150 mM NaOH at a flow rate of 1.0 mL/min. Soluble sugars were identified by comparison to standards (glucose, fructose, sucrose, raffinose, stachyose, and verbascose) using HPAE/PAD.

Figure 4:
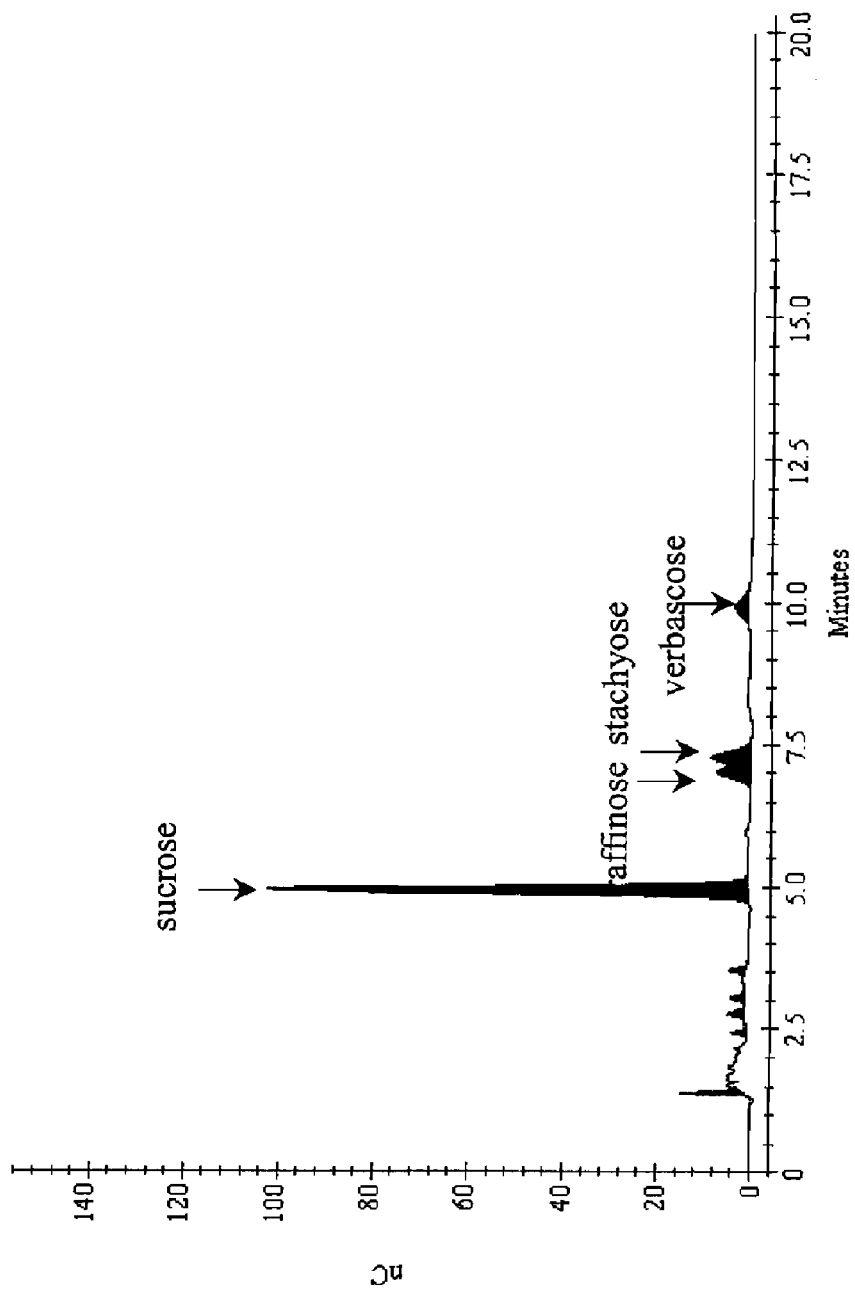
FIG. 4 shows a typical carbohydrate profile of transgenic somatic embryos co-suppressing galactinol synthase.

FIG. 4 and Table 5 show a typical carbohydrate profile resulting from HPAE/PAD analysis of transgenic soybean somatic embryos co-suppressing galactinol synthase. A clear reduction in RFOs (raffinose, stachyose and vebascose) can be observed as compared to FIG. 5 and wild type values in Table 5.

Figure 5:
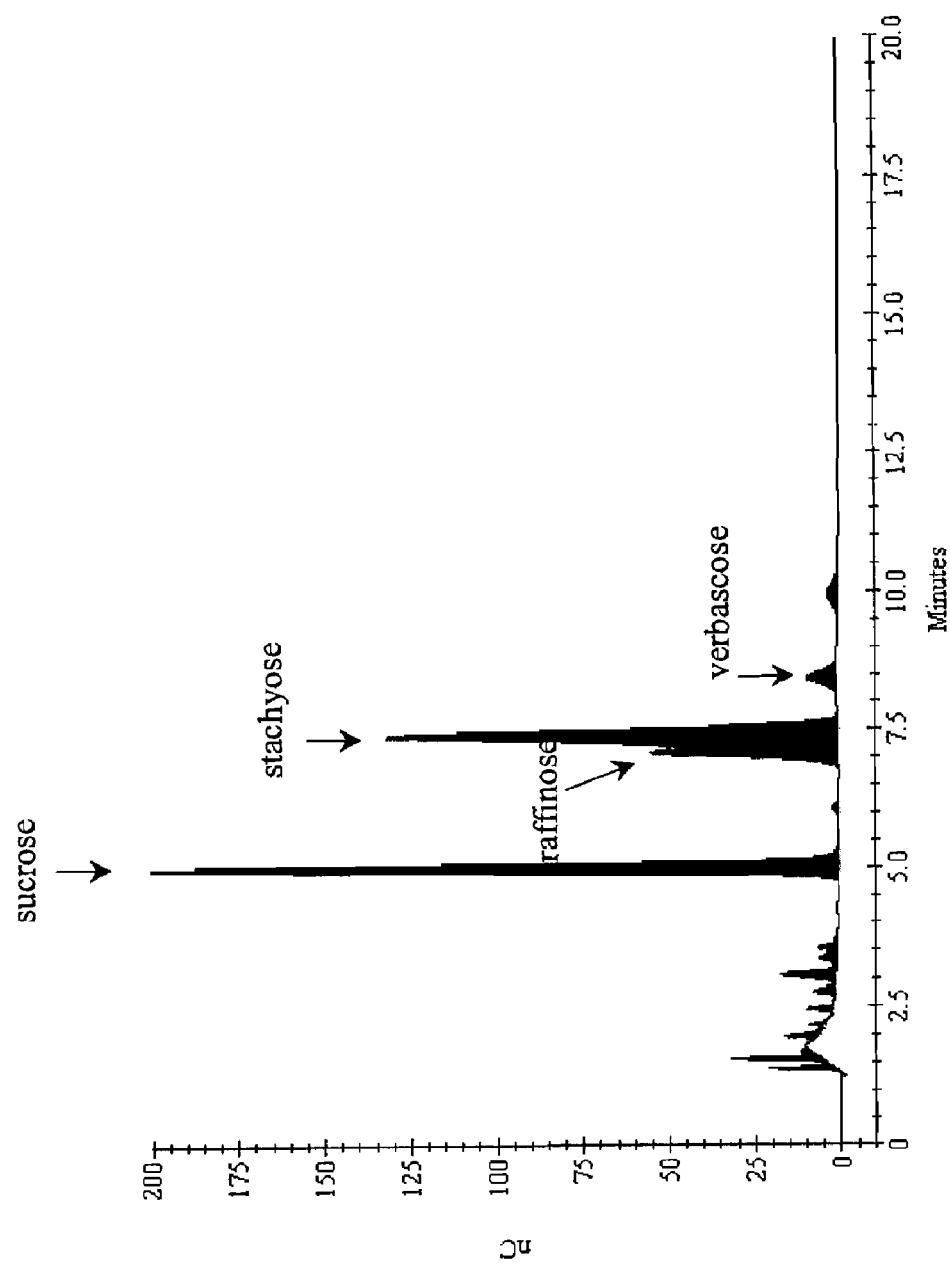
FIG. 5 shows a typical carbohydrate profile of a wild type soybean somatic embryo.

FIG. 5 shows a typical carbohydrate profile resulting from HPAE/PAD analysis of a soybean somatic embryo showing a wild type carbohydrate phenotype.

The results for two different events showing cosuppression experiments of the three isoforms of Galactinol Synthases 1, 2, and 3 are shown in Table 5 above. For each event, 6 seeds were analyzed. The results are expressed in μmol/g dwt (sugar unit), where the dry weight calculation was based on 7% moisture content of seed.

TABLE 5

| Event | seed | wt(g) | gol | sucr | raff | stach | verb | totRSA | Stach/raff | Pheno-type | % reduction |
|---|---|---|---|---|---|---|---|---|---|---|---|
| 1231-1-1-1 | 1 | 0.14 | 1.37 | 179.99 | 18.35 | 11.90 | 0.14 | 43.94 | 0.65 | Low RFO | 48.45 |
| 1231-1-1-1 | 2 | 0.14 | 1.12 | 120.71 | 19.84 | 32.33 | 0.00 | 85.62 | 1.63 | WT | |
| 1231-1-1-1 | 3 | 0.19 | 0.68 | 159.38 | 18.06 | 20.57 | 0.00 | 59.88 | 1.14 | Low RFO | 29.77 |
| 1231-1-1-1 | 4 | 0.20 | 0.83 | 122.36 | 17.84 | 31.62 | 0.99 | 84.88 | 1.77 | WT | |
| 1231-1-1-1 | 5 | 0.19 | 0.78 | 148.20 | 16.14 | 19.20 | 0.00 | 55.32 | 1.19 | Low RFO | 35.10 |
| 1231-1-1-1 | 6 | 0.14 | 0.57 | 161.80 | 15.75 | 12.98 | 0.00 | 42.28 | 0.82 | Low RFO | 50.41 |
| Mean WT | | 0.17 | 0.97 | 121.49 | 18.84 | 31.97 | 0.49 | 85.24 | 1.70 | | 0.00 |
| Mean Low RFO | | 0.16 | 0.85 | 162.34 | 17.07 | 16.16 | 0.03 | 50.35 | 0.95 | | 40.93 |
| 1231-1-1-3 | 1 | 0.13 | 2.12 | 187.39 | 21.03 | 13.56 | 0.41 | 51.51 | 0.64 | Low RFO | 52.67 |
| 1231-1-1-3 | 2 | 0.13 | 2.15 | 186.36 | 25.69 | 16.09 | 0.43 | 61.30 | 0.63 | Low RFO | 43.68 |
| 1231-1-1-3 | 3 | 0.13 | 2.09 | 193.18 | 25.31 | 33.42 | 0.00 | 94.25 | 1.32 | WT | |
| 1231-1-1-3 | 4 | 0.15 | 0.81 | 231.88 | 20.46 | 8.90 | 0.21 | 39.72 | 0.44 | Low RFO | 63.51 |
| 1231-1-1-3 | 5 | 0.14 | 1.28 | 236.19 | 19.82 | 13.43 | 0.19 | 48.54 | 0.68 | Low RFO | 55.40 |
| 1231-1-1-3 | 6 | 0.15 | 1.63 | 164.68 | 17.05 | 43.41 | 1.11 | 108.84 | 2.55 | WT | |
| Mean WT | | 0.14 | 1.86 | 178.93 | 21.18 | 38.41 | 0.56 | 101.55 | | | 0.00 |
| Mean Low RFO | | 0.14 | 1.59 | 210.46 | 21.75 | 12.98 | 0.31 | 50.27 | | | 50.50 |

TotRSA (total raffinose saccharides) refers to the α-galactose content present in the sum of galactinol (gol, 1 mol α-galactose/mole), raffinose (raft, 1 mol α-galactose/mole), stachyose (stach, 2 mol α-galactose/mole) and verbascose (verb, 3 mol α-galactose/mole). Sucrose is sucr. % Reduction indicates the change in total RFOs compared to the wild type.

Example 10

Isolation of Soybean PM29 Promoter

The promoter of a soybean seed maturation protein was isolated using a polymerase chain reaction (PCR) based approach. Soybean genomic DNA was digested to completion with a DNA restriction enzyme that generates blunt ends (DraI, EcoRV, PvuII or StuI, for example) according to standard protocols. The Universal GenomeWalker™ kit from Clonetech™ (Product User Manual No. PT3042-1) was used to ligate adaptors to the ends of the genomic DNA fragments. Nested primers are also supplied in the Universal GenomeWalker™ kit that are specific for the adaptor sequence (AP1 and AP2, for the first and second adaptor primer, respectively). Two gene specific primers (GSP1 and GSP2) were designed for the soybean PM29 gene based on the 5' coding sequences in PM29 cDNA in DuPont EST database. The oligonucleotide sequences of the GSP1 and GSP2 primers (SEQ ID NO:21 and SEQ ID NO:22, respectively) contain recognition sites for the restriction enzyme BAMH I.

The AP2 primer from the Universal GenomeWalker™ kit contains a Sal I restriction site. The AP1 and the GSP1 primers were used in the first round PCR using each of the adaptor ligated genomic DNA populations (DraI, EcoRV, PvuII or StuI) under conditions defined in the GenomeWalker™ protocol. Cycle conditions were 94° C. for 4 minutes; 94° C. for 2 seconds and 72° C. for 3 minutes, 7 cycles; 94° C. for 2 seconds and 67° C. for 3 minutes, 32 cycles; 67° C. for 4 minutes. The products from each of the first run PCRs were diluted 50-fold. One microliter from each of the diluted products was used as templates for the second PCR with the AP2 and GSP2 as primers. Cycle conditions were 94° C. for 4 minutes; 94° C. for 2 seconds and 72° C. for 3 minutes, 5 cycles; 94° C. for 2 seconds and 67° C. for 3 minutes, 20 cycles; 67° C. for 3 minutes. Agarose gels were run to determine which PCR gave an optimal fragment length. A 679 bp genomic fragment was detected and isolated from the EcoRV-digested genomic DNA reaction. The genomic fragment was digested with BamH I and Sal I and cloned into Bluescript KS+ vector for sequencing. Finally, sequencing data indicated that this genomic fragment contained a 597 bp soybean PM29 promoter sequence as shown in SEQ ID NO:23.

Example 11

Construction of Galactinol Synthase Silencing Plasmids Driven by PM29

Figure 6:
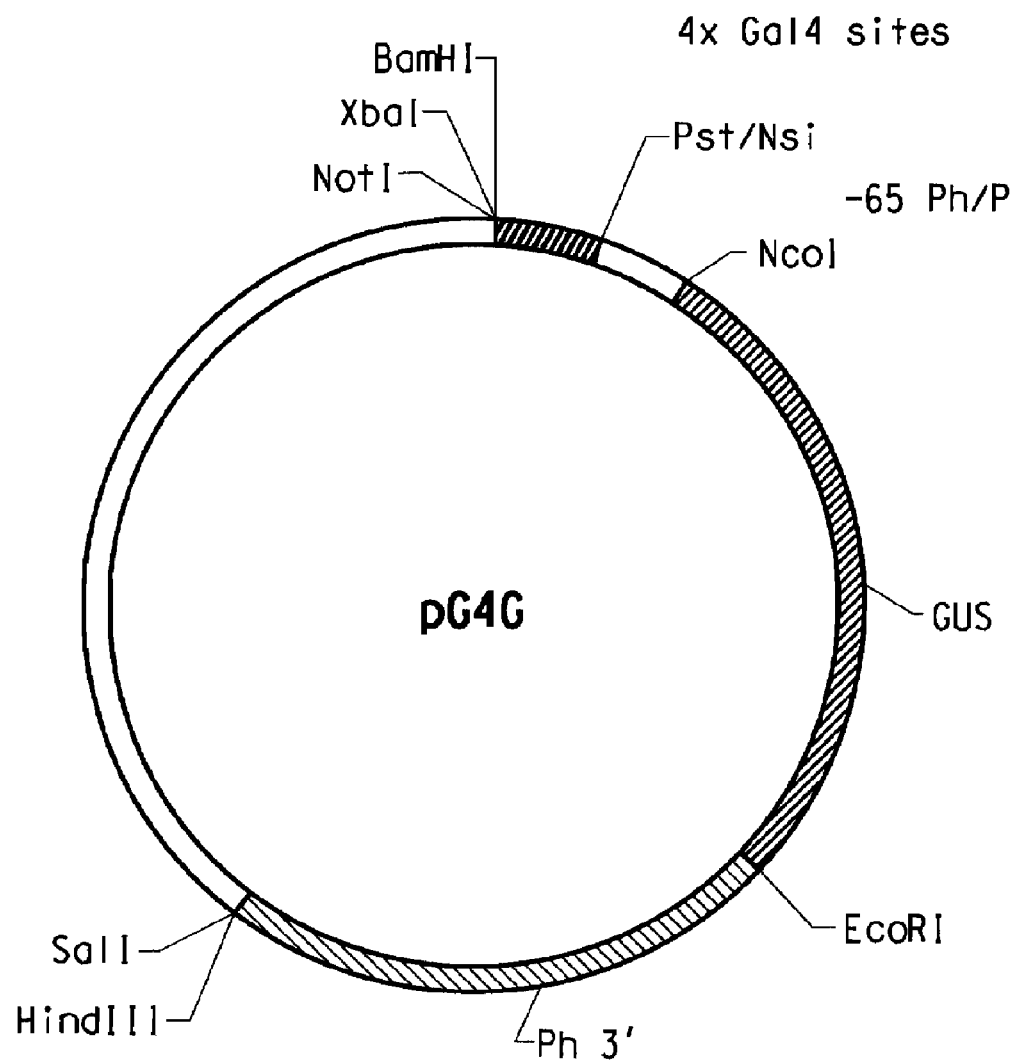
FIG. 6 shows vector pG4G.

Two oligonucleotides were designed to re-amplify the PM29 promoter with either BamH I or Nco I sites (SEQ ID NO:24 and SEQ ID NO:25, respectively). The re-amplified PM29 promoter fragment was digested with BamH I and Nco I, purified and cloned into the BamH I and Nco I sites of plasmid pG4G (FIG. 6) to make the fusion between the soybean PM29 promoter-GUS fusion (pSH43). The plasmid pG4G has been described in U.S. Pat. No. 5,968,793, the contents of which are hereby incorporated by reference.

Preparation of SH55 and SH49:

Plasmid pSH43 (described above) was digested with NcoI, filled in with vent polymerase (obtained from New England Biolabs Inc.) and subsequently digested with BamHI (5' end of the promoter). The resulting promoter fragment was isolated and cloned into pBluescript II SK (+) (Stratagene, Inc.) previously cut with XbaI (and filled in by vent polymerase) and BamHI creating the plasmids pBluescriptPM29. This construct contains a unique Not1 site at the 3' end of the promoter. Two copies of the Eag1-ELVISLIVES sequence (SEQ ID NO:26) were added on the 5' site of the Not1 site as described in EP1297163 A2 (PCT Publication No. WO 2002/000904, which published Jan. 3, 2002).

The promoter fragment was isolated using a BamHI/Not1 digestion and ligated into pJMS10 plasmid previously cut with BamH1 (partial) and Not1. The pJMS10 plasmid also contains the complementary strand of SEQ ID NO:26 (SEQ ID NO:27) 3' of the Not1 site. This ligation resulted in the following plasmid: SH55 (PM29 promoter-ELEL-Not1-ELEL-Phaseolin terminator) and SH49. SH49 is identical to SH55 with the exception of a truncated ELEL sequence (SEQ ID NO:28) at the 3' border of the Not1. The truncated sequence is missing the "tgacca" of the ELEL sequence at the 3' border of the Not1 and was identified after sequence verification of the plasmid and probably originated during the PCR amplification of the ELEL linker. This truncation has no effect on the ability of silencing the GAS genes as is evident from Example 12.

Figure 7:
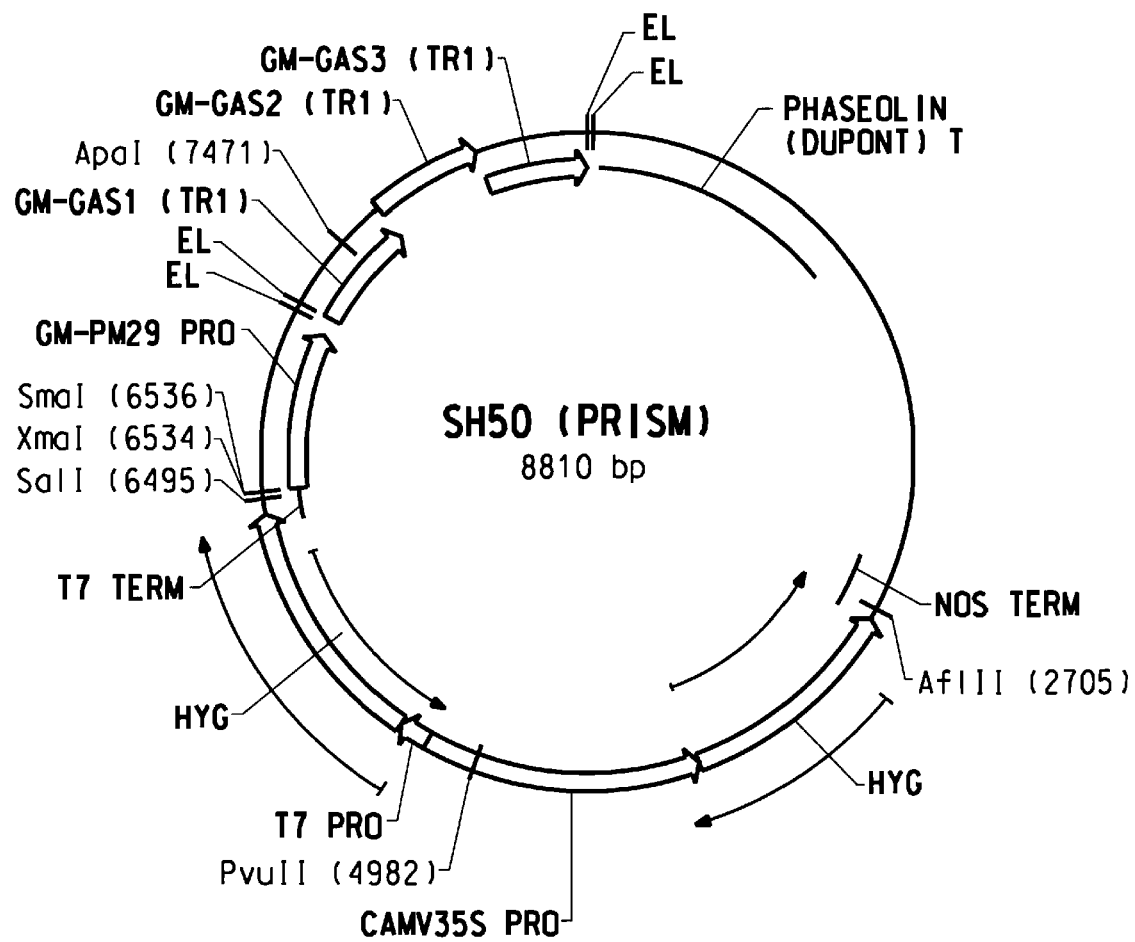
FIG. 7 shows vector SH50.

Preparation of SH50:

A Not1 fragment containing the partial sequences of soybean GAS1 (SEQ ID NO:14), GAS2 (SEQ ID NO:17) and GAS3 (SEQ ID NO:20) was digested from pJMS10 (described above) and then ligated into SH49 previously digested with Not1, creating the plasmid SH50 (SEQ ID NO:29 and FIG. 7).

Example 12

Raffinose Family Oligosaccharide (RFO) Analysis of PM29 Driven Transgenic Soybean Somatic Embryos and Mature Seeds Soybean somatic embryos were transformed with a seed-preferred expression vector SH50 (SEQ ID NO:29 and FIG. 7) by the method described in Example 8.

Figure 8:
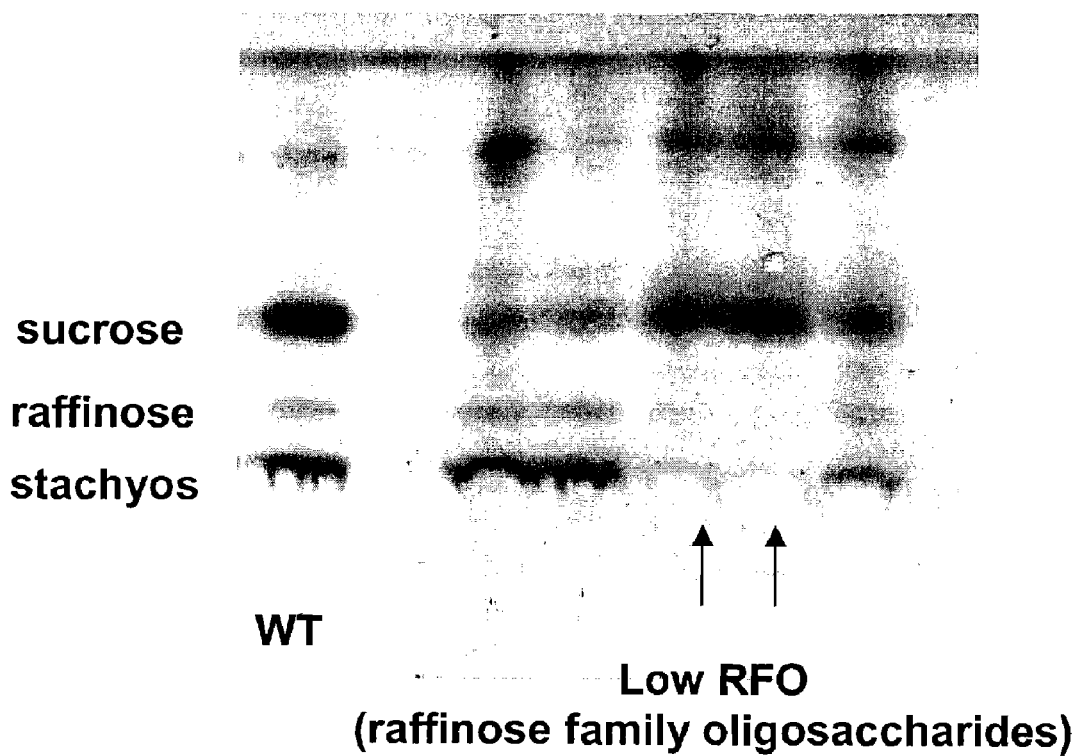
FIG. 8 shows a TLC analysis of somatic embryos containing the PM29 driven recombinant expression construct described in Example 11.
Figure 9:
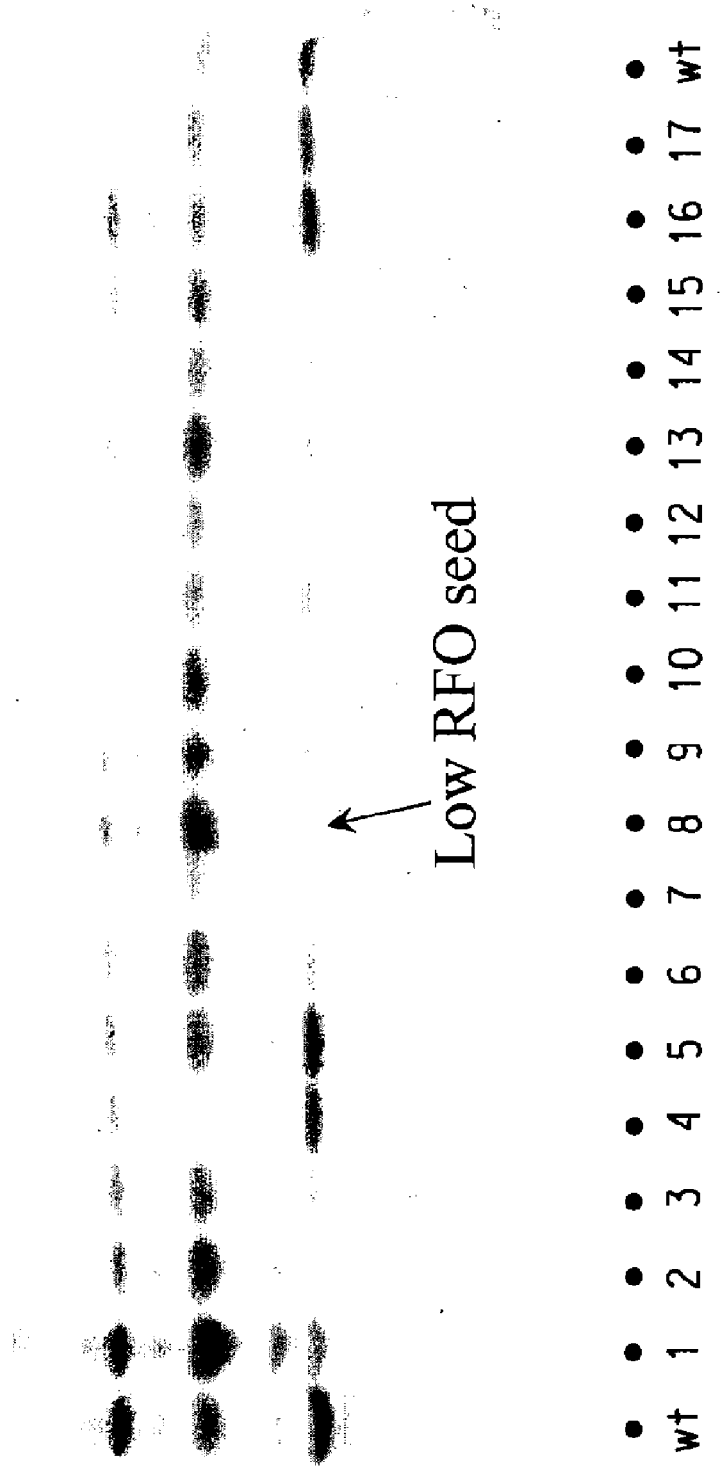
FIG. 9 shows a TLC analysis of mature soybean seeds containing the PM29 driven recombinant expression construct described in Example 11.

Raffinose Family Oligosaccharides (galactinol, raffinose, stachyose, etc.) of transgenic somatic embryos and seeds containing the PM29 promoter driven recombinant expression construct described in Example 11 was measured by thin layer chromatography. Somatic embryos or seed chips were extracted with hexane then dried. The dried material was resuspended in 80% methanol, incubated at room temperature for 1-2 hours, centrifuged, and 2 microliters of the supernatant is spotted onto a TLC plate (Kieselgel 60 CF, from EM Scientific, Gibbstown, N.J.; Catalog No. 13749-6). The TLC was run in ethylacetate:isopropanol:20% acetic acid (3:4:4) for 1-1.5 hours. The air dried plates were sprayed with 2% sulfuric acid and heated until the charred sugars were detected. As shown in FIG. 8 two lines show reduced levels of raffinose sugars (raffinose and stachyose lowest bands) when compared to a to wild-type soybean. The arrow indicates somatic embryos with reduced raffinose family oligosaccharides. (WT=wild type control, S=sucrose, Rf=raffinose and St=stachyose standard). FIG. 9 shows a TLC analysis of mature seed chips from a soybean line transformed with SH50 and revealed an almost complete reduction in raffinose and stachyose (RFO) sugars in seeds when compared to wild-type soybean. The plate shows that 13 out of 17 seeds from a single event show a dramatic reduction in raffinose family oligosaccharides (RFO).

Carbohydrate Analysis of Transgenic Soybean Seeds

The carbohydrate composition of transgenic soybean seeds containing the PM29 promoter driven recombinant expression construct described in Example 11 (SH50) was measured by high performance anion exchange chromatography/pulsed amperometric detection (HPAE/PAD). Seed chips were extracted in ethanol (80%) and heated to 70° C. for 15 minutes. The samples were centrifuged at 14,000 rpm for 5 minutes at 4° C. and the supernatant collected. The pellet was re-extracted two additional times with 80% ethanol at 70° C. The supernatants were combined, dried down in a speedvac, and the pellet re-suspended in water.

For HPAE analysis, the extracts were filtered through a 0.2 μm Nylon-66 filter (Rainin, Emeryville, Calif.) and analyzed by HPAE/PAD using a DX500 anion exchange analyzer (Dionex, Sunnyvale, Calif.) equipped with a 250×4 mm CarboPac PA1 anion exchange column and a 25×4 mm CarboPac PA guard column. Soluble carbohydrates were separated with a 20 isocratic run in 150 mM NaOH at a flow rate of 1.0 mL/min. Soluble sugars were identified by comparison to standards (glucose, fructose, sucrose, raffinose, stachyose, and verbascose) using HPAE/PAD.

Figure 10A:
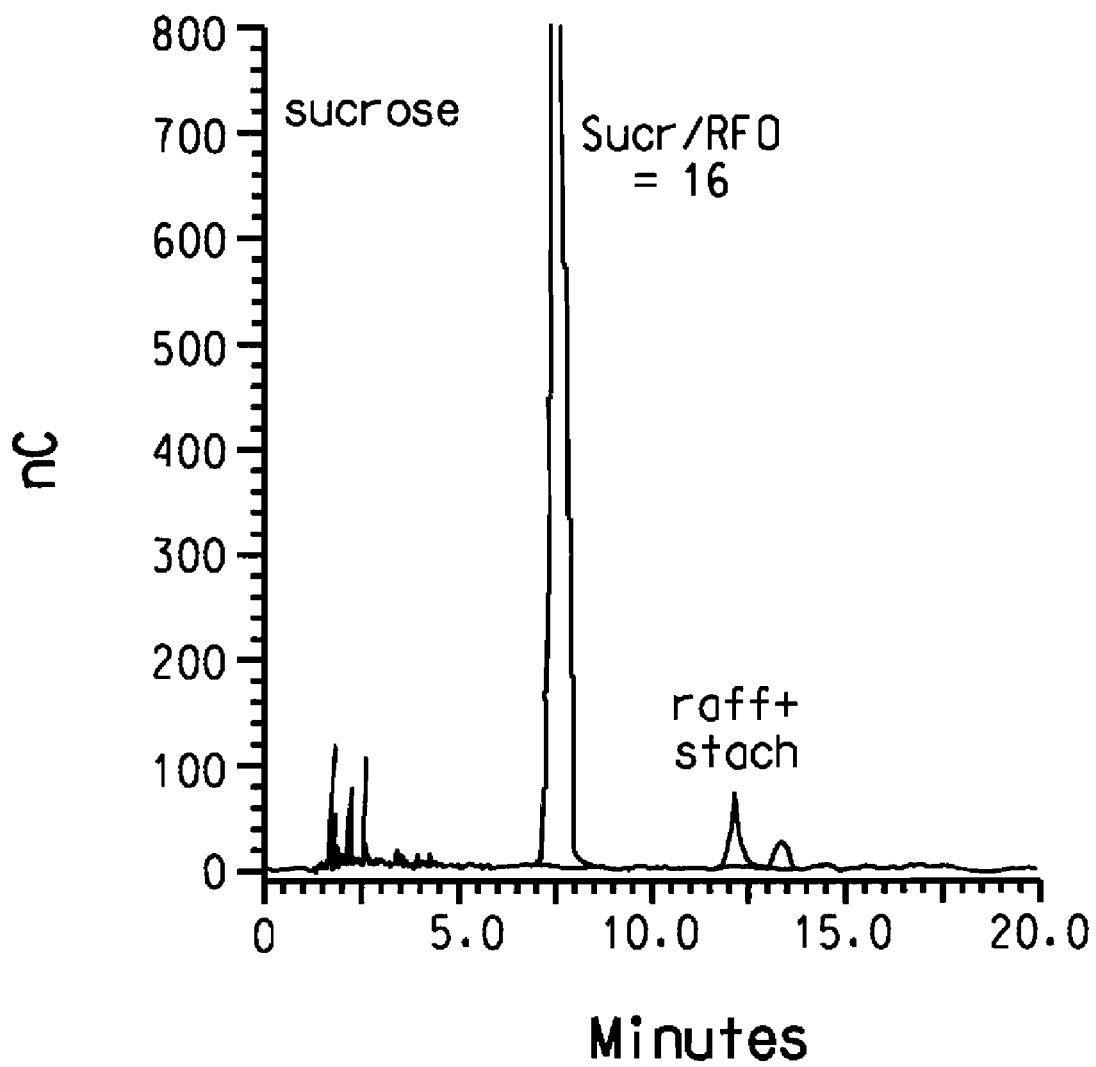
FIG. 10 shows the carbohydrate profiles of a mutant and a transgenic low raffinose saccharide soybean compared to wild type soybean.
Figure 10B:
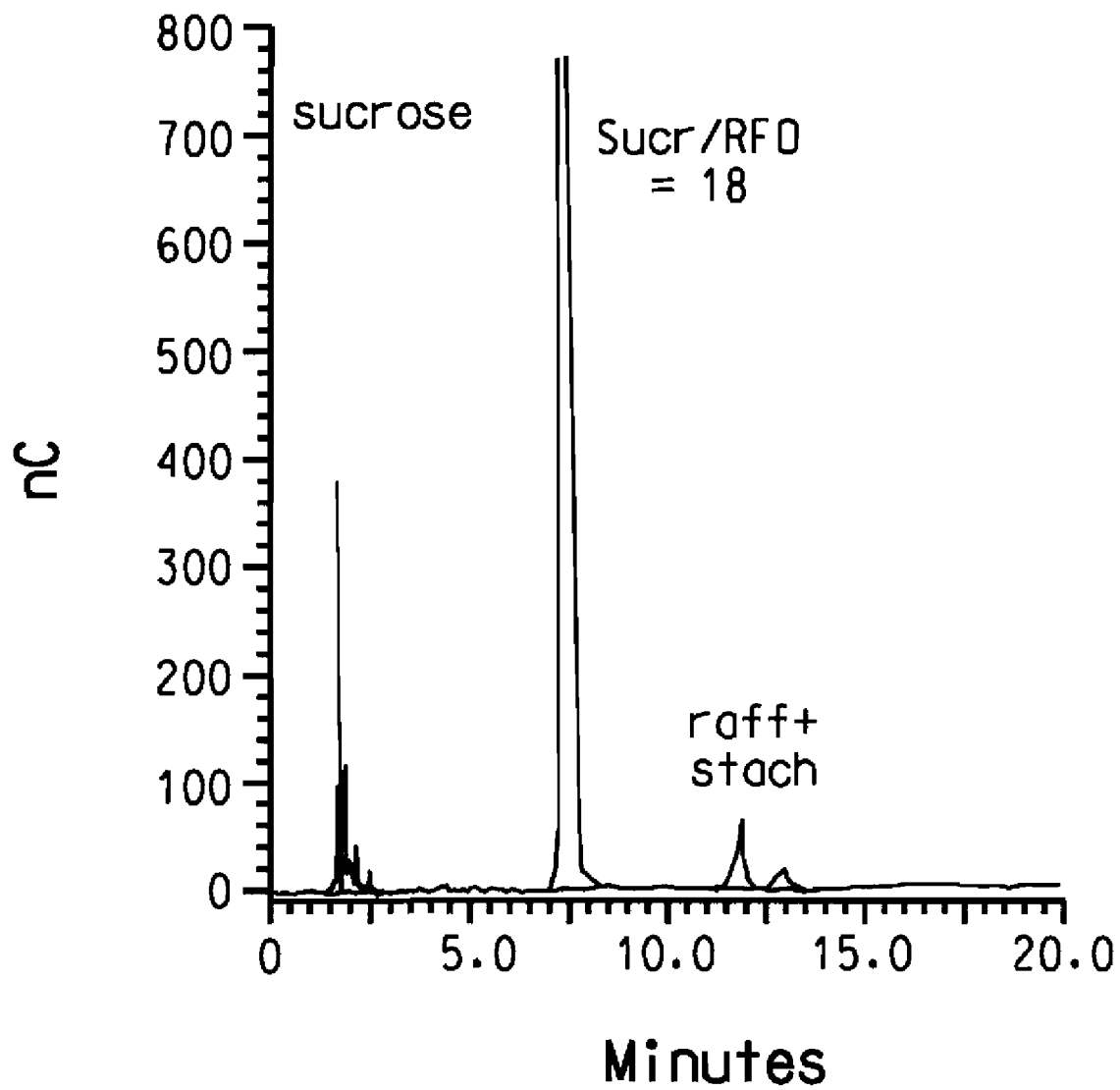
Figure 10C:
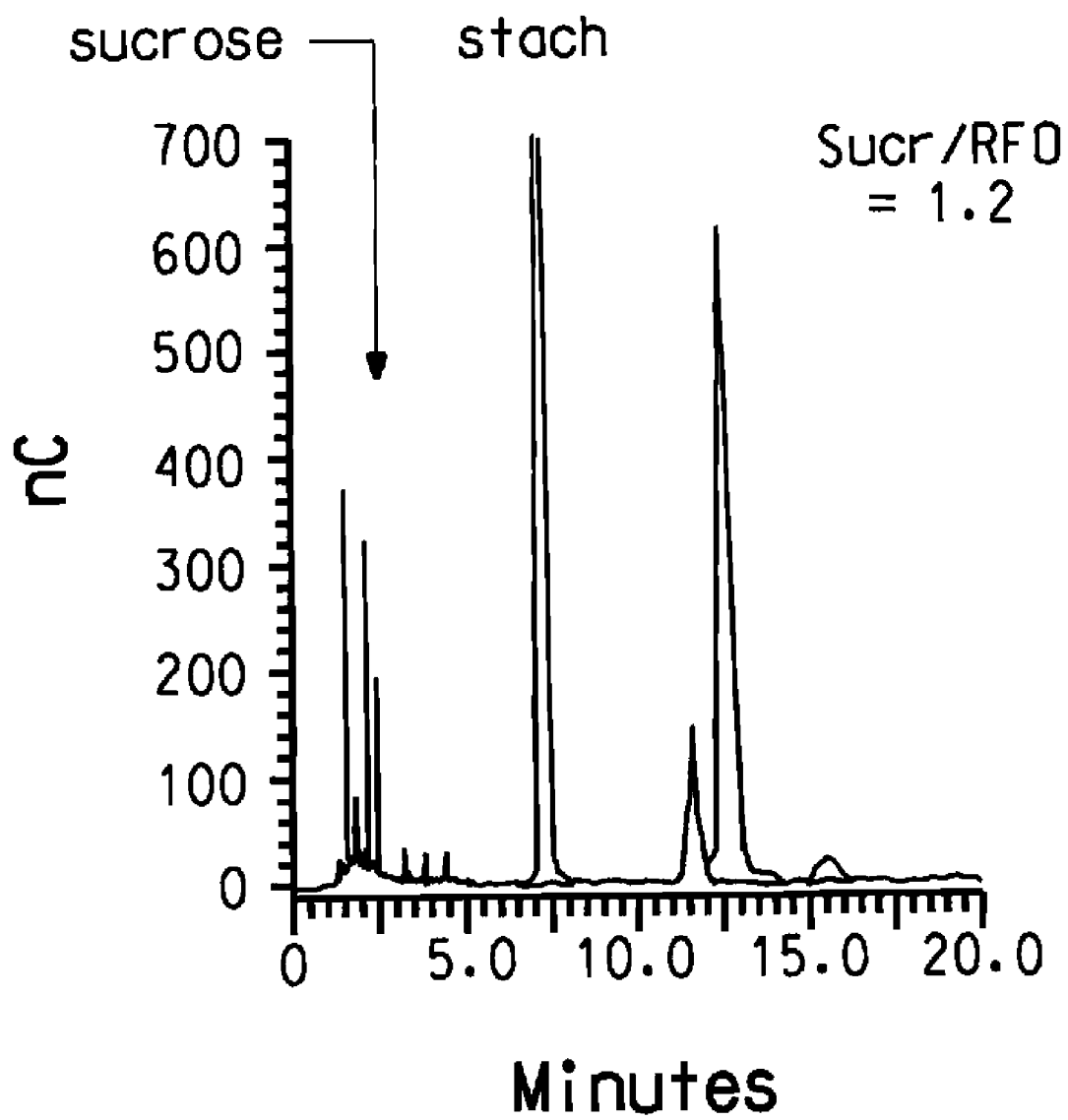

A typical profile of a soybean mutant characterized by highly reduced raffinose family oligosaccharides content (Hitz et al. 2002. Plant Physiology Vol 128, pp 650-660) is shown in FIG. 10 (Mutant HE2, left). As a comparison, the carbohydrate profile of soybeans transformed with SH50 as described in Example 12 is shown on the right (Transgenic seed with HE2 phenotype). Furthermore, the sucrose to RFO ratio of the transgenic and mutant was very similar and more than 10 fold higher when compared to wild type. The % decrease in RFO when compared to wild type of some transgenic seeds are shown in Table 6 and indicate a % reduction ranging from 71% to 89%. In comparison, the percent reduction of the mutant was 85%.

TABLE 6

Sucrose to RFO ratio and % decrease in RFO of transgenic soybean seeds (transformed with SH50) when compared with Jack wild type. The % reduction in RFO of a known mutant is included as a reference.

| | A | U | V |
|---|---|---|---|
| 1 | Event | S/RFO ratio | % decrease in RFO |
| 2 | AFS4042-5-1-1, seed 1 | 6.8 | 71 |
| 3 | AFS4042-5-1-1, seed 5 | 15.9 | 87 |
| 4 | AFS4042-5-1-1, seed 7 | 11.2 | 82 |
| 5 | AFS4042-5-1-1, seed 12 | 12.7 | 85 |
| 6 | AFS4042-5-1-1, seed 18 | 17.8 | 89 |
| 7 | AFS4042-5-1-1, seed 20 | 12.5 | 82 |
| 8 | AFS4042-5-1-3, seed 7 | 16.3 | 87 |
| 9 | AFS4042-5-1-4, seed 2 | 14.6 | 85 |
| 10 | AFS4042-5-1-4, seed 7 | 10.5 | 80 |
| 11 | | | |
| 12 | Jack-wild type | | 0 |
| 14 | Low RFO mutant | | 85 |

Example 13

Construction of Galactinol Synthase Silencing Plasmids Driven by β-Conglycinin and KTI3

Plasmid pJMS10 (FIG. 3) was prepared as described in Example 6.

Figure 11:
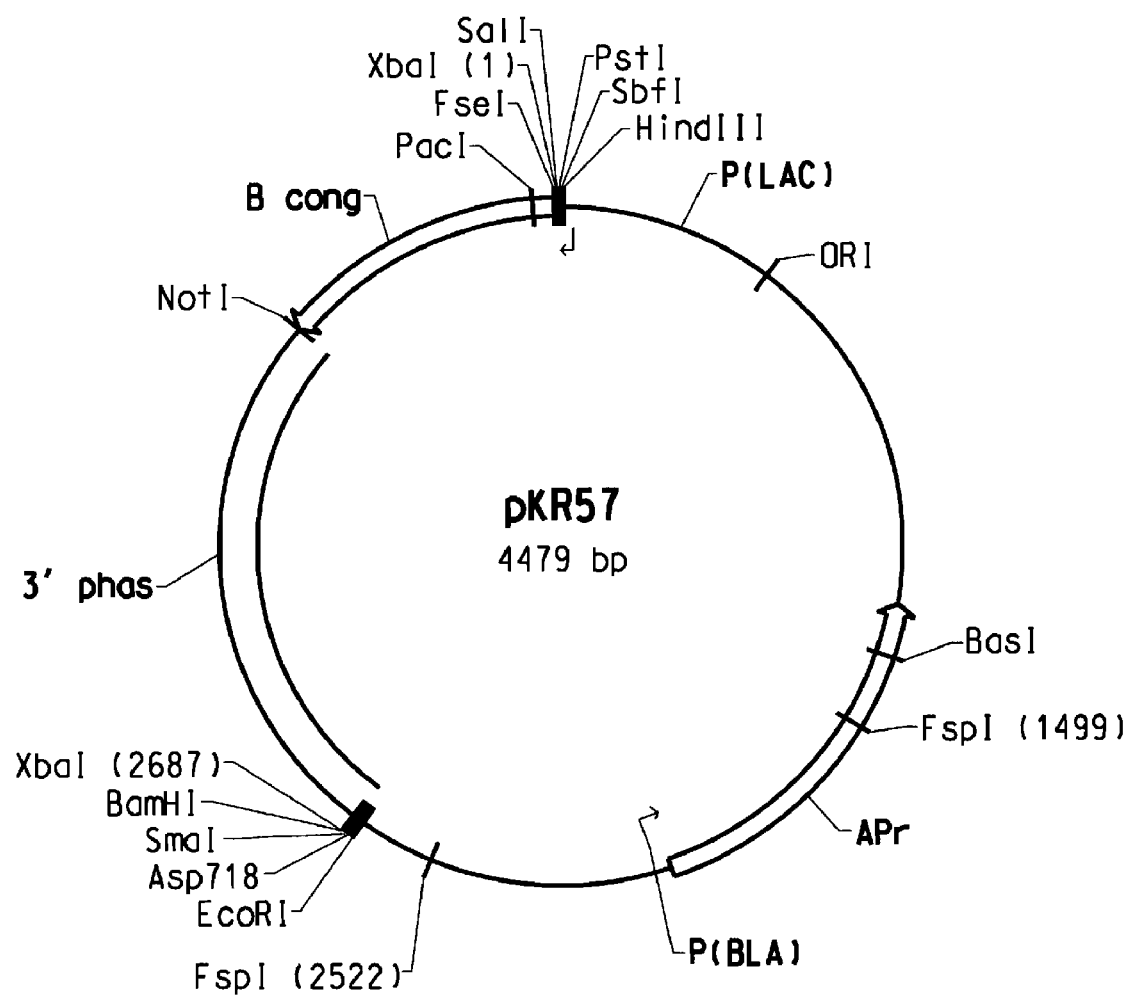
FIG. 11 shows vector pKR57.
Figure 12:
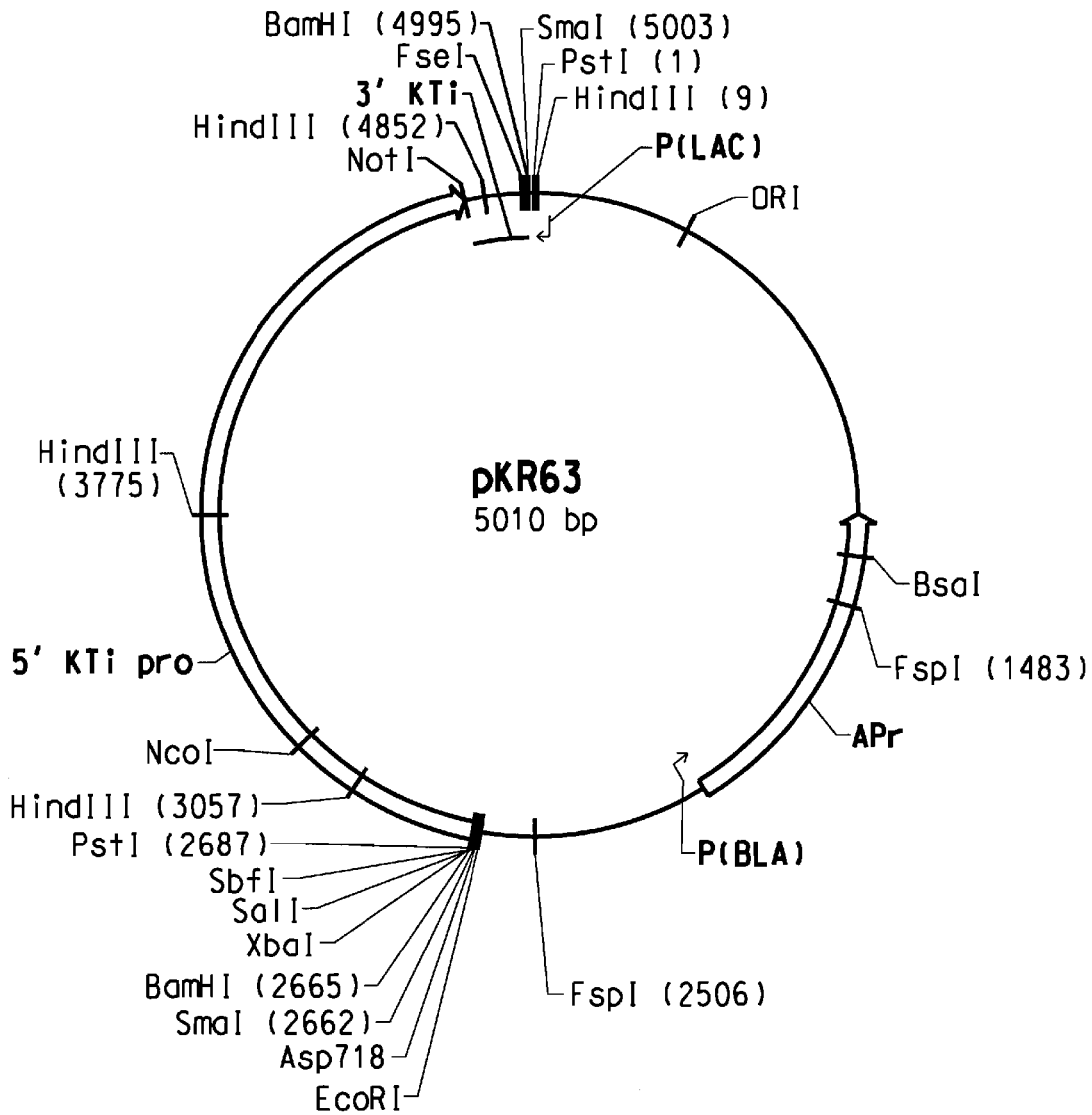
FIG. 12 shows vector pKR63.
Figure 13:
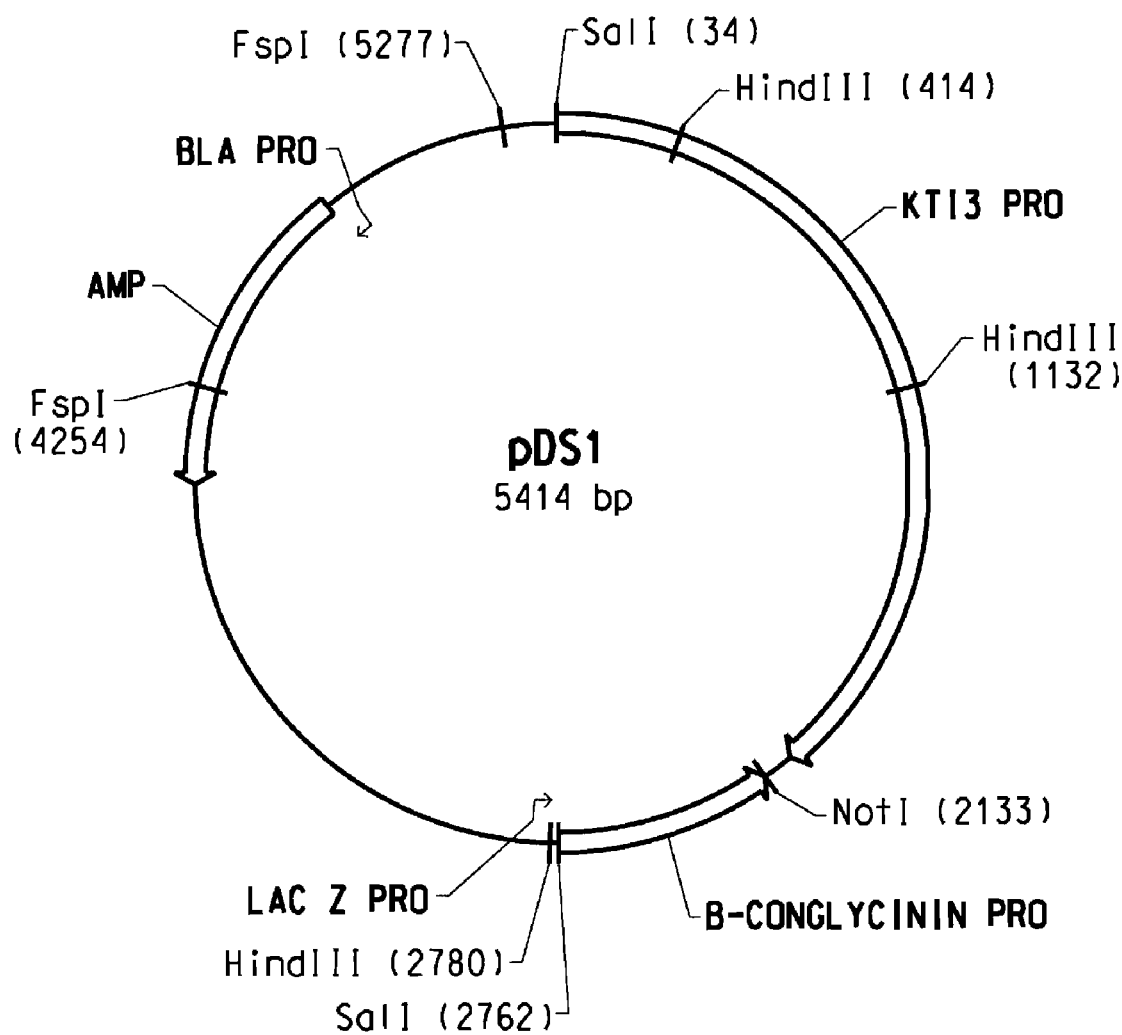
FIG. 13 shows vector pDS1.
Figure 14:
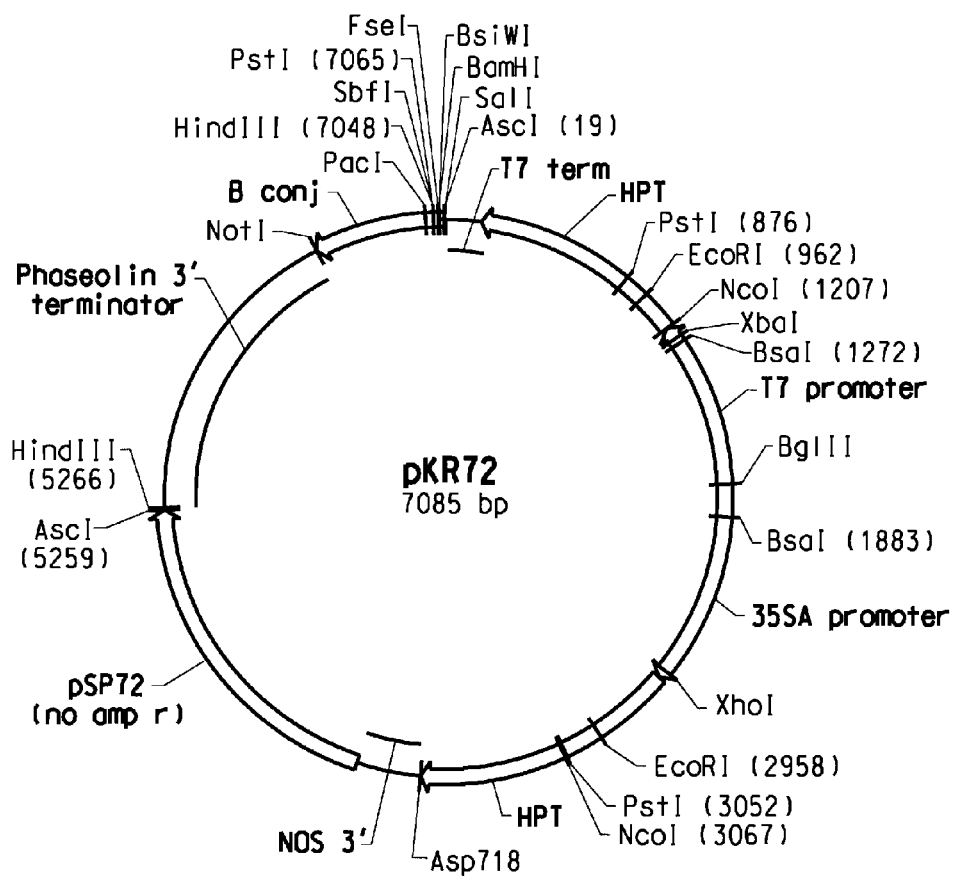
FIG. 14 shows vector pKR72.
Figure 15:
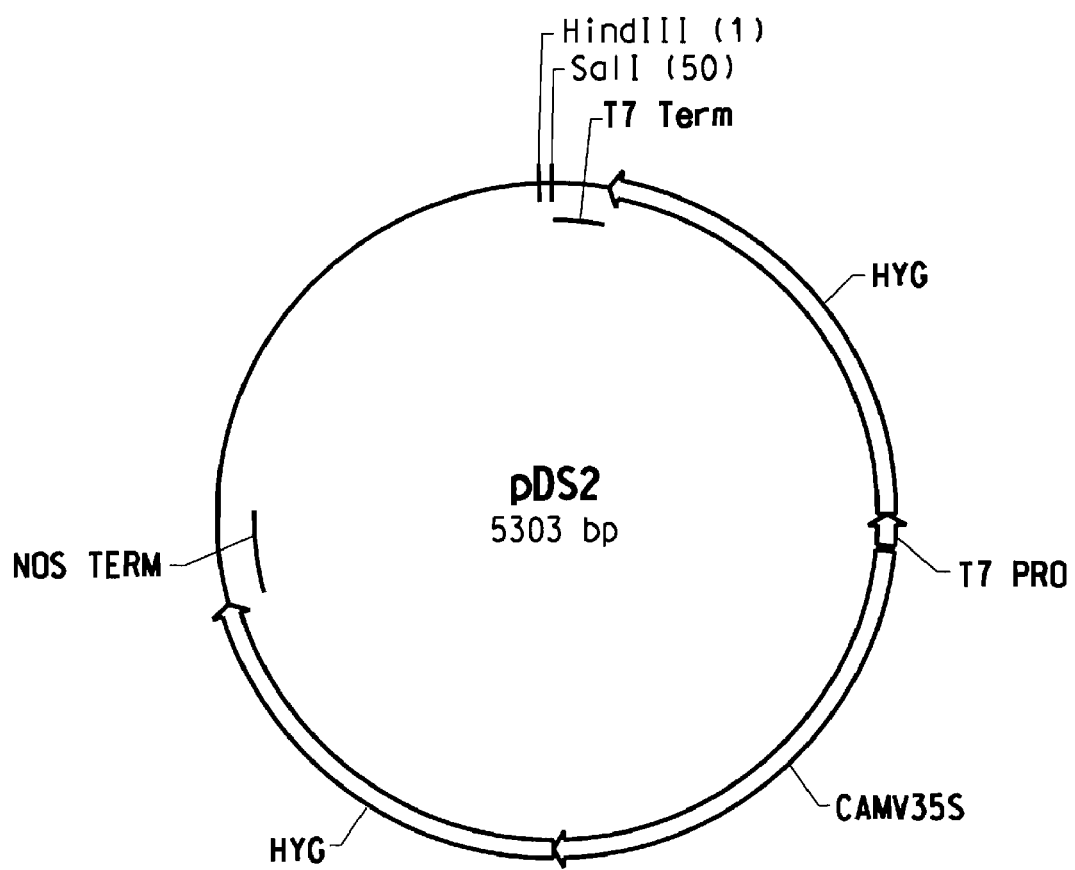
FIG. 15 shows vector pDS2.
Figure 16:
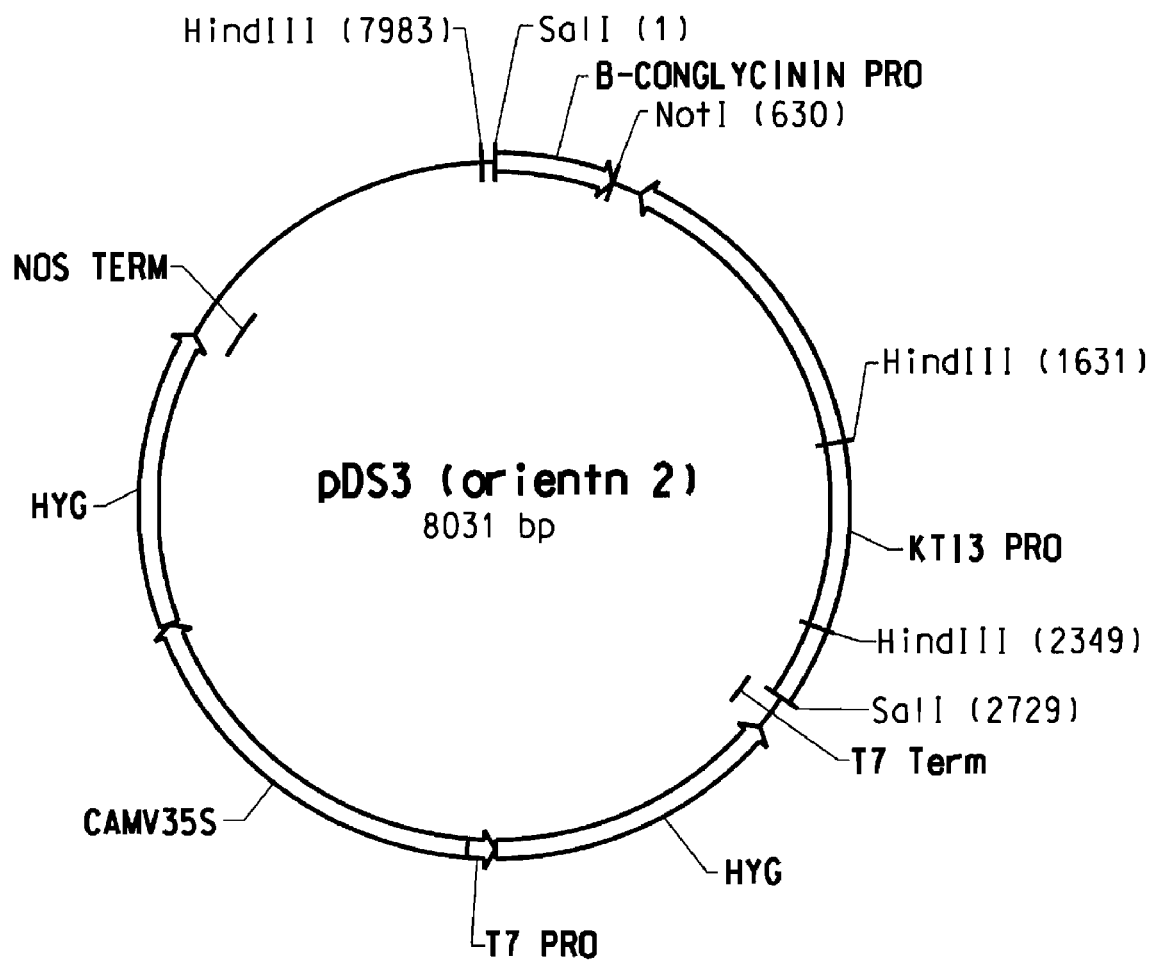
FIG. 16 shows vector pDS3 (orientation 2).

Preparation of Plasmid pDS3:

pKR57 (FIG. 11) (4479 bp; SEQ ID NO:30) was digested with Eco RI and Not I, run on a 0.8% Tris-Acetate-Ethylene-diaminetetraacetic acid-agarose gel (TAE-agarose gel) and a 3144 bp fragment containing the β-conglycinin promoter, an origin of replication and a gene encoding ampicillin resistance was purified using the Qiagen gel extraction kit. pKR63 (FIG. 12) (5010 bp; SEQ ID NO:31) was digested with Eco RI and Not I, run on a 0.8% TAE-agarose gel and a 2270 bp fragment containing the KTi promoter was purified using the Qiagen gel extraction kit. The isolated fragments were ligated together and the ligation was transformed into *E. coli* and colonies were selected on ampicillin. Bacterial colonies were selected and grown overnight in LB media and appropriate antibiotic selection. DNA was isolated from the resulting culture using a Qiagen miniprep kit according to the manufacturer's protocol and then analyzed by restriction digest. The resulting plasmid was named pDS1 (FIG. 13) (5414 bp; SEQ ID NO:32).

pKR72 (FIG. 14) (7085 bp; SEQ ID NO:33) was digested with Hind III, run on a 0.8% TAE-agarose gel and a 5303 bp fragment containing a gene that encodes resistance to hygromycin operably linked to a prokaryotic promoter and a gene that encodes resistance to hygromycin operably linked to a eukaryotic promoter were purified using the Qiagen gel extraction kit. The fragment was ligated to itself and the ligation was transformed into *E. coli* and colonies were selected on hygromycin. Bacterial colonies were selected and grown overnight in LB media and appropriate antibiotic selection. DNA was isolated from the resulting culture using a Qiagen miniprep kit according to the manufacturer's protocol and then analyzed by restriction digest. The resulting plasmid was named pDS2 (FIG. 15) (5303 bp; SEQ ID NO:34).

pDS2 was digested with Sal I and the ends were dephosphorylated with calf intestinal alkaline phosphatase (CIAP) according to the manufacture's instructions (Stratagene, San Diego, Calif.). pDS1 was digested with Sal I and Fsp I, run on a 0.8% TAE-agarose gel and a 2728 bp fragment containing the KTi3 promoter and the β-conglycinin promoter in opposite orientations was purified using the Qiagen gel extraction kit. The isolated fragments were ligated together and the ligation was transformed into *E. coli* and colonies were selected on hygromycin. Bacterial colonies were selected and grown overnight in LB media and appropriate antibiotic selection. DNA was isolated from the resulting culture using a Qiagen miniprep kit according to the manufacturer's protocol and then analyzed by restriction digest. The resulting plasmids were named pDS3 [orientation 2 (FIG. 16, SEQ ID NO: 35)].

Figure 17:
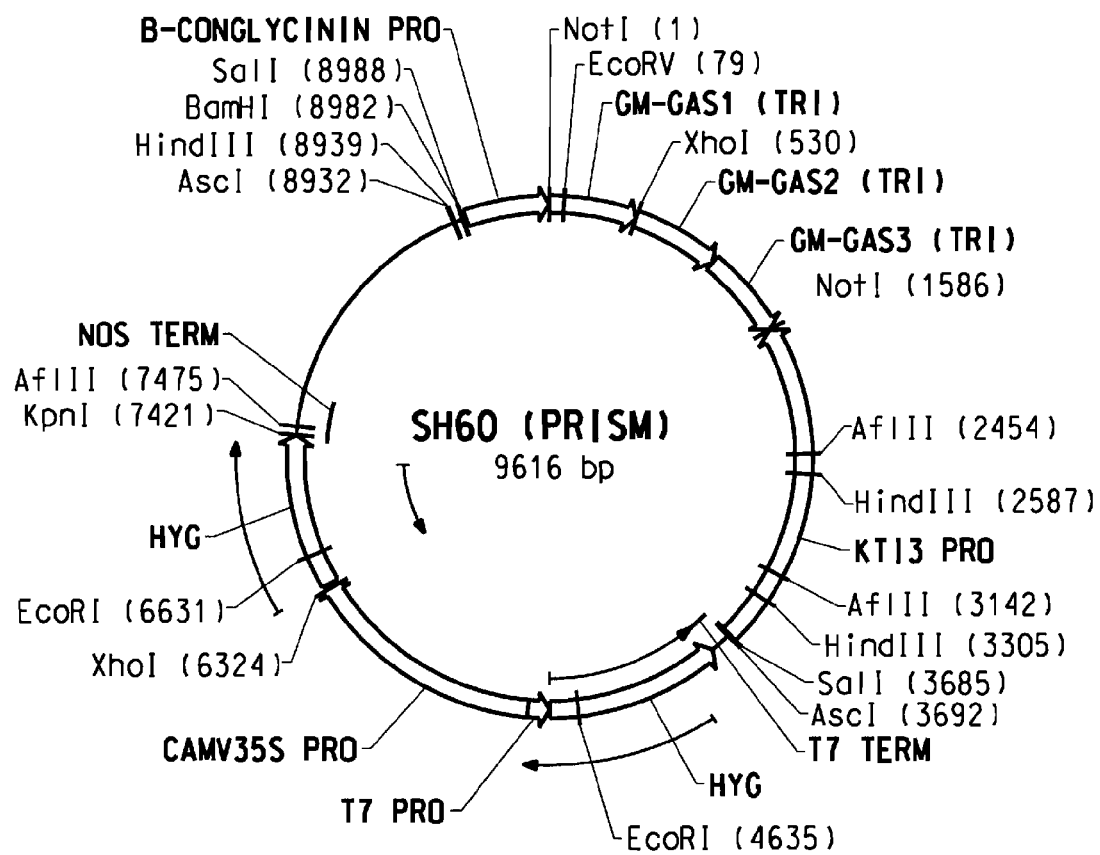
FIG. 17 shows vector SH60.

Preparation of SH60:

pJMS10 (FIG. 3) was digested with Not1, run on a 0.8% TAE-agarose gel and a 1585 bp DNA fragment (SEQ ID NO:37) comprising the partial sequences of GAS1 (SEQ ID NO:14), GAS2 (SEQ ID NO:17) and GAS3 (SEQ ID NO:20) was purified using the Qiagen gel extraction kit. pDS3 (orientation 2) (FIG. 16, SEQ ID NO: 35) was digested with Not1, run on a 0.8% TAE-agarose gel and a 8031 bp DNA fragment was purified using the Qiagen gel extraction kit. The isolated fragments were ligated together and the ligation was transformed into *E. coli* and colonies were selected on hygromycin. Bacterial colonies were selected and grown overnight in LB media and appropriate antibiotic selection. DNA was isolated from the resulting culture using a Qiagen miniprep kit according to the manufacturer's protocol and then analyzed by restriction digest. The resulting plasmid was named SH60 (FIG. 17, SEQ ID NO: 36).

Example 14

Figure 18:
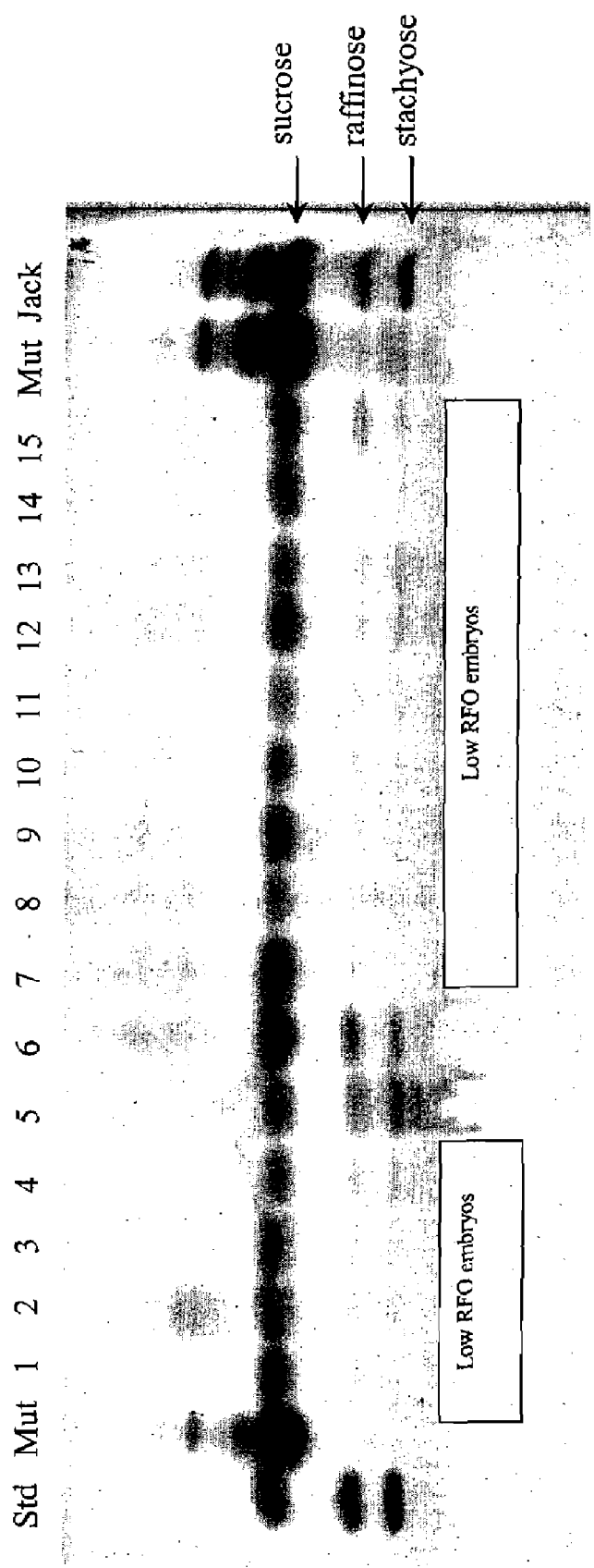
FIG. 18 shows a TLC analysis of somatic embryos containing the beta-conglycinin/KTI3 driven recombinant expression construct described in Example 13.

Reduction of Raffinose Family Oligosaccharide (RFO) in Transgenic Soybean Somatic Embryos SH60, as described in Example 13, was transformed into soybean embryogenic suspension cultures using a protocol as described in Example 8 above. Individual immature soybean embryos were dried-down (by transferring them into an empty small petridish that was seated on top of a 10 cm petridish containing some agar gel to allow slow dry down) to mimic the last stages of soybean seed development. Dried-down embryos are capable of producing plants when transferred to soil or soil-less media. Storage products produced by embryos at this stage are similar in composition to storage products produced by zygotic embryos at a similar stage of development and most importantly the storage product profile is predictive of plants derived from a somatic embryo line (PCT Publication No. WO 94/11516, which published on May 26, 1994). Raffinose Family Oligosaccharides (raffinose, stachyose) of transgenic somatic embryos containing the B-conglycinin/KTI3 driven (SH60) recombinant expression construct described in Example 13 was measured by thin layer chromatography. Somatic embryos were extracted with hexane then dried. The dried material was re-suspended in 80% methanol, incubated at room temperature for 1-2 hours, centrifuged, and 2 μl of the supernatant is spotted onto a TLC plate (Kieselgel 60 CF, from EM Scientific, Gibbstown, N.J.; Catalog No. 13749-6). The TLC was run methylacetate: isopropanol:20% acetic acid (3:4:4) for 1-1.5 hours. The air dried plates were sprayed with 2% sulfuric acid and heated until the charred sugars were detected. As shown in FIG. 18 the embryos labeled "Low RFO embryos" show reduced levels of raffinose sugars (raffinose and stachyose s) when compared to a to wild-type soybean. Five out of eleven (45%) lines analyzed showed reduced levels of RFOs, which is demonstrative of reduced galactinol synthase expression (see Table 7).

TABLE 7

Positive Transformed Lines with Reduced Galactinol Synthase Expression

|  | carbohydrate phenotype |
| --- | --- |
| GAS1GAS2GAS3 lines with wild type RFO levels | 6 out of 11 |
| GAS1GAS2GAS3 lines with reduced RFO levels | 5 out of 11 |
| Percent gene silencing | 45% |

What is claimed is:

1. An isolated polynucleotide comprising:
   (a) a nucleotide sequence encoding a polypeptide having galactinol synthase activity, wherein the polypeptide has an amino acid sequence of at least 95% identity when compared to SEQ ID NO: 4, or
   (b) a fragment of the nulcleotide sequence in (a) that functions to co-suppress endogenous nucleic acid sequences encoding polypeptides having galactinol synthase activity.

2. The polynucleotide of claim 1, wherein the amino acid sequence of the polypeptide comprises SEQ ID NO:4.

3. The polynucleotide of claim 1, wherein the nucleotide sequence comprises SEQ ID NO:3.

4. A vector comprising the polynucleotide of claim 1.

5. A recombinant DNA construct comprising the polynucleotide of claim 1 operably linked to at least one regulatory sequence.

6. A method for transforming a cell, said method comprising transforming a cell with the polynucleotide of claim 1.

7. A cell comprising the recombinant DNA construct of claim 5.

8. A method for producing a plant, said method comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

UNITED STATES PATENT AND TRADEMARK OFFICE
CERTIFICATE OF CORRECTION

PATENT NO. : 7,476,778 B2 Page 1 of 1
APPLICATION NO. : 11/928675
DATED : January 13, 2009
INVENTOR(S) : Johan M. Stoop et al.

It is certified that error appears in the above-identified patent and that said Letters Patent is hereby corrected as shown below:

Title Page item 75
Please add inventor Stephen M. Allen

Signed and Sealed this

First Day of June, 2010

David J. Kappos
*Director of the United States Patent and Trademark Office*

SEQUENCE LISTING

<160> NUMBER OF SEQ ID NOS: 37

<210> SEQ ID NO 1
<211> LENGTH: 1151
<212> TYPE: DNA
<213> ORGANISM: Glycine max
<220> FEATURE:
<221> NAME/KEY: CDS
<222> LOCATION: (71)...(1090)

<400> SEQUENCE: 1

```
ctaagctctc ttttagtctt actcacaaac acttttttca ctgcttccat tacgaacata      60
tatttattat atg gct cct gaa ctt gtc ccc acc gtt gtg aaa tcc agt        109
           Met Ala Pro Glu Leu Val Pro Thr Val Val Lys Ser Ser
           1               5                   10 gct gcg ttc acg aaa ccc gcg acc ctt cca agg cgt gcc tac gtg aca        157
Ala Ala Phe Thr Lys Pro Ala Thr Leu Pro Arg Arg Ala Tyr Val Thr
15                  20                  25 ttc ctc gcc gga aac ggt gac tac gtg aaa ggg gtg gtt ggc ctc gcc        205
Phe Leu Ala Gly Asn Gly Asp Tyr Val Lys Gly Val Val Gly Leu Ala
30                  35                  40                  45 aaa ggg ttg cga aag gtg aaa acc gcg tac ccg ttg gtg gtg gct gtc        253
Lys Gly Leu Arg Lys Val Lys Thr Ala Tyr Pro Leu Val Val Ala Val
50                  55                  60 ctc ccc gat gtg ccg gag gag cac cgt aag atc ctg gag tct cag ggc        301
Leu Pro Asp Val Pro Glu Glu His Arg Lys Ile Leu Glu Ser Gln Gly
65                  70                  75 tgc atc gtt cgc gag atc gaa ccc gtt tac cca ccc gaa aac caa acc        349
Cys Ile Val Arg Glu Ile Glu Pro Val Tyr Pro Pro Glu Asn Gln Thr
80                  85                  90 cag ttt gcc atg gct tat tac gtc atc aac tac tcc aag ctc cgt ata        397
Gln Phe Ala Met Ala Tyr Tyr Val Ile Asn Tyr Ser Lys Leu Arg Ile
95                  100                 105 tgg gag ttt gtg gag tac agc aag atg ata tac ttg gac gga gac att        445
Trp Glu Phe Val Glu Tyr Ser Lys Met Ile Tyr Leu Asp Gly Asp Ile
110                 115                 120                 125 gag gta tat gag aac ata gac cac cta ttt gac cta cct gat ggt aac        493
Glu Val Tyr Glu Asn Ile Asp His Leu Phe Asp Leu Pro Asp Gly Asn
130                 135                 140 ttt tac gct gtg atg gat tgt ttc tgc gag aag aca tgg agt cac acc        541
Phe Tyr Ala Val Met Asp Cys Phe Cys Glu Lys Thr Trp Ser His Thr
145                 150                 155 cct cag tac aag gtg ggt tac tgc cag caa tgc ccg gag aag gtg cgg        589
Pro Gln Tyr Lys Val Gly Tyr Cys Gln Gln Cys Pro Glu Lys Val Arg
160                 165                 170 tgg ccc acc gaa ttg ggt cag ccc cct tct ctt tac ttc aac gct ggc        637
Trp Pro Thr Glu Leu Gly Gln Pro Pro Ser Leu Tyr Phe Asn Ala Gly
175                 180                 185 atg ttc gtg ttc gaa ccc aac atc gcc acc tat cat gac cta ttg aaa        685
Met Phe Val Phe Glu Pro Asn Ile Ala Thr Tyr His Asp Leu Leu Lys
190                 195                 200                 205 acg gtg caa gtc acc act ccc acc tcg ttc gct gaa caa gat ttc ttg        733
Thr Val Gln Val Thr Thr Pro Thr Ser Phe Ala Glu Gln Asp Phe Leu
210                 215                 220 aac atg tac ttc aag gac att tac aag cca atc cct tta aat tac aat        781
Asn Met Tyr Phe Lys Asp Ile Tyr Lys Pro Ile Pro Leu Asn Tyr Asn
225                 230                 235 ctt gtc ctc gcc atg ctg tgg cgc cac ccg gaa aac gtt aaa tta gac        829
Leu Val Leu Ala Met Leu Trp Arg His Pro Glu Asn Val Lys Leu Asp
```

```
                240                 245                 250
caa gtc aag gtt gtt cac tat tgc gca gcg ggg tcc aag cca tgg aga      877
Gln Val Lys Val Val His Tyr Cys Ala Ala Gly Ser Lys Pro Trp Arg
255                 260                 265 tat acg ggg aag gaa gag aat atg cag agg gag gac ata aag atg ctg      925
Tyr Thr Gly Lys Glu Glu Asn Met Gln Arg Glu Asp Ile Lys Met Leu
270                 275                 280                 285 gtg aag aaa tgg tgg gat atc tac aat gat gct tcg ctt gac tac aag      973
Val Lys Lys Trp Trp Asp Ile Tyr Asn Asp Ala Ser Leu Asp Tyr Lys
290                 295                 300 cca ttg atg aat gca agt gaa gct cca gca gcg gat ggt gtt gac att     1021
Pro Leu Met Asn Ala Ser Glu Ala Pro Ala Ala Asp Gly Val Asp Ile
305                 310                 315 gaa caa ttc gtg cag gct cta tca gag gtt ggt cat gtt caa tat gtc     1069
Glu Gln Phe Val Gln Ala Leu Ser Glu Val Gly His Val Gln Tyr Val
320                 325                 330 acc gcg cct tca gca gct taa ttaagagggc acattcaaat cacgacaaaa        1120
Thr Ala Pro Ser Ala Ala
335 aacaaccaag tgaaaaaaaa aaaaaaaaaa a                                   1151

<210> SEQ ID NO 2
<211> LENGTH: 339
<212> TYPE: PRT
<213> ORGANISM: Glycine max

<400> SEQUENCE: 2

Met Ala Pro Glu Leu Val Pro Thr Val Val Lys Ser Ser Ala Ala Phe
1               5                   10                  15

Thr Lys Pro Ala Thr Leu Pro Arg Arg Ala Tyr Val Thr Phe Leu Ala
            20                  25                  30

Gly Asn Gly Asp Tyr Val Lys Gly Val Val Gly Leu Ala Lys Gly Leu
        35                  40                  45

Arg Lys Val Lys Thr Ala Tyr Pro Leu Val Val Ala Val Leu Pro Asp
    50                  55                  60

Val Pro Glu Glu His Arg Lys Ile Leu Glu Ser Gln Gly Cys Ile Val
65                  70                  75                  80

Arg Glu Ile Glu Pro Val Tyr Pro Pro Glu Asn Gln Thr Gln Phe Ala
                85                  90                  95

Met Ala Tyr Tyr Val Ile Asn Tyr Ser Lys Leu Arg Ile Trp Glu Phe
            100                 105                 110

Val Glu Tyr Ser Lys Met Ile Tyr Leu Asp Gly Asp Ile Glu Val Tyr
        115                 120                 125

Glu Asn Ile Asp His Leu Phe Asp Leu Pro Asp Gly Asn Phe Tyr Ala
    130                 135                 140

Val Met Asp Cys Phe Cys Glu Lys Thr Trp Ser His Thr Pro Gln Tyr
145                 150                 155                 160

Lys Val Gly Tyr Cys Gln Gln Cys Pro Glu Lys Val Arg Trp Pro Thr
                165                 170                 175

Glu Leu Gly Gln Pro Pro Ser Leu Tyr Phe Asn Ala Gly Met Phe Val
            180                 185                 190

Phe Glu Pro Asn Ile Ala Thr Tyr His Asp Leu Leu Lys Thr Val Gln
        195                 200                 205

Val Thr Thr Pro Thr Ser Phe Ala Glu Gln Asp Phe Leu Asn Met Tyr
    210                 215                 220

Phe Lys Asp Ile Tyr Lys Pro Ile Pro Leu Asn Tyr Asn Leu Val Leu
```

```
                  225                 230                 235                 240
Ala Met Leu Trp Arg His Pro Glu Asn Val Lys Leu Asp Gln Val Lys
            245                 250                 255

Val Val His Tyr Cys Ala Ala Gly Ser Lys Pro Trp Arg Tyr Thr Gly
    260                 265                 270

Lys Glu Glu Asn Met Gln Arg Glu Asp Ile Lys Met Leu Val Lys Lys
275                 280                 285

Trp Trp Asp Ile Tyr Asn Asp Ala Ser Leu Asp Tyr Lys Pro Leu Met
290                 295                 300

Asn Ala Ser Glu Ala Pro Ala Ala Asp Gly Val Asp Ile Glu Gln Phe
305                 310                 315                 320

Val Gln Ala Leu Ser Glu Val Gly His Val Gln Tyr Val Thr Ala Pro
325                 330                 335

Ser Ala Ala

<210> SEQ ID NO 3
<211> LENGTH: 1398
<212> TYPE: DNA
<213> ORGANISM: Glycine max
<220> FEATURE:
<221> NAME/KEY: CDS
<222> LOCATION: (94)..(1089)

<400> SEQUENCE: 3
gcacgaggtg attttttgctt aattactaaa ccaaaccatt tcttattccc tcatcgaaac    60
cttttctttc tatatatttc cctttttcaat atc atg gca cct aac atc acc acc   114
                                     Met Ala Pro Asn Ile Thr Thr
                                     1               5 gtt gtt gcc aat gcc acc act gag caa tta ccc aaa gct cat gga gga   162
Val Val Ala Asn Ala Thr Thr Glu Gln Leu Pro Lys Ala His Gly Gly
 10                  15                  20 agt agt ggg cgt gcc ttt gtg act ttt ctt gct gga aac ggt gat tat   210
Ser Ser Gly Arg Ala Phe Val Thr Phe Leu Ala Gly Asn Gly Asp Tyr
25                  30                  35 gta aag ggt gtt gtg ggt ttg gcc aaa gga ctg aga aag gcc aaa agc   258
Val Lys Gly Val Val Gly Leu Ala Lys Gly Leu Arg Lys Ala Lys Ser
40                  45                  50                  55 atg tac cct ttg gtg gtt gct gtg tta cca gat gtt cct gaa gaa cat   306
Met Tyr Pro Leu Val Val Ala Val Leu Pro Asp Val Pro Glu Glu His
                60                  65                  70 cgt gcg att ctc aaa tcc caa ggt tgc att gtc agg gag att gaa cct   354
Arg Ala Ile Leu Lys Ser Gln Gly Cys Ile Val Arg Glu Ile Glu Pro
        75                  80                  85 gtg tac cct cct aag aac cag acc cag ttc gcc atg gcc tat tat gtc   402
Val Tyr Pro Pro Lys Asn Gln Thr Gln Phe Ala Met Ala Tyr Tyr Val
    90                  95                 100 atc aat tac tcc aag cta cgt att tgg gag ttc gtg gag tac cag aag   450
Ile Asn Tyr Ser Lys Leu Arg Ile Trp Glu Phe Val Glu Tyr Gln Lys
105                 110                 115 atg ata tac cta gac ggc gac atc caa gtt ttt gga aac att gac cac   498
Met Ile Tyr Leu Asp Gly Asp Ile Gln Val Phe Gly Asn Ile Asp His
120                 125                 130                 135 ttg ttt gat ctt cct aat aat tat ttc tat gcg gtg atg gat tgt ttc   546
Leu Phe Asp Leu Pro Asn Asn Tyr Phe Tyr Ala Val Met Asp Cys Phe
        140                 145                 150 tgc gag aag act tgg agc cac acc cct cag ttc cag att ggg tac tgc   594
Cys Glu Lys Thr Trp Ser His Thr Pro Gln Phe Gln Ile Gly Tyr Cys
    155                 160                 165
```

```
caa cag tgc cct gat aag gtt caa tgg ccc tct cac ttt ggt acc aaa    642
Gln Gln Cys Pro Asp Lys Val Gln Trp Pro Ser His Phe Gly Thr Lys
170             175                 180 cct cct cta tat ttc aat gct ggc atg ttt gtt tat gag cct aat ctc    690
Pro Pro Leu Tyr Phe Asn Ala Gly Met Phe Val Tyr Glu Pro Asn Leu
185             190                 195 aac acc tac cgt cat ctt ctc caa act gtc caa gtc atc aag ccc acg    738
Asn Thr Tyr Arg His Leu Leu Gln Thr Val Gln Val Ile Lys Pro Thr
200             205                 210                 215 tcc ttt gct gag cag gac ttt ctg aac atg tac ttc aag gac aag tac    786
Ser Phe Ala Glu Gln Asp Phe Leu Asn Met Tyr Phe Lys Asp Lys Tyr
220             225                 230 aag cca ata ccg aac gtg tac aac ctt gtg ctg gcc atg ttg tgg cgt    834
Lys Pro Ile Pro Asn Val Tyr Asn Leu Val Leu Ala Met Leu Trp Arg
235             240                 245 cac cct gag aat gtt gaa ctt gat caa gtt caa gtg gtt cat tac tgt    882
His Pro Glu Asn Val Glu Leu Asp Gln Val Gln Val Val His Tyr Cys
250             255                 260 gct gct ggg tct aag cct tgg agg ttc act ggg aag gaa gag aac atg    930
Ala Ala Gly Ser Lys Pro Trp Arg Phe Thr Gly Lys Glu Glu Asn Met
265             270                 275 gat agg gaa gat atc aag atg ctt atg aag aag tgg tgg gac ata tat    978
Asp Arg Glu Asp Ile Lys Met Leu Met Lys Lys Trp Trp Asp Ile Tyr
280             285                 290                 295 gaa gat gag aca ctg gac tac aat aac aac tct gtc aat gtg gaa cgt   1026
Glu Asp Glu Thr Leu Asp Tyr Asn Asn Asn Ser Val Asn Val Glu Arg
300             305                 310 ttc aca tca gta cta ttg gat gct ggg ggt ttt cag ttt gtg cca gca   1074
Phe Thr Ser Val Leu Leu Asp Ala Gly Gly Phe Gln Phe Val Pro Ala
315             320                 325 cct tct gct gcc taa tatgattcac agctacaaat taaagtctaa ttaacgacaa   1129
Pro Ser Ala Ala
330 agtatatatg tattgttatt tgtttttgtt ttttttttcg tttttgggtc ttatgaacga   1189 accacgtcta tagttttaat ttggatgacc ttttttgtata caaagtcaca tgtgacgtct   1249 tacagctttt gattattatt aagatttaat tatatgagtc ctttacttaa tttgttttca   1309 ttgatcaaga gttgtggata tatatatata tatatatata tctttaatttt tattaaatga   1369 aattttaagg caaaaaaaaa aaaaaaaaa                                   1398

<210> SEQ ID NO 4
<211> LENGTH: 331
<212> TYPE: PRT
<213> ORGANISM: Glycine max

<400> SEQUENCE: 4

Met Ala Pro Asn Ile Thr Thr Val Val Ala Asn Ala Thr Thr Glu Gln
1               5                   10                  15

Leu Pro Lys Ala His Gly Gly Ser Ser Gly Arg Ala Phe Val Thr Phe
            20                  25                  30

Leu Ala Gly Asn Gly Asp Tyr Val Lys Gly Val Val Gly Leu Ala Lys
        35                  40                  45

Gly Leu Arg Lys Ala Lys Ser Met Tyr Pro Leu Val Val Ala Val Leu
    50                  55                  60

Pro Asp Val Pro Glu Glu His Arg Ala Ile Leu Lys Ser Gln Gly Cys
65              70                  75                  80

Ile Val Arg Glu Ile Glu Pro Val Tyr Pro Pro Lys Asn Gln Thr Gln
            85                  90                  95
```

-continued

```
Phe Ala Met Ala Tyr Tyr Val Ile Asn Tyr Ser Lys Leu Arg Ile Trp
100                 105                 110

Glu Phe Val Glu Tyr Gln Lys Met Ile Tyr Leu Asp Gly Asp Ile Gln
115                 120                 125

Val Phe Gly Asn Ile Asp His Leu Phe Asp Leu Pro Asn Asn Tyr Phe
130                 135                 140

Tyr Ala Val Met Asp Cys Phe Cys Glu Lys Thr Trp Ser His Thr Pro
145                 150                 155                 160

Gln Phe Gln Ile Gly Tyr Cys Gln Gln Cys Pro Asp Lys Val Gln Trp
165                 170                 175

Pro Ser His Phe Gly Thr Lys Pro Pro Leu Tyr Phe Asn Ala Gly Met
180                 185                 190

Phe Val Tyr Glu Pro Asn Leu Asn Thr Tyr Arg His Leu Leu Gln Thr
195                 200                 205

Val Gln Val Ile Lys Pro Thr Ser Phe Ala Glu Gln Asp Phe Leu Asn
210                 215                 220

Met Tyr Phe Lys Asp Lys Tyr Lys Pro Ile Pro Asn Val Tyr Asn Leu
225                 230                 235                 240

Val Leu Ala Met Leu Trp Arg His Pro Glu Asn Val Glu Leu Asp Gln
245                 250                 255

Val Gln Val Val His Tyr Cys Ala Ala Gly Ser Lys Pro Trp Arg Phe
260                 265                 270

Thr Gly Lys Glu Glu Asn Met Asp Arg Glu Asp Ile Lys Met Leu Met
275                 280                 285

Lys Lys Trp Trp Asp Ile Tyr Glu Asp Glu Thr Leu Asp Tyr Asn Asn
290                 295                 300

Asn Ser Val Asn Val Glu Arg Phe Thr Ser Val Leu Leu Asp Ala Gly
305                 310                 315                 320

Gly Phe Gln Phe Val Pro Ala Pro Ser Ala Ala
325                 330

<210> SEQ ID NO 5
<211> LENGTH: 1417
<212> TYPE: DNA
<213> ORGANISM: Glycine max
<220> FEATURE:
<221> NAME/KEY: CDS
<222> LOCATION: (213)..(1184)

<400> SEQUENCE: 5
ccaagatctt aaaatatctc ttccatacaa gtttgttttc aaagtgtttt tgtctcccaa      60
atcctactct tgtgaccaca agccttcact tcactctctc tctctctctc tctctctctc     120
tctctctctc tctctctttt ttgaaaccct tttttctctt ctcaaaccaa accaagcaag     180
caattatatt acactactca ctcactgaga cc atg gct cct aat atc acc acc       233
                                   Met Ala Pro Asn Ile Thr Thr
                                   1               5 gtc acc gac gct caa gcc aag gcc gcc ggc ggg cgt ggc cgt gcc tac       281
Val Thr Asp Ala Gln Ala Lys Ala Ala Gly Gly Arg Gly Arg Ala Tyr
10                  15                  20 gtc acc ttc ctc gcc gga aac ggt gac tat gtg aaa ggt gtc gtt ggc       329
Val Thr Phe Leu Ala Gly Asn Gly Asp Tyr Val Lys Gly Val Val Gly
25                  30                  35 ttg gcc aaa ggt ctg agg aag gtg aaa agc atg tac cct ctg gtg gtt       377
Leu Ala Lys Gly Leu Arg Lys Val Lys Ser Met Tyr Pro Leu Val Val
40                  45                  50                  55
```

```
gca gtg tta ccc gat gtt cca gaa cat cac cga aac att ctc acc tcc      425
Ala Val Leu Pro Asp Val Pro Glu His His Arg Asn Ile Leu Thr Ser
 60              65                  70 caa ggt tgc att gtt aga gaa att gaa ccc gtg tac cct cct gag aat      473
Gln Gly Cys Ile Val Arg Glu Ile Glu Pro Val Tyr Pro Pro Glu Asn
 75              80                  85 cag acg cag ttc gcc atg gca tat tac gtc atc aac tat tcc aag cta      521
Gln Thr Gln Phe Ala Met Ala Tyr Tyr Val Ile Asn Tyr Ser Lys Leu
 90              95                 100 cgt att tgg gag ttt gtg gag ttc agc aag atg ata tac cta gac ggt      569
Arg Ile Trp Glu Phe Val Glu Phe Ser Lys Met Ile Tyr Leu Asp Gly
105             110                 115 gat ata caa gtg ttt gac aat att gac cac ttg ttt gac ttg cct gat      617
Asp Ile Gln Val Phe Asp Asn Ile Asp His Leu Phe Asp Leu Pro Asp
120             125                 130                 135 aac tac ttt tat gcg gtg atg gac tgt ttt tgt gag ccc act tgg ggc      665
Asn Tyr Phe Tyr Ala Val Met Asp Cys Phe Cys Glu Pro Thr Trp Gly
140             145                 150 cac act ctg cag tat caa atc gga tac tgc cag cag tgc cct cat aag      713
His Thr Leu Gln Tyr Gln Ile Gly Tyr Cys Gln Gln Cys Pro His Lys
155             160                 165 gtt cag tgg ccc act cac ttt ggg ccc aag cct cct ctc tat ttc aat      761
Val Gln Trp Pro Thr His Phe Gly Pro Lys Pro Pro Leu Tyr Phe Asn
170             175                 180 gct ggc atg ttt gtt tat gag ccc aat ctg gat acc tac cgt gac ctc      809
Ala Gly Met Phe Val Tyr Glu Pro Asn Leu Asp Thr Tyr Arg Asp Leu
185             190                 195 ctt caa act gtc caa gtc act aag ccc act tcc ttt gct gaa cag gat      857
Leu Gln Thr Val Gln Val Thr Lys Pro Thr Ser Phe Ala Glu Gln Asp
200             205                 210                 215 ttt ttg aac atg tac ttc aag gac aaa tat agg cca att cct aat gtc      905
Phe Leu Asn Met Tyr Phe Lys Asp Lys Tyr Arg Pro Ile Pro Asn Val
220             225                 230 tat aat ctt gtg ttg gcc atg ctg tgg cgt cac cct gag aac gtt gag      953
Tyr Asn Leu Val Leu Ala Met Leu Trp Arg His Pro Glu Asn Val Glu
235             240                 245 ctt gaa aaa gtt aaa gtg gtt cac tac tgt gct gct gga tct aag cct     1001
Leu Glu Lys Val Lys Val Val His Tyr Cys Ala Ala Gly Ser Lys Pro
250             255                 260 tgg agg tac aca ggg aag gag gaa aat atg gag aga gaa gat atc aag     1049
Trp Arg Tyr Thr Gly Lys Glu Glu Asn Met Glu Arg Glu Asp Ile Lys
265             270                 275 atg ttg gtg aag aag tgg tgg gat ata tat gag gat gag act ttg gac     1097
Met Leu Val Lys Lys Trp Trp Asp Ile Tyr Glu Asp Glu Thr Leu Asp
280             285                 290                 295 tac aac aat cca ttc aac gtg gat agg ttc act gcg gca ctt ttg gag     1145
Tyr Asn Asn Pro Phe Asn Val Asp Arg Phe Thr Ala Ala Leu Leu Glu
300             305                 310 gtt ggt gaa gtc aag ttc gtc cgt gcc cca tct gct gct tagagtgtct     1194
Val Gly Glu Val Lys Phe Val Arg Ala Pro Ser Ala Ala
315             320 ttggaaatca agtgtgatcc aagtacatag gataagatat acagacccat acatcattaa   1254
gttttatgtg tttttaaagt gtttagagga cctttttatg tgtccctttt ttctttttc    1314 tttttcaatt ctgccattgt aaagcagtga aataccatgt ccttaatttt attattggat   1374
atgaatttta ttttgtacgt tctctaaaaa aaaaaaaaaa aaa                     1417

<210> SEQ ID NO 6
<211> LENGTH: 324
```

<212> TYPE: PRT
<213> ORGANISM: Glycine max

<400> SEQUENCE: 6

Met Ala Pro Asn Ile Thr Thr Val Thr Asp Ala Gln Ala Lys Ala Ala
1               5                   10                  15

Gly Gly Arg Gly Arg Ala Tyr Val Thr Phe Leu Ala Gly Asn Gly Asp
            20                  25                  30

Tyr Val Lys Gly Val Val Gly Leu Ala Lys Gly Leu Arg Lys Val Lys
        35                  40                  45

Ser Met Tyr Pro Leu Val Val Ala Val Leu Pro Asp Val Pro Glu His
    50                  55                  60

His Arg Asn Ile Leu Thr Ser Gln Gly Cys Ile Val Arg Glu Ile Glu
65                  70                  75                  80

Pro Val Tyr Pro Pro Glu Asn Gln Thr Gln Phe Ala Met Ala Tyr Tyr
                85                  90                  95

Val Ile Asn Tyr Ser Lys Leu Arg Ile Trp Glu Phe Val Glu Phe Ser
            100                 105                 110

Lys Met Ile Tyr Leu Asp Gly Asp Ile Gln Val Phe Asp Asn Ile Asp
        115                 120                 125

His Leu Phe Asp Leu Pro Asp Asn Tyr Phe Tyr Ala Val Met Asp Cys
    130                 135                 140

Phe Cys Glu Pro Thr Trp Gly His Thr Leu Gln Tyr Gln Ile Gly Tyr
145                 150                 155                 160

Cys Gln Gln Cys Pro His Lys Val Gln Trp Pro Thr His Phe Gly Pro
                165                 170                 175

Lys Pro Pro Leu Tyr Phe Asn Ala Gly Met Phe Val Tyr Glu Pro Asn
            180                 185                 190

Leu Asp Thr Tyr Arg Asp Leu Leu Gln Thr Val Gln Val Thr Lys Pro
        195                 200                 205

Thr Ser Phe Ala Glu Gln Asp Phe Leu Asn Met Tyr Phe Lys Asp Lys
    210                 215                 220

Tyr Arg Pro Ile Pro Asn Val Tyr Asn Leu Val Leu Ala Met Leu Trp
225                 230                 235                 240

Arg His Pro Glu Asn Val Glu Leu Glu Lys Val Lys Val Val His Tyr
                245                 250                 255

Cys Ala Ala Gly Ser Lys Pro Trp Arg Tyr Thr Gly Lys Glu Glu Asn
            260                 265                 270

Met Glu Arg Glu Asp Ile Lys Met Leu Val Lys Lys Trp Trp Asp Ile
        275                 280                 285

Tyr Glu Asp Glu Thr Leu Asp Tyr Asn Asn Pro Phe Asn Val Asp Arg
    290                 295                 300

Phe Thr Ala Ala Leu Leu Glu Val Gly Glu Val Lys Phe Val Arg Ala
305                 310                 315                 320

Pro Ser Ala Ala

<210> SEQ ID NO 7
<211> LENGTH: 334
<212> TYPE: PRT
<213> ORGANISM: Pisum sativum

<400> SEQUENCE: 7

Met Ala Pro Glu Ile Val Gln Thr Ser Thr Lys Pro Val Thr Gly Phe
1               5                   10                  15

Thr Lys Leu Lys Arg Ala Tyr Val Thr Phe Leu Ala Gly Asn Gly Asp

```
                20                  25                  30

Tyr Val Lys Gly Val Ile Gly Leu Ala Lys Gly Leu Arg Lys Val Lys
 35                  40                  45

Thr Ala Tyr Pro Leu Val Val Ala Val Leu Pro Asp Val Pro Glu Glu
 50                  55                  60

His Arg Glu Met Leu Glu Ser Gln Gly Cys Ile Val Arg Glu Ile Gln
 65                  70                  75                  80

Pro Val Tyr Pro Pro Glu Asn Gln Thr Gln Phe Ala Met Ala Tyr Tyr
             85                  90                  95

Val Ile Asn Tyr Ser Lys Leu Arg Ile Trp Glu Phe Val Glu Tyr Ser
100                 105                 110

Lys Met Ile Tyr Leu Asp Gly Asp Ile Gln Val Tyr Glu Asn Ile Asp
115                 120                 125

His Leu Phe Asp Leu Pro Asp Gly Tyr Phe Tyr Ala Val Met Asp Cys
130                 135                 140

Phe Cys Glu Lys Thr Trp Ser His Thr Pro Gln Tyr Lys Ile Gly Tyr
145                 150                 155                 160

Cys Gln Gln Cys Pro Glu Lys Val Gln Trp Pro Lys Glu Met Gly Glu
            165                 170                 175

Pro Pro Ser Leu Tyr Phe Asn Ala Gly Met Phe Leu Phe Glu Pro Ser
180                 185                 190

Val Glu Thr Tyr Asp Asp Leu Leu Lys Thr Cys Gln Val Thr Ala Pro
195                 200                 205

Thr Pro Phe Ala Asp Gln Asp Phe Leu Asn Met Tyr Phe Lys Asp Ile
210                 215                 220

Tyr Arg Pro Ile Pro Leu Val Tyr Asn Leu Val Leu Ala Met Leu Trp
225                 230                 235                 240

Arg His Pro Glu Asn Val Glu Leu Arg Lys Val Lys Val Val His Tyr
            245                 250                 255

Cys Ala Ala Gly Ser Lys Pro Trp Arg Tyr Thr Gly Lys Glu Glu Asn
260                 265                 270

Met Gln Arg Glu Asp Ile Lys Met Leu Val Gln Lys Trp Leu Asp Ile
275                 280                 285

Tyr Ser Asp Ser Ser Leu Asp Tyr Lys Lys Asn Leu Ser Gly Asn Cys
290                 295                 300

Glu Thr Gln Arg Asn Asp Val Glu Glu Pro Phe Val Gln Ala Leu Ser
305                 310                 315                 320

Glu Val Gly Arg Val Arg Tyr Val Thr Ala Pro Ser Ala Ala
325                 330

<210> SEQ ID NO 8
<211> LENGTH: 335
<212> TYPE: PRT
<213> ORGANISM: Arabidopsis thaliana

<400> SEQUENCE: 8

Met Ala Pro Glu Ile Asn Thr Lys Leu Thr Val Pro Val His Ser Ala
  1               5                  10                  15

Thr Gly Gly Glu Lys Arg Ala Tyr Val Thr Phe Leu Ala Gly Thr Gly
             20                  25                  30

Asp Tyr Val Lys Gly Val Val Gly Leu Ala Lys Gly Leu Arg Lys Ala
 35                  40                  45

Lys Ser Lys Tyr Pro Leu Val Val Ala Val Leu Pro Asp Val Pro Glu
 50                  55                  60
```

```
Asp His Arg Lys Gln Leu Val Asp Gln Gly Cys Val Val Lys Glu Ile
 65                  70                  75                  80

Glu Pro Val Tyr Pro Glu Asn Gln Thr Glu Phe Ala Met Ala Tyr
             85                  90                  95

Tyr Val Ile Asn Tyr Ser Lys Leu Arg Ile Trp Glu Phe Val Glu Tyr
            100                 105                 110

Asn Lys Met Ile Tyr Leu Asp Gly Asp Ile Gln Val Phe Asp Asn Ile
            115                 120                 125

Asp His Leu Phe Asp Leu Pro Asn Gly Gln Phe Tyr Ala Val Met Asp
            130                 135                 140

Cys Phe Cys Glu Lys Thr Trp Ser His Ser Pro Gln Tyr Lys Ile Gly
145                 150                 155                 160

Tyr Cys Gln Gln Cys Pro Asp Lys Val Thr Trp Pro Glu Ala Lys Leu
            165                 170                 175

Gly Pro Lys Pro Pro Leu Tyr Phe Asn Ala Gly Met Phe Val Tyr Glu
            180                 185                 190

Pro Asn Leu Ser Thr Tyr His Asn Leu Leu Glu Thr Val Lys Ile Val
            195                 200                 205

Pro Pro Thr Leu Phe Ala Glu Gln Asp Phe Leu Asn Met Tyr Phe Lys
210                 215                 220

Asp Ile Tyr Lys Pro Ile Pro Pro Val Tyr Asn Leu Val Leu Ala Met
225                 230                 235                 240

Leu Trp Arg His Pro Glu Asn Ile Glu Leu Asp Gln Val Lys Val Val
245                 250                 255

His Tyr Cys Ala Ala Gly Ala Lys Pro Trp Arg Phe Thr Gly Glu Glu
260                 265                 270

Glu Asn Met Asp Arg Glu Asp Ile Lys Met Leu Val Lys Lys Trp Trp
275                 280                 285

Asp Ile Tyr Asn Asp Glu Ser Leu Asp Tyr Lys Asn Val Val Ile Gly
290                 295                 300

Asp Ser His Lys Lys Gln Gln Thr Leu Gln Gln Phe Ile Glu Ala Leu
305                 310                 315                 320

Ser Glu Ala Gly Ala Leu Gln Tyr Val Lys Ala Pro Ser Ala Ala
325                 330                 335

<210> SEQ ID NO 9
<211> LENGTH: 328
<212> TYPE: PRT
<213> ORGANISM: Glycine max

<400> SEQUENCE: 9

Met Ala Pro Asn Ile Thr Thr Val Lys Thr Thr Ile Thr Asp Ala Gln
  1               5                  10                  15

Ala Lys Val Ala Thr Asp His Gly Arg Ala Tyr Val Thr Phe Leu Ala
             20                  25                  30

Gly Asn Gly Asp Tyr Val Lys Gly Val Val Gly Leu Ala Lys Gly Leu
 35                  40                  45

Arg Lys Val Lys Ser Met Tyr Pro Leu Val Val Ala Val Leu Pro Asp
 50                  55                  60

Val Pro Gln Asp His Arg Asn Ile Leu Thr Ser Gln Gly Cys Ile Val
 65                  70                  75                  80

Arg Glu Ile Glu Pro Val Tyr Pro Pro Glu Asn Gln Thr Gln Phe Ala
             85                  90                  95

Met Ala Tyr Tyr Val Ile Asn Tyr Ser Lys Leu Arg Ile Trp Glu Phe
            100                 105                 110
```

```
Val Glu Tyr Ser Lys Met Ile Tyr Leu Asp Gly Asp Ile Gln Val Phe
115                 120                 125

Asp Asn Ile Asp His Leu Phe Asp Leu Pro Asp Asn Tyr Phe Tyr Ala
130                 135                 140

Val Met Asp Cys Phe Cys Glu Pro Thr Trp Gly His Thr Lys Gln Tyr
145                 150                 155                 160

Gln Ile Gly Tyr Cys Gln Gln Cys Pro His Lys Val Gln Trp Pro Thr
    165                 170                 175

His Phe Gly Pro Lys Pro Pro Leu Tyr Phe Asn Ala Gly Met Phe Val
    180                 185                 190

Tyr Glu Pro Asn Leu Ala Thr Tyr Arg Asp Leu Leu Gln Thr Val Gln
    195                 200                 205

Val Thr Gln Pro Thr Ser Phe Ala Glu Gln Asp Phe Leu Asn Ile Tyr
210                 215                 220

Phe Lys Asp Lys Tyr Arg Pro Ile Pro Asn Val Tyr Asn Leu Val Leu
225                 230                 235                 240

Ala Met Leu Trp Arg His Pro Glu Asn Val Glu Leu Asp Lys Val Lys
245                 250                 255

Val Val His Tyr Cys Ala Ala Gly Ser Lys Pro Trp Arg Tyr Thr Gly
260                 265                 270

Lys Glu Glu Asn Met Glu Arg Glu Asp Ile Lys Met Leu Val Lys Lys
275                 280                 285

Trp Trp Asp Ile Tyr Glu Asp Glu Thr Leu Asp Tyr Asn Asn Pro Leu
290                 295                 300

Asn Val Asp Lys Phe Thr Ala Ala Leu Met Glu Val Gly Glu Val Lys
305                 310                 315                 320

Phe Val Arg Ala Pro Ser Ala Ala
325

<210> SEQ ID NO 10
<211> LENGTH: 1406
<212> TYPE: DNA
<213> ORGANISM: Glycine max

<400> SEQUENCE: 10
gtttgttttc aaagtgtgtt ttgtttccca atcctactc ttgtgaccac aaccctttcct    60 cctctttctt ttgaaacctc ttttttttcta ttccccaacc aaacaagcaa acgctactca   120
ctcatcatca ctgagatcat ggctcctaat atcaccactg tcaaaaccac catcaccgac   180
gctcaagcca aggtcgccac cgatcatggt cgtgcctacg tcaccttcct cgccggaaac   240
ggtgactatg tgaaaggtgt cgttggcttg gcaaaaggtc tgagaaaagt gaagagcatg   300
taccctctgg tggttgcagt gctacccgat gttccccaag atcaccgcaa cattctcacc   360
tcccaaggtt gcattgttag agagattgag cccgtgtacc ccccagagaa tcaaacccag   420
tttgccatgg catattacgt catcaactat tccaagctac gtatttggga gtttgtggag   480
tacagcaaga tgatataacct agacggtgat atccaagttt ttgacaacat tgaccacttg   540
tttgacttgc ctgataacta cttctatgcg gtgatggact gtttctgtga gccaacttgg   600
ggccacacta acaatatca gatcggttac tgccagcagt gccccataa ggttcagtgg   660 cccactcact tgggcccaa acctcctctc tatttcaatg ctggcatgtt tgtgtatgag   720
cccaatttgg ctacttaccg tgacctcctt caaacagtcc aagtcaccca gcccacttcc   780
tttgctgaac aggattttt gaacatgtac ttcaaggaca aatataggcc aattcctaat   840
```

-continued

| | |
|---|---|
| gtctacaatc ttgtgctggc catgctgtgg cgtcaccctg agaacgttga gcttgacaaa | 900 |
| gttaaagtgg ttcactactg tgctgctggg tctaagcctt ggaggtacac tgggaaggag | 960 |
| gagaatatgg agagagaaga tatcaagatg ttagtgaaaa agtggtggga tatatatgag | 1020 |
| gatgagactt tggactacaa caatccactc aatgtggata agttcactgc ggcacttatg | 1080 |
| gaggttggtg aagtcaagtt cgtccgtgcc ccatctgctg cttaagagtg tctttggaaa | 1140 |
| tcaagtgtga tccaagtaca tgtacaaagt catacatcat tacattaact tttatgtatt | 1200 |
| tctaaaagtc atacatcatt acattaagtt ttatgtattt ctaaagtctt aagacttaag | 1260 |
| aggaccttt ttatkkkkcc cgcttttctt ttttctttt tccaattctg tcattgtaaa | 1320 |
| gsrgagaata ccgtatcctt aattttataa atggatatga attttatttg tactaaaggg | 1380 |
| ggggccggta ccaattcgcc tatagt | 1406 |

<210> SEQ ID NO 11
<211> LENGTH: 1350
<212> TYPE: DNA
<213> ORGANISM: Glycine max

<400> SEQUENCE: 11

| | |
|---|---|
| gcacgagaaa caaccaacct cttcagtgat ctttgattag tactaagcta aaccatttct | 60 |
| tattccctca aaatcaaaac cttttttcttt ctagctattt cccttttcaa atcatgccac | 120 |
| ctaacatcac caccgttgtt gccaatgtca ccaccgagca attacccaag gctcgtggag | 180 |
| gaagtgggcg tgccttcgtg acctttcttg ctgggaacgg tgattacgta aagggtgtcg | 240 |
| tgggtttggc caaaggactg agaaaggcca aagcatgta ccctttggtg gttgctgtgt | 300 |
| taccagatgt tcctgaagaa catcgtgaga ttctcaaatc ccaaggttgc attgtcaggg | 360 |
| agattgaacc tgtgtaccct cctgagaacc agacccagtt cgccatggcc tattatgtca | 420 |
| tcaattactc caagctacgt atttgggagt tcgtggagta caagaagacg atataccatg | 480 |
| acggtgacat ccaagtattt ggaaacatag accacttgtt tgatctgcct gataattatt | 540 |
| tctatgcggt gatggattgt ttctgcgaga agacttggag ccacacccct cagttccaga | 600 |
| ttgggtactg ccaacagtgc cctgataagg ttcaatggcc tctctacttt ggttccaaac | 660 |
| ctcctctata tttcaatgct ggcatgtttg tttatgagcc taatctcgac acctaccgtg | 720 |
| atcttctcca aactgtccaa ctcaccaagc ccacttcttt tgctgagcag gactttctca | 780 |
| acatgtactt caaggacaag tacaagccaa taccgaacat gtacaacctt gtgctggcca | 840 |
| tgttgtggcg tcaccctgaa aatgttgaac ttgataaagt tcaagtggtt cattactgtg | 900 |
| ctgctgggtc taagccttgg aggttcactg ggaaggaaga gaacatggat agggaagata | 960 |
| tcaagatgct tgtgaagaag tggtgggaca tatatgaaga tgagacactg gactacaata | 1020 |
| acaactctgt caacgtggaa cgtttcacat cggcactatt ggatgctggg ggctttcagt | 1080 |
| ttgtgccagc accttctgct gcctaatatg cttattattt acagctacaa attaatgtta | 1140 |
| attaacgaca agtatatgt attgttattt gctttttttc gttttttgggt cttatatatg | 1200 |
| aaggaacaac gtctatggtt ttaatttgga tgaccttctt gtatacaaag ccacatgtga | 1260 |
| tctcatacag cttttgatta ttattaagaa attagaggac cttttattat gagtcccttta | 1320 |
| cttaaaaaaa aaaaaaaaa aaaaaaaaaa | 1350 |

<210> SEQ ID NO 12
<211> LENGTH: 36
<212> TYPE: DNA
<213> ORGANISM: Artificial

```
<220> FEATURE:
<223> OTHER INFORMATION: Primer

<400> SEQUENCE: 12
aagcttgcgg ccgcgtcatc aactattcca agctac                                36

<210> SEQ ID NO 13
<211> LENGTH: 36
<212> TYPE: DNA
<213> ORGANISM: Artificial
<220> FEATURE:
<223> OTHER INFORMATION: Primer

<400> SEQUENCE: 13
aagcttctcg agtcacttcc cagtgtacct ccaagg                                36

<210> SEQ ID NO 14
<211> LENGTH: 519
<212> TYPE: DNA
<213> ORGANISM: Glycine Max

<400> SEQUENCE: 14
gtcatcaact attccaagct acgtatttgg gagtttgtgg agtacagcaa gatgatatac       60
ctagacggtg atatccaagt ttttgacaac attgaccact tgtttgactt gcctgataac      120
tacttctatg cggtgatgga ctgtttctgt gagccaactt ggggccacac taaacaatat      180
cagatcggtt actgccagca gtgcccccat aaggttcagt ggcccactca ctttgggccc      240
aaacctcctc tctatttcaa tgctggcatg tttgtgtatg agcccaattt ggctacttac      300
cgtgacctcc ttcaaacagt ccaagtcacc cagcccactt cctttgctga acaggatttt      360
ttgaacatgt acttcaagga caaatatagg ccaattccta atgtctacaa tcttgtgctg      420
gccatgctgt ggcgtcaccc tgagaacgtt gagcttgaca agttaaagt ggttcactac       480 tgtgctgctg ggtctaagcc ttggaggtac actgggaag                             519

<210> SEQ ID NO 15
<211> LENGTH: 34
<212> TYPE: DNA
<213> ORGANISM: Artificial
<220> FEATURE:
<223> OTHER INFORMATION: Primer

<400> SEQUENCE: 15
aagcttctcg aggtcatcaa ttactccaag ctac                                  34

<210> SEQ ID NO 16
<211> LENGTH: 43
<212> TYPE: DNA
<213> ORGANISM: Artificial
<220> FEATURE:
<223> OTHER INFORMATION: Primer

<400> SEQUENCE: 16
agcttgcggc cgcctgcagt tacttcccag tgaacctcca agg                        43

<210> SEQ ID NO 17
<211> LENGTH: 519
<212> TYPE: DNA
<213> ORGANISM: Glycine max

<400> SEQUENCE: 17
gtcatcaatt actccaagct acgtatttgg gagttcgtgg agtacaagaa gacgatatac       60
```

```
ctagacggtg acatccaagt atttggaaac atagaccact tgtttgatct gcctgataat    120
tatttctatg cggtgatgga ttgtttctgc gagaagactt ggagccacac ccctcagttc    180
cagattgggt actgccaaca gtgccctgat aaggttcaat ggccctctca ctttggttcc    240
aaacctcctc tatatttcaa tgctggcatg tttgtttatg agcctaatct cgacacctac    300
cgtgatcttc tccaaactgt ccaactcacc aagcccactt cttttgctga gcaggacttt    360
ctcaacatgt acttcaagga caagtacaag ccaataccga acatgtacaa ccttgtgctg    420
gccatgttgt ggcgtcaccc tgaaaatgtt gaacttgata aagttcaagt ggttcattac    480
tgtgctgctg ggtctaagcc ttggaggttc actgggaag                          519
```

<210> SEQ ID NO 18
<211> LENGTH: 42
<212> TYPE: DNA
<213> ORGANISM: Artificial
<220> FEATURE:
<223> OTHER INFORMATION: Primer

<400> SEQUENCE: 18

```
aagcttgcgg ccgcctgcag gtcatcaact actccaagct cc                       42
```

<210> SEQ ID NO 19
<211> LENGTH: 37
<212> TYPE: DNA
<213> ORGANISM: Artificial
<220> FEATURE:
<223> OTHER INFORMATION: Primer

<400> SEQUENCE: 19

```
aagcttgcgg ccgctacttc cccgtatatc tccatgg                             37
```

<210> SEQ ID NO 20
<211> LENGTH: 519
<212> TYPE: DNA
<213> ORGANISM: Glycine max

<400> SEQUENCE: 20

```
gtcatcaact actccaagct ccgtatatgg gagtttgtgg agtacagcaa gatgatatac    60
ttggacggag acattgaggt atatgagaac atagaccacc tatttgacct acctgatggt    120
aacttttacg ctgtgatgga ttgtttctgc gagaagacat ggagtcacac ccctcagtac    180
aaggtgggtt actgccagca atgcccggag aaggtgcggt ggccaccgaa attgggtcag    240
cccccttctc tttacttcaa cgctggcatg ttcgtgttcg aacccaacat cgccacctat    300
catgacctat tgaaaacggt gcaagtcacc actcccacct cgttcgctga caagatttc    360 ttgaacatgt acttcaagga catttacaag ccaatccctt taaattacaa tcttgtcctc    420
gccatgctgt ggcgccaccc ggaaaacgtt aaattagacc aagtcaaggt tgttcactat    480
tgcgcagcgg ggtccaagcc atggagatat acggggaag                          519
```

<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21

```
tcttctgttc ttgccgttgc tttctc                                         26
```

```
<210> SEQ ID NO 22
<211> LENGTH: 33
<212> TYPE: DNA
<213> ORGANISM: Artificial
<220> FEATURE:
<223> OTHER INFORMATION: Primer

<400> SEQUENCE: 22
cgcggatccg acttgctcct tggcagcact ggt                               33

<210> SEQ ID NO 23
<211> LENGTH: 597
<212> TYPE: DNA
<213> ORGANISM: Glycine max

<400> SEQUENCE: 23
agagttttta taagttattt tatacatgaa ttaattttaa cttgtgaaaa aaattatttt     60
cttcttataa gtatttatga caaagcttat ataaacatag tcttaatttc actcagaaaa   120
acagaggagg aaaacttgtt gtatgaagcc cggctatttc atccattatc catatttgga   180
tcgaaaagag aaggaaagtg tcattttata tgtgtataaa aagtatttca tccataagta   240
atgataagat aattgtgtat gtaacattat taatgtattt aaattaaaat cataaattat   300
tttaaacaat tcttattcgt tagtgacacg ataacggata agctaataat atatctatgg   360
ttttctgtga acgtggcagc atattgatgg gaatagctct gcatgttgaa caagtggcac   420
ggtacctagc gtgccttgct cttcttttgt ctaggcttgg tttggttcgc atcttccttc   480
tcatataaat cctccaccac gtcgagtttt ctgttcaaat taaatcgttc aacactggaa   540
ctctttgata taatatagaa agagacagag agagagagac agacaagaag aacaagg      597

<210> SEQ ID NO 24
<211> LENGTH: 42
<212> TYPE: DNA
<213> ORGANISM: Artificial
<220> FEATURE:
<223> OTHER INFORMATION: Primer

<400> SEQUENCE: 24
cgcggatcca gagttttat aagttatttt atacatgaat ta                       42

<210> SEQ ID NO 25
<211> LENGTH: 39
<212> TYPE: DNA
<213> ORGANISM: Artificial
<220> FEATURE:
<223> OTHER INFORMATION: Primer

<400> SEQUENCE: 25
ccttgaccat ggttgttctt cttgtctgtc tctctctct                          39

<210> SEQ ID NO 26
<211> LENGTH: 81
<212> TYPE: DNA
<213> ORGANISM: Artificial
<220> FEATURE:
<223> OTHER INFORMATION: two copies of Eag1-ELVISLIVES

<400> SEQUENCE: 26
cggccggagc tggtcatctc gctcatcgtc gagtcggcgg ccggagctgg tcatctcgct    60
catcgtcgag tcggcggccg c                                             81

<210> SEQ ID NO 27
```

```
<211> LENGTH: 81
<212> TYPE: DNA
<213> ORGANISM: Artificial
<220> FEATURE:
<223> OTHER INFORMATION: Complementary strand of two copies of
      Eag1-ELVISLIVES

<400> SEQUENCE: 27
gcggccgccg actcgacgat gagcgagatg accagctccg ccgccgact cgacgatgag    60 cgagatgacc agctccggcc g                                             81

<210> SEQ ID NO 28
<211> LENGTH: 69
<212> TYPE: DNA
<213> ORGANISM: Artificial
<220> FEATURE:
<223> OTHER INFORMATION: truncated version of the two copies of
      ELVISLIVES linker

<400> SEQUENCE: 28
gcggccgccg actcgacgat gagcgagatg accagctccg ccgccgact cgacgatgag    60 cgagagctc                                                           69

<210> SEQ ID NO 29
<211> LENGTH: 8810
<212> TYPE: DNA
<213> ORGANISM: Artificial
<220> FEATURE:
<223> OTHER INFORMATION: Plasmid SH50

<400> SEQUENCE: 29
ggccgccgac tcgacgatga gcgagatgac cagctccggc cgccgactcg acgatgagcg     60
agagctccgg ccgcaagtat gaactaaaat gcacgtaggt gtaagagctc atggagagca   120
tggaatattg tatccgacca tgtaacagta taataactga gctccatctc acttcttcta   180
tgaataaaca aaggatgtta tgatatatta acactctatc tatgcacctt attgttctat   240
gataaatttc ctcttattat tataaatcat ctgaatcgtg acggcttatg gaatgcttca   300
aatagtacaa aaacaaatgt gtactataag actttctaaa caattctaac tttagcattg   360
tgaacgagac ataagtgtta agaagacata acaattataa tggaagaagt ttgtctccat   420
ttatatatta tatattaccc acttatgtat tatattagga tgttaaggag acataacaat   480
tataaagaga gaagtttgta tccatttata tattatatac tacccattta tatattatac   540
ttatccactt atttaatgtc tttataaggt ttgatccatg atatttctaa tattttagtt   600
gatatgtata tgaaagggta ctatttgaac tctcttactc tgtataaagg ttggatcatc   660
cttaaagtgg gtctatttaa ttttattgct tcttacagat aaaaaaaaaa ttatgagttg   720
gtttgataaa atattgaagg atttaaaata ataataaata acatataata tatgtatata   780
aatttattat aatataacat ttatctataa aaaagtaaat attgtcataa atctatacaa   840
tcgtttagcc ttgctggacg aatctcaatt atttaaacga gagtaaacat atttgacttt   900
ttggttattt aacaaattat tatttaacac tatatgaaat ttttttttttt atcagcaaag   960 aataaaatta aattaaggag acaatggtg tcccaatcct tatacaacca acttccacaa   1020
gaaagtcaag tcagagacaa caaaaaaaca agcaaaggaa attttttaat ttgagttgtc  1080
ttgtttgctg cataaattat gcagtaaaac actacacata acccttttag cagtaaagca  1140
atggttgacc gtgtgcttag cttctttat tttatttttt tatcagcaaa gaataaataa   1200
aataaaatga gacacttcag ggatgtttca acggatccaa gcttggcgcg ccgttctata  1260
```

```
gtgtcaccta aatcgtatgt gtatgataca taaggttatg tattaattgt agccgcgttc   1320
taacgacaat atgtccatat ggtgcactct cagtacaatc tgctctgatg ccgcatagtt   1380
aagccagccc cgacacccgc caacacccgc tgacgcgccc tgacgggctt gtctgctccc   1440
ggcatccgct tacagacaag ctgtgaccgt ctccgggagc tgcatgtgtc agaggttttc   1500
accgtcatca ccgaaacgcg cgagacgaaa gggcctcgtg atacgcctat ttttataggt   1560
taatgtcatg accaaaatcc cttaacgtga gttttcgttc cactgagcgt cagacccgt    1620 agaaaagatc aaaggatctt cttgagatcc ttttttttctg cgcgtaatct gctgcttgca  1680
aacaaaaaaa ccaccgctac cagcggtggt ttgtttgccg gatcaagagc taccaactct   1740
ttttccgaag gtaactggct tcagcagagc gcagatacca atactgtcc ttctagtgta    1800 gccgtagtta ggccaccact tcaagaactc tgtagcaccg cctacatacc tcgctctgct   1860
aatcctgtta ccagtggctg ctgccagtgg cgataagtcg tgtcttaccg ggttggactc   1920
aagacgatag ttaccggata aggcgcagcg gtcgggctga acggggggtt cgtgcacaca   1980
gcccagcttg gagcgaacga cctacaccga actgagatac ctacagcgtg agcattgaga   2040
aagcgccacg cttcccgaag ggagaaaggc ggacaggtat ccggtaagcg gcagggtcgg   2100
aacaggagag cgcacgaggg agcttccagg gggaaacgcc tggtatcttt atagtcctgt   2160
cgggtttcgc cacctctgac ttgagcgtcg atttttgtga tgctcgtcag ggggcggag    2220 cctatgaaa aacgccagca acgcggcctt tttacggttc ctggccttt gctggccttt     2280 tgctcacatg ttctttcctg cgttatcccc tgattctgtg ataaccgta ttaccgcctt    2340 tgagtgagct gataccgctc gccgcagccg aacgaccgag cgcagcgagt cagtgagcga   2400
ggaagcggaa gagcgcccaa tacgcaaacc gcctctcccc gcgcgttggc cgattcatta   2460
atgcaggttg atcagattcg acatcgatct agtaacatag atgacaccgc gcgcgataat   2520
ttatcctagt ttgcgcgcta tattttgttt tctatcgcgt attaaatgta taattgcggg   2580
actctaatca taaaaaccca tctcataaat aacgtcatgc attacatgtt aattattaca   2640
tgcttaacgt aattcaacag aaattatatg ataatcatcg caagaccggc aacaggattc   2700
aatcttaaga aactttattg ccaaatgttt gaacgatctg cttcgacgca ctccttcttt   2760
aggtacctca ctattccttt gccctcggac gagtgctggg gcgtcggttt ccactatcgg   2820
cgagtacttc tacacagcca tcggtccaga cggccgcgct tctgcgggcg atttgtgtac   2880
gcccgacagt cccggctccg gatcggacga ttgcgtcgca tcgaccctgc gcccaagctg   2940
catcatcgaa attgccgtca accaagctct gatagagttg gtcaagacca atgcggagca   3000
tatacgcccg gagccgcggc gatcctgcaa gctccggatg cctccgctcg aagtagcgcg   3060
tctgctgctc catacaagcc aaccacggcc tccagaagaa gatgttggcg acctcgtatt   3120
gggaatcccc gaacatcgcc tcgctccagt caatgaccgc tgttatgcgg ccattgtccg   3180
tcaggacatt gttggagccg aaatccgcgt gcacgaggtg ccggacttcg ggcagtcct    3240 cggcccaaag catcagctca tcgagagcct gcgcgacgga cgcactgacg gtgtcgtcca   3300
tcacagtttg ccagtgatac acatggggat cagcaatcgc gcatatgaaa tcacgccatg   3360
tagtgtattg accgattcct tgcggtccga atgggccgaa cccgctcgtc tggctaagat   3420
cggccgcagc gatcgcatcc atggcctccg cgaccggctg cagaacagcg gcagttcgg    3480 tttcaggcag gtcttgcaac gtgacaccct gtgcacggcg ggagatgcaa taggtcaggc   3540
tctcgctgaa ttccccaatg tcaagcactt ccggaatcgg gagcgcggcc gatgcaaagt   3600
```

-continued

```
gccgataaac ataacgatct ttgtagaaac catcggcgca gctatttacc cgcaggacat      3660
atccacgccc tcctacatcg aagctgaaag cacgagattc ttcgccctcc gagagctgca      3720
tcaggtcgga gacgctgtcg aacttttcga tcagaaactt ctcgacagac gtcgcggtga      3780
gttcaggctt tttcatggtt taataagaag agaaaagagt tcttttgtta tggctgaagt      3840
aatagagaaa tgagctcgag cgtgtcctct ccaaatgaaa tgaacttcct tatatagagg      3900
aagggtcttg cgaaggatag tgggattgtg cgtcatccct tacgtcagtg gagatgtcac      3960
atcaatccac ttgctttgaa gacgtggttg gaacgtcttc tttttccacg atgctcctcg      4020
tgggtggggg tccatctttg ggaccactgt cggcagaggc atcttgaatg atagcctttc      4080
ctttatcgca atgatggcat ttgtaggagc caccttcctt ttctactgtc ctttcgatga      4140
agtgacagat agctgggcaa tggaatccga ggaggtttcc cgaaattatc ctttgttgaa      4200
aagtctcaat agcccttttgg tcttctgaga ctgtatcttt gacattttg gagtagacca      4260 gagtgtcgtg ctccaccatg ttgacgaaga ttttcttctt gtcattgagt cgtaaaagac      4320
tctgtatgaa ctgttcgcca gtcttcacgg cgagttctgt tagatcctcg atttgaatct      4380
tagactccat gcatggcctt agattcagta ggaactacct ttttagagac tccaatctct      4440
attacttgcc ttggtttatg aagcaagcct tgaatcgtcc atactggaat agtacttctg      4500
atcttgagaa atatgtcttt ctctgtgttc ttgatgcaat tagtcctgaa tcttttgact      4560
gcatctttaa ccttcttggg aaggtatttg atctcctgga gattgttact cgggtagatc      4620
gtcttgatga gacctgctgc gtaggcctct ctaaccatct gtgggtcagc attctttctg      4680
aaattgaaga ggctaacctt ctcattatca gtggtgaaca tagtgtcgtc accttcacct      4740
tcgaacttcc ttcctagatc gtaaagatag aggaaatcgt ccattgtaat ctccggggca      4800
aaggagatct cttttggggc tggatcactg ctgggccttt tggttcctag cgtgagccag      4860
tgggcttttt gctttggtgg gcttgttagg gccttagcaa agctcttggg cttgagttga      4920
gcttctcctt tggggatgaa gttcaacctg tctgtttgct gacttgttgt gtacgcgtca      4980
gctgctgctc ttgcctctgt aatagtggca aatttcttgt gtgcaactcc gggaacgccg      5040
tttgttgccg cctttgtaca accccagtca tcgtatatac cggcatgtgg accgttatac      5100
acaacgtagt agttgatatg agggtgttga atacccgatt ctgctctgag aggagcaact      5160
gtgctgttaa gctcagattt ttgtgggatt ggaattggat cgatctcgat cccgcgaaat      5220
taatacgact cactataggg agaccacaac ggtttccctc tagaaataat tttgtttaac      5280
tttaagaagg agatataccc atggaaaagc ctgaactcac cgcgacgtct gtcgagaagt      5340
ttctgatcga aaagttcgac agcgtctccg acctgatgca gctctcggag ggcgaagaat      5400
ctcgtgcttt cagcttcgat gtaggagggc gtggatatgt cctgcgggta aatagctgcg      5460
ccgatggttt ctacaaagat cgttatgttt atcggcactt tgcatcggcc gcgctcccga      5520
ttccggaagt gcttgacatt ggggaattca gcgagagcct gacctattgc atctcccgcc      5580
gtgcacaggg tgtcacgttg caagacctgc ctgaaaccga actgcccgct gttctgcagc      5640
cggtcgcgga ggctatggat gcgatcgctg cggccgatct tagccagacg agcgggttcg      5700
gcccattcgg accgcaagga atcggtcaat acactacatg gcgtgatttc atatgcgcga      5760
ttgctgatcc ccatgtgtat cactggcaaa ctgtgatgga cgacaccgtc agtgcgtccg      5820
tcgcgcaggc tctcgatgag ctgatgcttt gggccgagga ctgccccgaa gtccggcacc      5880
tcgtgcacgc ggatttcggc tccaacaatg tcctgacgga caatggccgc ataacagcgg      5940
tcattgactg gagcgaggcg atgttcgggg attcccaata cgaggtcgcc aacatcttct      6000
```

```
tctggaggcc gtggttggct tgtatggagc agcagacgcg ctacttcgag cggaggcatc    6060
cggagcttgc aggatcgccg cggctccggg cgtatatgct ccgcattggt cttgaccaac    6120
tctatcagag cttggttgac ggcaatttcg atgatgcagc ttgggcgcag ggtcgatgcg    6180
acgcaatcgt ccgatccgga gccgggactg tcgggcgtac acaaatcgcc cgcagaagcg    6240
cggccgtctg gaccgatggc tgtgtagaag tactcgccga tagtggaaac cgacgcccca    6300
gcactcgtcc gagggcaaag gaatagtgag gtacagcttg gatcgatccg gctgctaaca    6360
aagcccgaaa ggaagctgag ttggctgctg ccaccgctga gcaataacta gcataacccc    6420
ttggggcctc taaacgggtc ttgaggggtt ttttgctgaa aggaggaact atatccggat    6480
gatcgggcgc gccgtcgacg gtatcgataa gcttgatatc gaattcctgc agcccggggg    6540
atccagagtt tttataagtt attttataca tgaattaatt ttaacttgtg aaaaaaatta    6600
ttttcttctt ataagtattt atgacaaagc ttatataaac atagtcttaa tttcactcag    6660
aaaaacagag gaggaaaact tgttgtatga agcccggcta tttcatccat tatccatatt    6720
tggatcgaaa agagaaggaa agtgtcattt tatatgtgta taaaaagtat ttcatccata    6780
agtaatgata agataattgt gtatgtaaca ttattaatgt atttaaatta aaatcataaa    6840
ttattttaaa caattcttat tcgttagtga cacgataacg gataagctaa taatatatct    6900
atggttttct gtgaacgtgg cagcatattg atgggaatag ctctgcatgt tgaacaagtg    6960
gcacggtacc tagcgtgcct tgctcttctt ttgtctaggc ttggtttggt tcgcatcttc    7020
cttctcatat aaatcctcca ccacgtcgag ttttctgttc aaattaaatc gttcaacact    7080
ggaactcttt gatataatat agaaagagac agagagagag agacagacaa gaagaacaac    7140
catgctagag cggccggagc tggtcatctc gctcatcgtc gagtcggcgg ccggagctgg    7200
tcatctcgct catcgtcgag tcggcggccg cgtcatcaac tattccaagc tacgtatttg    7260
ggagtttgtg gagtacagca agatgatata cctagacggt gatatccaag tttttgacaa    7320
cattgaccac ttgtttgact tgcctgataa ctacttctat gcggtgatgg actgtttctg    7380
tgagccaact tggggccaca ctaaacaata tcagatcggt tactgccagc agtgccccca    7440
taaggttcag tggcccactc actttgggcc caaacctcct ctctatttca atgctggcat    7500
gtttgtgtat gagcccaatt tggctactta ccgtgacctc cttcaaacag tccaagtcac    7560
ccagcccact tcctttgctg aacaggattt tttgaacatg tacttcaagg acaaatatag    7620
gccaattcct aatgtctaca atcttgtgct ggccatgctg tggcgtcacc ctgagaacgt    7680
tgagcttgac aaagttaaag tggttcacta ctgtgctgct gggtctaagc cttggaggta    7740
cactgggaag tgactcgagg tcatcaatta ctccaagcta cgtatttggg agttcgtgga    7800
gtacaagaag acgatatacc tagacggtga catccaagta tttggaaaca tagaccactt    7860
gtttgatctg cctgataatt atttctatgc ggtgatggat tgtttctgcg agaagacttg    7920
gagccacacc cctcagttcc agattgggta ctgccaacag tgccctgata aggttcaatg    7980
gccctctcac tttggttcca aacctcctct atatttcaat gctggcatgt ttgtttatga    8040
gcctaatctc gacacctacc gtgatcttct ccaaactgtc caactcacca gcccacttc    8100
ttttgctgag caggactttc tcaacatgta cttcaaggac aagtacaagc caataccgaa    8160
catgtacaac cttgtgctgg ccatgttgtg gcgtcaccct gaaaatgttg aacttgataa    8220
agttcaagtg gttcattact gtgctgctgg gtctaagcct tggaggttca ctgggaagta    8280
actgcaggtc atcaactact ccaagctccg tatatgggag tttgtggagt acagcaagat    8340
```

| | |
|---|---:|
| gatatacttg gacggagaca ttgaggtata tgagaacata gaccacctat ttgacctacc | 8400 |
| tgatggtaac ttttacgctg tgatggattg tttctgcgag aagacatgga gtcacacccc | 8460 |
| tcagtacaag gtgggttact gccagcaatg cccggagaag gtgcggtggc ccaccgaatt | 8520 |
| gggtcagccc ccttctcttt acttcaacgc tggcatgttc gtgttcgaac ccaacatcgc | 8580 |
| cacctatcat gacctattga aaacggtgca agtcaccact cccacctcgt tcgctgaaca | 8640 |
| agatttcttg aacatgtact tcaaggacat ttacaagcca atccctttaa attacaatct | 8700 |
| tgtcctcgcc atgctgtggc gccacccgga aaacgttaaa ttagaccaag tcaaggttgt | 8760 |
| tcactattgc gcagcggggt ccaagccatg gagatatacg gggaagtagc | 8810 |

<210> SEQ ID NO 30
<211> LENGTH: 4479
<212> TYPE: DNA
<213> ORGANISM: Artificial
<220> FEATURE:
<223> OTHER INFORMATION: Plasmid pKR57

<400> SEQUENCE: 30

| | |
|---|---:|
| ctagagtcga cctgcaggca tgcaagcttg gcgtaatcat ggtcatagct gtttcctgtg | 60 |
| tgaaattgtt atccgctcac aattccacac aacatacgag ccggaagcat aaagtgtaaa | 120 |
| gcctggggtg cctaatgagt gagctaactc acattaattg cgttgcgctc actgcccgct | 180 |
| ttccagtcgg gaaacctgtc gtgccagctg cattaatgaa tcggccaacg cgcggggaga | 240 |
| ggcggtttgc gtattgggcg ctcttccgct tcctcgctca ctgactcgct gcgctcggtc | 300 |
| gttcggctgc ggcgagcggt atcagctcac tcaaaggcgg taatacggtt atccacagaa | 360 |
| tcaggggata acgcaggaaa gaacatgtga gcaaaaggcc agcaaaaggc caggaaccgt | 420 |
| aaaaaggccg cgttgctggc gtttttccat aggctccgcc cccctgacga gcatcacaaa | 480 |
| aatcgacgct caagtcagag gtggcgaaac ccgacaggac tataaagata ccaggcgttt | 540 |
| cccccctggaa gctccctcgt gcgctctcct gttccgaccc tgccgcttac cggatacctg | 600 |
| tccgcctttc tcccttcggg aagcgtggcg ctttctcata gctcacgctg taggtatctc | 660 |
| agttcggtgt aggtcgttcg ctccaagctg ggctgtgtgc acgaaccccc cgttcagccc | 720 |
| gaccgctgcg ccttatccgg taactatcgt cttgagtcca acccggtaag acacgactta | 780 |
| tcgccactgg cagcagccac tggtaacagg attagcagag cgaggtatgt aggcggtgct | 840 |
| acagagttct tgaagtggtg gcctaactac ggctacacta aaggacagt atttggtatc | 900 |
| tgcgctctgc tgaagccagt taccttcgga aaaagagttg gtagctcttg atccggcaaa | 960 |
| caaaccaccg ctggtagcgg tggttttttt gtttgcaagc agcagattac gcgcagaaaa | 1020 |
| aaaggatctc aagaagatcc tttgatcttt tctacgggt ctgacgctca gtggaacgaa | 1080 |
| aactcacgtt aagggatttt ggtcatgaga ttatcaaaaa ggatcttcac ctagatcctt | 1140 |
| ttaaattaaa aatgaagttt taaatcaatc taaagtatat atgagtaaac ttggtctgac | 1200 |
| agttaccaat gcttaatcag tgaggcacct atctcagcga tctgtctatt tcgttcatcc | 1260 |
| atagttgcct gactccccgt cgtgtagata actacgatac gggagggctt accatctggc | 1320 |
| cccagtgctg caatgatacc gcgagaccca cgctcaccgg ctccagattt atcagcaata | 1380 |
| aaccagccag ccggaagggc cgagcgcaga agtggtcctg caactttatc cgcctccatc | 1440 |
| cagtctatta attgttgccg ggaagctaga gtaagtagtt cgccagttaa tagtttgcgc | 1500 |
| aacgttgttg ccattgctac aggcatcgtg gtgtcacgct cgtcgtttgg tatggcttca | 1560 |
| ttcagctccg gttcccaacg atcaaggcga gttacatgat cccccatgtt gtgcaaaaaa | 1620 |

```
gcggttagct ccttcggtcc tccgatcgtt gtcagaagta agttggccgc agtgttatca    1680
ctcatggtta tggcagcact gcataattct cttactgtca tgccatccgt aagatgcttt    1740
tctgtgactg gtgagtactc aaccaagtca ttctgagaat agtgtatgcg gcgaccgagt    1800
tgctcttgcc cggcgtcaat acgggataat accgcgccac atagcagaac tttaaaagtg    1860
ctcatcattg gaaaacgttc ttcggggcga aaactctcaa ggatcttacc gctgttgaga    1920
tccagttcga tgtaacccac tcgtgcaccc aactgatctt cagcatcttt tactttcacc    1980
agcgtttctg ggtgagcaaa aacaggaagg caaaatgccg caaaaaaggg aataagggcg    2040
acacggaaat gttgaatact catactcttc cttttcaat attattgaag catttatcag     2100
ggttattgtc tcatgagcgg atacatattt gaatgtattt agaaaaataa acaaataggg    2160
gttccgcgca catttccccg aaaagtgcca cctgacgtct aagaaaccat tattatcatg    2220
acattaacct ataaaaatag gcgtatcacg aggccctttc gtctcgcgcg tttcggtgat    2280
gacggtgaaa acctctgaca catgcagctc ccggagacgg tcacagcttg tctgtaagcg    2340
gatgccggga gcagacaagc ccgtcagggc gcgtcagcgg gtgttggcgg gtgtcggggc    2400
tggcttaact atgcggcatc agagcagatt gtactgagag tgcaccatat gcggtgtgaa    2460
ataccgcaca gatgcgtaag gagaaaatac cgcatcaggc gccattcgcc attcaggctg    2520
cgcaactgtt gggaagggcg atcggtgcgg gcctcttcgc tattacgcca gctggcgaaa    2580
gggggatgtg ctgcaaggcg attaagttgg gtaacgccag ggttttccca gtcacgacgt    2640
tgtaaaacga cggccagtga attcgagctc ggtacccggg gatcctctag acgtacgttg    2700
aaacatccct gaagtgtctc attttatttt atttattctt tgctgataaa aaaataaaat    2760
aaaagaagct aagcacacgg tcaaccattg ctctactgct aaaagggtta tgtgtagtgt    2820
tttactgcat aaattatgca gcaaacaaga caactcaaat taaaaatttt cctttgcttg    2880
ttttttttgtt gtctctgact tgactttctt gtggaagttg gttgtataag gattgggaca    2940
ccattgtcct tcttaattta attttattct ttgctgataa aaaaaaaaat ttcatatagt    3000
gttaaataat aaatttgttaa ataaccaaaa agtcaaatat gtttactctc gtttaaataa    3060
ttgagattcg tccagcaagg ctaaacgatt gtatagattt atgacaatat ttactttttt    3120
atagataaat gttatattat aataaattta tatacatata ttatatgtta tttattatta    3180
ttttaaatcc ttcaatattt tatcaaacca actcataatt ttttttttat ctgtaagaag    3240
caataaaatt aaatagaccc actttaagga tgatccaacc tttatacaga gtaagagagt    3300
tcaaatagta cccctttcata tacatatcaa ctaaaatatt agaaatatca tggatcaaac    3360
cttataaaga cattaaataa gtggataagt ataatatata aatgggtagt atataatata    3420
taaatggata caaacttctc tctttataat tgttatgtct ccttaacatc ctaatataat    3480
acataagtgg gtaatatata atatataaat ggagacaaac ttcttccatt ataattgtta    3540
tgtcttctta acacttatgt ctcgttcaca atgctaaggt tagaattgtt tagaaagtct    3600
tatagtacac atttgttttt gtactatttg aagcattcca taagccgtca cgattcagat    3660
gatttataat aataagagga aatttatcat agaacaataa ggtgcataga tagagtgtta    3720
atatatcata acatcctttg tttattcata gaagaagtga gatggagctc agttattata    3780
ctgttacatg gtcggataca atattccatg ctctccatga gctcttacac ctacatgcat    3840
tttagttcat acttgcggcc gcagtatatc ttaaattctt taatacggtg tactaggata    3900
ttgaactggt tcttgatgat gaaaacctgg gccgagattg cagctattta tagtcatagg    3960
```

-continued

| | |
|---|---|
| tcttgttaac atgcatggac atttggccac ggggtggcat gcagtttgac gggtgttgaa | 4020 |
| ataaacaaaa atgaggtggc ggaagagaat acgagtttga ggttgggtta gaaacaacaa | 4080 |
| atgtgagggc tcatgatggg ttgagttggt gaatgttttg ggctgctcga ttgacacctt | 4140 |
| tgtgagtacg tgttgttgtg catggctttt ggggtccagt ttttttttct tgacgcggcg | 4200 |
| atcctgatca gctagtggat aagtgatgtc cactgtgtgt gattgcgttt ttgtttgaat | 4260 |
| tttatgaact tagacattgc tatgcaaagg atactctcat tgtgttttgt cttcttttgt | 4320 |
| tccttggctt tttcttatga tccaagagac tagtcagtgt tgtggcattc gagactacca | 4380 |
| agattaatta tgatgggga aggataagta actgattagt acggactgtt accaaattaa | 4440 |
| ttaataagcg gcaaatgaag ggcatggatc ggccggcct | 4479 |

<210> SEQ ID NO 31
<211> LENGTH: 5010
<212> TYPE: DNA
<213> ORGANISM: Artificial
<220> FEATURE:
<223> OTHER INFORMATION: Plasmid pKR63
<220> FEATURE:
<221> NAME/KEY: misc_feature
<222> LOCATION: (3863)..(3863)
<223> OTHER INFORMATION: n is a, c, g, or t

<400> SEQUENCE: 31

| | |
|---|---|
| ggcatgcaag cttggcgtaa tcatggtcat agctgtttcc tgtgtgaaat tgttatccgc | 60 |
| tcacaattcc acacaacata cgagccggaa gcataaagtg taaagcctgg ggtgcctaat | 120 |
| gagtgagcta actcacatta attgcgttgc gctcactgcc cgctttccag tcgggaaacc | 180 |
| tgtcgtgcca gctgcattaa tgaatcggcc aacgcgcggg gagaggcggt ttgcgtattg | 240 |
| ggcgctcttc cgcttcctcg ctcactgact cgctgcgctc ggtcgttcgg ctgcggcgag | 300 |
| cggtatcagc tcactcaaag gcggtaatac ggttatccac agaatcaggg gataacgcag | 360 |
| gaaagaacat gtgagcaaaa ggccagcaaa aggccaggaa ccgtaaaaag gccgcgttgc | 420 |
| tggcgttttt ccataggctc cgcccccctg acgagcatca caaaaatcga cgctcaagtc | 480 |
| agaggtggcg aaacccgaca ggactataaa gataccaggc gtttccccct ggaagctccc | 540 |
| tcgtgcgctc tcctgttccg accctgccgc ttaccggata cctgtccgcc tttctccctt | 600 |
| cgggaagcgt ggcgctttct catagctcac gctgtaggta tctcagttcg gtgtaggtcg | 660 |
| ttcgctccaa gctgggctgt gtgcacgaac cccccgttca gcccgaccgc tgcgccttat | 720 |
| ccggtaacta tcgtcttgag tccaacccgg taagacacga cttatcgcca ctggcagcag | 780 |
| ccactggtaa caggattagc agagcgaggt atgtaggcgg tgctacagag ttcttgaagt | 840 |
| ggtggcctaa ctacggctac actagaagga cagtatttgg tatctgcgct ctgctgaagc | 900 |
| cagttacctt cggaaaaaga gttggtagct cttgatccgg caaacaaacc accgctggta | 960 |
| gcggtggttt ttttgtttgc aagcagcaga ttacgcgcag aaaaaaagga tctcaagaag | 1020 |
| atcctttgat cttttctacg ggtctgacg ctcagtggaa cgaaaactca cgttaaggga | 1080 |
| ttttggtcat gagattatca aaaaggatct cacctagat ccttttaaat taaaaatgaa | 1140 |
| gttttaaatc aatctaaagt atatatgagt aaacttggtc tgacagttac caatgcttaa | 1200 |
| tcagtgaggc acctatctca gcgatctgtc tatttcgttc atccatagtt gcctgactcc | 1260 |
| ccgtcgtgta gataactacg atacgggagg gcttaccatc tggccccagt gctgcaatga | 1320 |
| taccgcgaga cccacgctca ccggctccag atttatcagc aataaaccag ccagccgaa | 1380 |
| gggccgagcg cagaagtggt cctgcaactt tatccgcctc catccagtct attaattgtt | 1440 |

```
gccgggaagc tagagtaagt agttcgccag ttaatagttt gcgcaacgtt gttgccattg    1500
ctacaggcat cgtggtgtca cgctcgtcgt ttggtatggc ttcattcagc tccggttccc    1560
aacgatcaag gcgagttaca tgatccccca tgttgtgcaa aaaagcggtt agctccttcg    1620
gtcctccgat cgttgtcaga agtaagttgg ccgcagtgtt atcactcatg gttatggcag    1680
cactgcataa ttctcttact gtcatgccat ccgtaagatg cttttctgtg actggtgagt    1740
actcaaccaa gtcattctga gaatagtgta tgcggcgacc gagttgctct tgcccggcgt    1800
caatacggga taataccgcg ccacatagca gaactttaaa agtgctcatc attggaaaac    1860
gttcttcggg gcgaaaactc tcaaggatct taccgctgtt gagatccagt tcgatgtaac    1920
ccactcgtgc acccaactga tcttcagcat cttttacttt caccagcgtt tctgggtgag    1980
caaaaacagg aaggcaaaat gccgcaaaaa agggaataag ggcgacacgg aaatgttgaa    2040
tactcatact cttccttttt caatattatt gaagcattta tcagggttat tgtctcatga    2100
gcggatacat atttgaatgt atttagaaaa ataaacaaat aggggttccg cgcacatttc    2160
cccgaaaagt gccacctgac gtctaagaaa ccattattat catgacatta acctataaaa    2220
ataggcgtat cacgaggccc tttcgtctcg cgcgtttcgg tgatgacggt gaaaacctct    2280
gacacatgca gctcccggag acggtcacag cttgtctgta agcggatgcc gggagcagac    2340
aagcccgtca gggcgcgtca gcgggtgttg gcgggtgtcg ggctggctt aactatgcgg    2400 catcagagca gattgtactg agagtgcacc atatgcggtg tgaaataccg cacagatgcg    2460
taaggagaaa ataccgcatc aggcgccatt cgccattcag gctgcgcaac tgttgggaag    2520
ggcgatcggt gcgggcctct tcgctattac gccagctggc gaaaggggga tgtgctgcaa    2580
ggcgattaag ttgggtaacg ccagggtttt cccagtcacg acgttgtaaa acgacggcca    2640
gtgaattcga gctcggtacc cggggatcct ctagagtcga cctgcaggtc ctcgaagaga    2700
agggttaata acacattttt taacattttt aacacaaatt ttagttattt aaaaatttat    2760
taaaaatttt aaaataagaa gaggaactct ttaaataaat ctaacttaca aaatttatga    2820
tttttaataa gttttcacca ataaaaaatg tcataaaaat atgttaaaaa gtatattatc    2880
aatattctct ttatgataaa taaaagaaa aaaaaaataa aagttaagtg aaaatgagat    2940
tgaagtgact ttaggtgtgt ataaatatat caaccccgcc aacaatttat ttaatccaaa    3000
tatattgaag tatattattc catagccttt atttatttat atatttatta tataaaagct    3060
ttatttgttc taggttgttc atgaaatatt ttttggttt tatctccgtt gtaagaaaat    3120
catgtgcttt gtgtcgccac tcactattgc agcttttca tgcattggtc agattgacgg    3180
ttgattgtat ttttgttttt tatggttttg tgttatgact taagtcttca tctctttatc    3240
tcttcatcag gtttgatggt tacctaatat ggtccatggg tacatgcatg gttaaattag    3300
gtggccaact tgttgtgaa cgatagaatt ttttttatat taagtaaact ttttttatat    3360
tatgaaataa taataaaaaa atatttttat cattattaac aaaatcatat tagttaattt    3420
gttaactcta taataaaaga aatactgtaa cattcacatt acatggtaac atcttttccac    3480 cctttcattt gttttttgtt tgatgacttt ttttcttgtt taaatttatt tcccttctttt    3540 taaatttgga atacattatc atcatatata aactaaaata ctaaaaacag gattacacaa    3600
atgataaata ataacacaaa tatttataaa tctagctgca atatatttaa actagctata    3660
tcgatattgt aaaataaaac tagctgcatt gatactgata aaaaaatatc atgtgctttc    3720
tggactgatg atgcagtata cttttgacat tgcctttatt ttatttttca gaaaagcttt    3780
```

```
cttagttctg ggttcttcat tatttgtttc ccatctccat tgtgaattga atcatttgct    3840
tcgtgtcaca aatacaattt agntaggtac atgcattggt cagattcacg gtttattatg    3900
tcatgactta agttcatggt agtacattac ctgccacgca tgcattatat tggttagatt    3960
tgataggcaa atttggttgt caacaatata aatataaata atgttttat attacgaaat    4020 aacagtgatc aaaacaaaca gttttatctt tattaacaag attttgtttt tgtttgatga    4080
cgttttttaa tgtttacgct ttccccttc ttttgaattt agaacacttt atcatcataa    4140
aatcaaatac taaaaaaatt acatatttca taaataataa cacaaatatt tttaaaaaat    4200
ctgaaataat aatgaacaat attacatatt atcacgaaaa ttcattaata aaaatattat    4260
ataaataaaa tgtaatagta gttatatgta ggaaaaaagt actgcacgca taatatatac    4320
aaaaagatta aaatgaacta ttataaataa taacactaaa ttaatggtga atcatatcaa    4380
aataatgaaa aagtaaataa aatttgtaat taacttctat atgtattaca cacacaaata    4440
ataaataata gtaaaaaaaa ttatgataaa tatttaccat ctcataagat atttaaaata    4500
atgataaaaa tatagattat tttttatgca actagctagc caaaaagaga acacgggtat    4560
atataaaaag agtaccttta aattctactg tacttccttt attcctgacg ttttatatc    4620 aagtggacat acgtgaagat tttaattatc agtctaaata tttcattagc acttaatact    4680
tttctgtttt attcctatcc tataagtagt cccgattctc ccaacattgc ttattcacac    4740
aactaactaa gaaagtcttc catagccccc caagcggccg cgacacaagt gtgagagtac    4800
taaataaatg cttggttgt acgaaatcat tacactaaat aaaataatca agcttatat    4860 atgccttccg ctaaggccga atgcaaagaa attggttctt tctcgttatc ttttgccact    4920
tttactagta cgtattaatt actacttaat catctttgtt tacggctcat tatatccggc    4980
cggcctaaag ggcggatccc ccgggctgca                                     5010
```

<210> SEQ ID NO 32
<211> LENGTH: 5414
<212> TYPE: DNA
<213> ORGANISM: Artificial
<220> FEATURE:
<223> OTHER INFORMATION: Plasmid pDS1
<220> FEATURE:
<221> NAME/KEY: misc_feature
<222> LOCATION: (1220)..(1220)
<223> OTHER INFORMATION: n is a, c, g, or t

<400> SEQUENCE: 32

```
aattcgagct cggtacccgg ggatcctcta gagtcgacct gcaggtcctc gaagagaagg     60
gttaataaca cattttttaa catttttaac acaaatttta gttatttaaa aatttattaa    120
aaaatttaaa ataagaagag gaactcttta aataaatcta acttacaaaa tttatgattt    180
ttaataagtt ttcaccaata aaaaatgtca taaaaatatg ttaaaaagta tattatcaat    240
attctcttta tgataaataa aaagaaaaaa aaaataaaag ttaagtgaaa atgagattga    300
agtgacttta ggtgtgtata aatatatcaa ccccgccaac aatttattta atccaaatat    360
attgaagtat attattccat agcctttatt tatttatata tttattatat aaaagcttta    420
tttgttctag gttgttcatg aaatattttt ttggttttat ctccgttgta agaaaatcat    480
gtgctttgtg tcgccactca ctattgcagc ttttcatgc attggtcaga ttgacggttg    540
attgtatttt tgtttttat ggttttgtgt tatgacttaa gtcttcatct ctttatctct    600
tcatcaggtt tgatggttac ctaatatggt ccatgggtac atgcatggtt aaattaggtg    660
gccaactttg ttgtgaacga tagaattttt tttatattaa gtaaactatt tttatattat    720
```

```
gaaataataa taaaaaaaat attttatcat tattaacaaa atcatattag ttaatttgtt    780
aactctataa taaaagaaat actgtaacat tcacattaca tggtaacatc tttccaccct    840
ttcatttgtt ttttgtttga tgactttttt tcttgtttaa atttatttcc cttcttttaa    900
atttggaata cattatcatc atatataaac taaaatacta aaaacaggat tacacaaatg    960
ataaataata acacaaatat ttataaatct agctgcaata tatttaaact agctatatcg   1020
atattgtaaa ataaaactag ctgcattgat actgataaaa aaatatcatg tgctttctgg   1080
actgatgatg cagtatactt ttgacattgc ctttatttta tttttcagaa aagctttctt   1140
agttctgggt tcttcattat ttgtttccca tctccattgt gaattgaatc atttgcttcg   1200
tgtcacaaat acaatttagn taggtacatg cattggtcag attcacggtt tattatgtca   1260
tgacttaagt tcatggtagt acattacctg ccacgcatgc attatattgg ttagatttga   1320
taggcaaatt tggttgtcaa caatataaat ataaataatg tttttatatt acgaaataac   1380
agtgatcaaa acaaacagtt ttatctttat taacaagatt ttgttttgt ttgatgacgt    1440
tttttaatgt ttacgctttc ccccttcttt tgaatttaga acactttatc atcataaaat   1500
caaatactaa aaaattaca tatttcataa ataataacac aaatattttt aaaaaatctg    1560
aaataataat gaacaatatt acatattatc acgaaaattc attaataaaa atattatata   1620
aataaaatgt aatagtagtt atatgtagga aaaaagtact gcacgcataa tatatacaaa   1680
aagattaaaa tgaactatta taaataataa cactaaatta atggtgaatc atatcaaaat   1740
aatgaaaaag taaataaaat ttgtaattaa cttctatatg tattacacac acaaataata   1800
aataatagta aaaaaaatta tgataaatat ttaccatctc ataagatatt taaaataatg   1860
ataaaaatat agattatttt ttatgcaact agctagccaa aaagagaaca cgggtatata   1920
taaaagagt acctttaaat tctactgtac ttcctttatt cctgacgttt ttatatcaag    1980
tggacatacg tgaagatttt aattatcagt ctaaatattt cattagcact taatactttt   2040
ctgttttatt cctatcctat aagtagtccc gattctccca acattgctta ttcacacaac   2100
taactaagaa agtcttccat agccccccaa gcggccgcag tatatcttaa attctttaat   2160
acggtgtact aggatattga actggttctt gatgatgaaa acctgggccg agattgcagc   2220
tatttatagt cataggtctt gttaacatgc atggacattt ggccacgggg tggcatgcag   2280
tttgacgggt gttgaaataa acaaaaatga ggtggcggaa gagaatacga gtttgaggtt   2340
gggttagaaa caacaaatgt gagggctcat gatgggttga gttggtgaat gttttgggct   2400
gctcgattga caccttttgtg agtacgtgtt gttgtgcatg gcttttgggg tccagttttt   2460
ttttcttgac gcggcgatcc tgatcagcta gtggataagt gatgtccact gtgtgtgatt   2520
gcgttttgt ttgaatttta tgaacttaga cattgctatg caaggatac tctcattgtg     2580
ttttgtcttc ttttgttcct tggctttttc ttatgatcca agagactagt cagtgttgtg   2640
gcattcgaga ctaccaagat taattatgat gggggaagga taagtaactg attagtacgg   2700
actgttacca aattaattaa taagcggcaa atgaagggca tggatcggcc ggcctctaga   2760
gtcgacctgc aggcatgcaa gcttggcgta atcatggtca tagctgtttc ctgtgtgaaa   2820
ttgttatccg ctcacaattc cacacaacat acgagccgga agcataaagt gtaaagcctg   2880
gggtgcctaa tgagtgagct aactcacatt aattgcgttg cgctcactgc ccgctttcca   2940
gtcgggaaac ctgtcgtgcc agctgcatta atgaatcggc caacgcgcgg ggagaggcgg   3000
tttgcgtatt gggcgctctt ccgcttcctc gctcactgac tcgctgcgct cggtcgttcg   3060
```

```
gctgcggcga gcggtatcag ctcactcaaa ggcggtaata cggttatcca cagaatcagg   3120
ggataacgca ggaaagaaca tgtgagcaaa aggccagcaa aaggccagga accgtaaaaa   3180
ggccgcgttg ctggcgtttt tccataggct ccgcccccct gacgagcatc acaaaaatcg   3240
acgctcaagt cagaggtggc gaaacccgac aggactataa agataccagg cgtttccccc   3300
tggaagctcc ctcgtgcgct ctcctgttcc gaccctgccg cttaccggat acctgtccgc   3360
ctttctccct tcgggaagcg tggcgctttc tcatagctca cgctgtaggt atctcagttc   3420
ggtgtaggtc gttcgctcca agctgggctg tgtgcacgaa ccccccgttc agcccgaccg   3480
ctgcgcctta tccggtaact atcgtcttga gtccaacccg gtaagacacg acttatcgcc   3540
actggcagca gccactggta acaggattag cagagcgagg tatgtaggcg gtgctacaga   3600
gttcttgaag tggtggccta actacggcta cactagaagg acagtatttg gtatctgcgc   3660
tctgctgaag ccagttacct tcggaaaaag agttggtagc tcttgatccg gcaaacaaac   3720
caccgctggt agcggtggtt tttttgtttg caagcagcag attacgcgca gaaaaaaagg   3780
atctcaagaa gatcctttga tcttttctac ggggtctgac gctcagtgga acgaaaactc   3840
acgttaaggg attttggtca tgagattatc aaaaaggatc ttcacctaga tccttttaaa   3900
ttaaaaatga agttttaaat caatctaaag tatatatgag taaacttggt ctgacagtta   3960
ccaatgctta atcagtgagg cacctatctc agcgatctgt ctatttcgtt catccatagt   4020
tgcctgactc cccgtcgtgt agataactac gatacgggag ggcttaccat ctggccccag   4080
tgctgcaatg ataccgcgag acccacgctc accggctcca gatttatcag caataaacca   4140
gccagccgga agggccgagc gcagaagtgg tcctgcaact ttatccgcct ccatccagtc   4200
tattaattgt tgccgggaag ctagagtaag tagttcgcca gttaatagtt tgcgcaacgt   4260
tgttgccatt gctacaggca tcgtggtgtc acgctcgtcg tttggtatgg cttcattcag   4320
ctccggttcc caacgatcaa ggcgagttac atgatccccc atgttgtgca aaaaagcggt   4380
tagctccttc ggtcctccga tcgttgtcag aagtaagttg gccgcagtgt tatcactcat   4440
ggttatggca gcactgcata attctcttac tgtcatgcca tccgtaagat gcttttctgt   4500
gactggtgag tactcaacca agtcattctg agaatagtgt atgcggcgac cgagttgctc   4560
ttgcccggcg tcaatacggg ataataccgc gccacatagc agaactttaa aagtgctcat   4620
cattggaaaa cgttcttcgg ggcgaaaact ctcaaggatc ttaccgctgt tgagatccag   4680
ttcgatgtaa cccactcgtg cacccaactg atcttcagca tcttttactt tcaccagcgt   4740
ttctgggtga gcaaaaacag gaaggcaaaa tgccgcaaaa aagggaataa gggcgacacg   4800
gaaatgttga atactcatac tcttcctttt tcaatattat tgaagcattt atcagggtta   4860
ttgtctcatg agcggataca tatttgaatg tatttagaaa aataaacaaa tagggggttcc   4920 gcgcacattt ccccgaaaag tgccacctga cgtctaagaa accattatta tcatgacatt   4980
aacctataaa aataggcgta tcacgaggcc ctttcgtctc gcgcgtttcg gtgatgacgg   5040
tgaaaacctc tgacacatgc agctcccgga gacggtcaca gcttgtctgt aagcggatgc   5100
cgggagcaga caagcccgtc agggcgcgtc agcgggtgtt ggcgggtgtc ggggctggct   5160
taactatgcg gcatcagagc agattgtact gagagtgcac catatgcggt gtgaaatacc   5220
gcacagatgc gtaaggagaa aataccgcat caggcgccat tcgccattca ggctgcgcaa   5280
ctgttgggaa gggcgatcgg tgcgggcctc ttcgctatta cgccagctgg cgaaaggggg   5340
atgtgctgca aggcgattaa gttgggtaac gccagggttt tcccagtcac gacgttgtaa   5400
aacgacggcc agtg                                                     5414
```

<210> SEQ ID NO 33
<211> LENGTH: 7085
<212> TYPE: DNA
<213> ORGANISM: Artificial
<220> FEATURE:
<223> OTHER INFORMATION: Plasmid pKR72

<400> SEQUENCE: 33

| | | | | | |
|---|---|---|---|---|---|
| gtacggatcc | gtcgacggcg | cgcccgatca | tccggatata | gttcctcctt | tcagcaaaaa | 60 |
| acccctcaag | acccgtttag | aggccccaag | gggttatgct | agttattgct | cagcggtggc | 120 |
| agcagccaac | tcagcttcct | ttcgggcttt | gttagcagcc | ggatcgatcc | aagctgtacc | 180 |
| tcactattcc | tttgccctcg | gacgagtgct | ggggcgtcgg | tttccactat | cggcgagtac | 240 |
| ttctacacag | ccatcggtcc | agacggccgc | gcttctgcgg | gcgatttgtg | tacgcccgac | 300 |
| agtcccggct | ccggatcgga | cgattgcgtc | gcatcgaccc | tgcgcccaag | ctgcatcatc | 360 |
| gaaattgccg | tcaaccaagc | tctgatagag | ttggtcaaga | ccaatgcgga | gcatatacgc | 420 |
| ccggagccgc | ggcgatcctg | caagctccgg | atgcctccgc | tcgaagtagc | gcgtctgctg | 480 |
| ctccatacaa | gccaaccacg | gcctccagaa | gaagatgttg | gcgacctcgt | attgggaatc | 540 |
| cccgaacatc | gcctcgctcc | agtcaatgac | cgctgttatg | cggccattgt | ccgtcaggac | 600 |
| attgttggag | ccgaaatccg | cgtgcacgag | gtgccggact | tcggggcagt | cctcggccca | 660 |
| aagcatcagc | tcatcgagag | cctgcgcgac | ggacgcactg | acggtgtcgt | ccatcacagt | 720 |
| ttgccagtga | tacacatggg | gatcagcaat | cgcgcatatg | aaatcacgcc | atgtagtgta | 780 |
| ttgaccgatt | ccttgcggtc | cgaatgggcc | gaacccgctc | gtctggctaa | gatcggccgc | 840 |
| agcgatcgca | tccatagcct | ccgcgaccgg | ctgcagaaca | gcgggcagtt | cggtttcagg | 900 |
| caggtcttgc | aacgtgacac | cctgtgcacg | cgggagatg | caataggtca | ggctctcgct | 960 |
| gaattccccca | atgtcaagca | cttccggaat | cgggagcgcg | gccgatgcaa | agtgccgata | 1020 |
| aacataacga | tctttgtaga | aaccatcggc | gcagctattt | acccgcagga | catatccacg | 1080 |
| ccctcctaca | tcgaagctga | aagcacgaga | ttcttcgccc | tccgagagct | gcatcaggtc | 1140 |
| ggagacgctg | tcgaactttt | cgatcagaaa | cttctcgaca | gacgtcgcgg | tgagttcagg | 1200 |
| cttttccatg | gtatatctc | cttcttaaag | ttaaacaaaa | ttatttctag | agggaaaccg | 1260 |
| ttgtggtctc | cctatagtga | gtcgtattaa | tttcgcggga | tcgagatcga | tccaattcca | 1320 |
| atcccacaaa | aatctgagct | taacagcaca | gttgctcctc | tcagagcaga | atcgggtatt | 1380 |
| caacacccct | atatcaacta | ctacgttgtg | tataacggtc | cacatgccgg | tatatacgat | 1440 |
| gactggggtt | gtacaaaggc | ggcaacaaac | ggcgttcccg | gagttgcaca | caagaaattt | 1500 |
| gccactatta | cagaggcaag | agcagcagct | gacgcgtaca | caacaagtca | gcaaacagac | 1560 |
| aggttgaact | tcatcccaa | aggagaagct | caactcaagc | ccaagagctt | gctaaggcc | 1620 |
| ctaacaagcc | caccaaagca | aaaagcccac | tggctcacgc | taggaaccaa | aaggcccagc | 1680 |
| agtgatccag | ccccaaaaga | gatctccttt | gccccggaga | ttacaatgga | cgatttcctc | 1740 |
| tatctttacg | atctaggaag | gaagttcgaa | ggtgaaggtg | acgacactat | gttcaccact | 1800 |
| gataatgaga | aggttagcct | cttcaatttc | agaaagaatg | ctgacccaca | gatggttaga | 1860 |
| gaggcctacg | cagcaggtct | catcaagacg | atctacccga | gtaacaatct | ccaggagatc | 1920 |
| aaataccttc | ccaagaaggt | taagatgca | gtcaaaagat | tcaggactaa | ttgcatcaag | 1980 |
| aacacagaga | aagacatatt | tctcaagatc | agaagtacta | ttccagtatg | gacgattcaa | 2040 |

```
ggcttgcttc ataaaccaag gcaagtaata gagattggag tctctaaaaa ggtagttcct    2100
actgaatcta aggccatgca tggagtctaa gattcaaatc gaggatctaa cagaactcgc    2160
cgtgaagact ggcgaacagt tcatacagag tcttttacga ctcaatgaca agaagaaaat    2220
cttcgtcaac atggtggagc acgacactct ggtctactcc aaaaatgtca agatacagt    2280
ctcagaagac caaagggcta ttgagacttt tcaacaaagg ataatttcgg gaaacctcct    2340
cggattccat tgcccagcta tctgtcactt catcgaaagg acagtagaaa aggaaggtgg    2400
ctcctacaaa tgccatcatt gcgataaagg aaaggctatc attcaagatg cctctgccga    2460
cagtggtccc aaagatggac ccccacccac gaggagcatc gtggaaaaag aagacgttcc    2520
aaccacgtct tcaaagcaag tggattgatg tgacatctcc actgacgtaa gggatgacgc    2580
acaatcccac tatccttcgc aagacccttc ctctatataa ggaagttcat ttcatttgga    2640
gaggacacgc tcgagctcat ttctctatta cttcagccat aacaaaagaa ctcttttctc    2700
ttcttattaa accatgaaaa agcctgaact caccgcgacg tctgtcgaga gtttctgat     2760
cgaaaagttc gacagcgtct ccgacctgat gcagctctcg gagggcgaag aatctcgtgc    2820
tttcagcttc gatgtaggag ggcgtggata tgtcctgcgg gtaaatagct gcgccgatgg    2880
tttctacaaa gatcgttatg tttatcggca ctttgcatcg gccgcgctcc cgattccgga    2940
agtgcttgac attggggaat tcagcgagag cctgacctat tgcatctccc gccgtgcaca    3000
gggtgtcacg ttgcaagacc tgcctgaaac cgaactgccc gctgttctgc agccggtcgc    3060
ggaggccatg gatgcgatcg ctgcggccga tcttagccag acgagcgggt tcggcccatt    3120
cggaccgcaa ggaatcggtc aatacactac atggcgtgat ttcatatgcg cgattgctga    3180
tccccatgtg tatcactggc aaactgtgat ggacgcacac cgtcagtgcgt ccgtcgcgca    3240
ggctctcgat gagctgatgc tttgggccga ggactgcccc gaagtccggc acctcgtgca    3300
cgcggatttc ggctccaaca atgtcctgac ggacaatggc cgcataacag cggtcattga    3360
ctggagcgag gcgatgttcg gggattccca atacgaggtc gccaacatct tcttctggag    3420
gccgtggttg gcttgtatgg agcagcagac gcgctacttc gagcggaggc atccggagct    3480
tgcaggatcg ccgcggctcc gggcgtatat gctccgcatt ggtcttgacc aactctatca    3540
gagcttggtt gacggcaatt tcgatgatgc agcttgggcg cagggtcgat gcgacgcaat    3600
cgtccgatcc ggagccggga ctgtcgggcg tacacaaatc gcccgcagaa gcgcggccgt    3660
ctggaccgat ggctgtgtag aagtactcgc cgatagtgga aaccgacgcc ccagcactcg    3720
tccgagggca aggaatagt gaggtaccta agaaggagt gcgtcgaagc agatcgttca    3780
aacatttggc aataaagttt cttaagattg aatcctgttg ccggtcttgc gatgattatc    3840
atataatttc tgttgaatta cgttaagcat gtaataatta acatgtaatg catgacgtta    3900
tttatgagat gggtttttat gattagagtc ccgcaattat acatttaata cgcgatagaa    3960
aacaaaatat agcgcgcaaa ctaggataaa ttatcgcgcg cggtgtcatc tatgttacta    4020
gatcgatgtc gaatcgatca acctgcatta atgaatcggc caacgcgcgg ggagaggcgg    4080
tttgcgtatt gggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
```

```
ctttctccct tcgggaagcg tggcgctttc tcaatgctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttgtttg caagcagcag attacgcgca gaaaaaaagg    4860
atctcaagaa gatcctttga tcttttctac ggggtctgac gctcagtgga acgaaaactc    4920
acgttaaggg attttggtca tgacattaac ctataaaaat aggcgtatca cgaggccctt    4980
tcgtctcgcg cgtttcggtg atgacggtga aaacctctga cacatgcagc tcccggagac    5040
ggtcacagct tgtctgtaag cggatgccgg gagcagacaa gcccgtcagg gcgcgtcagc    5100
gggtgttggc gggtgtcggg gctggcttaa ctatgcggca tcagagcaga ttgtactgag    5160
agtgcaccat atggacatat tgtcgttaga acgcggctac aattaataca taaccttatg    5220
tatcatacac atacgattta ggtgacacta tagaacggcg cgccaagctt gttgaaacat    5280
ccctgaagtg tctcatttta ttttatttat tctttgctga taaaaaaata aaataaaaga    5340
agctaagcac acggtcaacc attgctctac tgctaaaagg gttatgtgta gtgttttact    5400
gcataaatta tgcagcaaac aagacaactc aaattaaaaa atttcctttg cttgtttttt    5460
tgttgtctct gacttgactt tcttgtggaa gttggttgta taaggattgg gacaccattg    5520
tccttcttaa tttaatttta ttctttgctg ataaaaaaaa aaatttcata tagtgttaaa    5580
taataatttg ttaaataacc aaaaagtcaa atatgtttac tctcgtttaa ataattgaga    5640
ttcgtccagc aaggctaaac gattgtatag atttatgaca atatttactt ttttatagat    5700
aaatgttata ttataataaa tttatataca tatattatat gttatttatt attattttaa    5760
atccttcaat attttatcaa accaactcat aatttttttt ttatctgtaa gaagcaataa    5820
aattaaatag acccacttta aggatgatcc aacctttata cagagtaaga gagttcaaat    5880
agtacccttt catatacata tcaactaaaa tattagaaat atcatggatc aaaccttata    5940
aagacattaa ataagtggat aagtataata tataaatggg tagtatataa tatataaatg    6000
gatacaaact tctctctta taattgttat gtctccttaa catcctaata taatacataa    6060
gtgggtaata tataatatat aaatggagac aaacttcttc cattataatt gttatgtctt    6120
cttaacactt atgtctcgtt cacaatgcta aggttagaat tgtttagaaa gtcttatagt    6180
acacatttgt ttttgtacta tttgaagcat tccataagcc gtcacgattc agatgattta    6240
taataataag aggaaattta tcatagaaca ataaggtgca tagatagagt gttaatatat    6300
cataacatcc tttgtttatt catagaagaa gtgagatgga gctcagttat tatactgtta    6360
catggtcgga tacaatattc catgctctcc atgagctctt acacctacat gcattttagt    6420
tcatacttgc ggccgcagta tatcttaaat tctttaatac ggtgtactag gatattgaac    6480
tggttcttga tgatgaaaac ctgggccgag attgcagcta tttatagtca taggtcttgt    6540
taacatgcat ggacatttgg ccacggggtg gcatgcagtt tgacgggtgt gaaataaac    6600 aaaaatgagg tggcggaaga gaatacgagt ttgaggttgg gttagaaaca acaaatgtga    6660
gggctcatga tgggttgagt tggtgaatgt tttgggctgc tcgattgaca cctttgtgag    6720
tacgtgttgt tgtgcatggc ttttgggagtc cagtttttttt ttcttgacgc ggcgatcctg    6780
```

-continued

```
atcagctagt ggataagtga tgtccactgt gtgtgattgc gtttttgttt gaattttatg    6840
aacttagaca ttgctatgca aaggatactc tcattgtgtt ttgtcttctt ttgttccttg    6900
gcttttcctt atgatccaag agactagtca gtgttgtggc attcgagact accaagatta    6960
attatgatgg gggaaggata agtaactgat tagtacggac tgttaccaaa ttaattaata    7020
agcggcaaat gaagggcatg gatcaaaagc ttggatctcc tgcaggatct ggccggccgg    7080
atctc                                                                7085
```

<210> SEQ ID NO 34
<211> LENGTH: 5303
<212> TYPE: DNA
<213> ORGANISM: Artificial
<220> FEATURE:
<223> OTHER INFORMATION: Plasmid pDS2

<400> SEQUENCE: 34

```
agcttggatc tcctgcagga tctggccggc cggatctcgt acggatccgt cgacggcgcg     60
cccgatcatc cggatatagt tcctcctttc agcaaaaaac ccctcaagac ccgtttagag    120
gccccaaggg gttatgctag ttattgctca gcggtggcag cagccaactc agcttccttt    180
cgggctttgt tagcagccgg atcgatccaa gctgtacctc actattcctt tgccctcgga    240
cgagtgctgg ggcgtcggtt tccactatcg gcgagtactt ctacacagcc atcggtccag    300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacat tgttggagcc gaaatccgcg    660
tgcacgaggt gccggacttc ggggcagtcc tcggcccaaa gcatcagctc atcgagagcc    720
tgcgcgacgg acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga accgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact ctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca cacccctcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
```

```
tctcctttgc cccggagatt acaatggacg atttcctcta tctttacgat ctaggaagga    1800
agttcgaagg tgaaggtgac gacactatgt tcaccactga taatgagaag gttagcctct    1860
tcaatttcag aaagaatgct gacccacaga tggttagaga ggcctacgca gcaggtctca    1920
tcaagacgat ctacccgagt aacaatctcc aggagatcaa ataccttccc aagaaggtta    1980
aagatgcagt caaaagattc aggactaatt gcatcaagaa cacagagaaa gacatatttc    2040
tcaagatcag aagtactatt ccagtatgga cgattcaagg cttgcttcat aaaccaaggc    2100
aagtaataga gattggagtc tctaaaaagg tagttcctac tgaatctaag gccatgcatg    2160
gagtctaaga ttcaaatcga ggatctaaca gaactcgccg tgaagactgg cgaacagttc    2220
atacagagtc ttttacgact caatgacaag aagaaaatct tcgtcaacat ggtggagcac    2280
gacactctgg tctactccaa aaatgtcaaa gatacagtct cagaagacca aagggctatt    2340 gagactttc aacaaaggat aatttcggga aacctcctcg gattccattg cccagctatc    2400
tgtcacttca tcgaaaggac agtagaaaag gaaggtggct cctacaaatg ccatcattgc    2460
gataaaggaa aggctatcat tcaagatgcc tctgccgaca gtggtcccaa agatggaccc    2520
ccacccacga ggagcatcgt ggaaaaagaa gacgttccaa ccacgtcttc aaagcaagtg    2580
gattgatgtg acatctccac tgacgtaagg gatgacgcac aatcccacta tccttcgcaa    2640
gacccttcct ctatataagg aagttcattt catttggaga ggacacgctc gagctcattt    2700
ctctattact tcagccataa caaaagaact ctttctctt cttattaaac catgaaaaag    2760
cctgaactca ccgcgacgtc tgtcgagaag tttctgatcg aaaagttcga cagcgtctcc    2820
gacctgatgc agctctcgga gggcgaagaa tctcgtgctt tcagcttcga tgtaggaggg    2880
cgtggatatg tcctgcgggt aaatagctgc gccgatggtt tctacaaaga tcgttatgtt    2940
tatcggcact ttgcatcggc cgcgctcccg attccggaag tgcttgacat tggggaattc    3000
agcgagagcc tgacctattg catctcccgc cgtgcacagg tgtcacgtt gcaagacctg    3060 cctgaaaccg aactgcccgc tgttctgcag ccggtcgcgg aggccatgga tgcgatcgct    3120
gcggccgatc ttagccagac gagcgggttc ggcccattcg gaccgcaagg aatcggtcaa    3180
tacactacat ggcgtgattt catatgcgcg attgctgatc cccatgtgta tcactggcaa    3240
actgtgatgg acgacaccgt cagtgcgtcc gtcgcgcagg ctctcgatga gctgatgctt    3300
tgggccgagg actgccccga agtccggcac ctcgtgcacg cggatttcgg ctccaacaat    3360
gtcctgacgg acaatggccg cataacagcg gtcattgact ggagcgaggc gatgttcggg    3420
gattcccaat acgaggtcgc caacatcttc ttctggaggc cgtggttggc ttgtatggag    3480
cagcagacgc gctacttcga gcggaggcat ccggagcttg caggatcgcc gcggctccgg    3540
gcgtatatgc tccgcattgg tcttgaccaa ctctatcaga gcttggttga cggcaatttc    3600
gatgatgcag cttgggcgca gggtcgatgc gacgcaatcg tccgatccgg agccgggact    3660
gtcgggcgta cacaaatcgc ccgcagaagc gcggccgtct ggaccgatgg ctgtgtagaa    3720
gtactcgccg atagtggaaa ccgacgcccc agcactcgtc cgagggcaaa ggaatagtga    3780
ggtacctaaa gaaggagtgc gtcgaagcag atcgttcaaa catttggcaa taaagtttct    3840
taagattgaa tcctgttgcc ggtcttgcga tgattatcat ataatttctg ttgaattacg    3900
ttaagcatgt aataattaac atgtaatgca tgacgttatt tatgagatgg ttttttatga    3960
ttagagtccc gcaattatac atttaatacg cgatagaaaa caaaatatag cgcgcaaact    4020
aggataaatt atcgcgcgcg gtgtcatcta tgttactaga tcgatgtcga atcgatcaac    4080
```

-continued

```
ctgcattaat gaatcggcca acgcgcgggg agaggcggtt tgcgtattgg gcgctcttcc    4140
gcttcctcgc tcactgactc gctgcgctcg gtcgttcggc tgcggcgagc ggtatcagct    4200
cactcaaagg cggtaatacg gttatccaca gaatcagggg ataacgcagg aaagaacatg    4260
tgagcaaaag gccagcaaaa ggccaggaac cgtaaaaagg ccgcgttgct ggcgtttttc    4320
cataggctcc gcccccctga cgagcatcac aaaaatcgac gctcaagtca gaggtggcga    4380
aacccgacag gactataaag ataccaggcg tttccccctg gaagctccct cgtgcgctct    4440
cctgttccga ccctgccgct taccggatac ctgtccgcct ttctcccttc gggaagcgtg    4500
gcgctttctc aatgctcacg ctgtaggtat ctcagttcgg tgtaggtcgt tcgctccaag    4560
ctgggctgtg tgcacgaacc ccccgttcag cccgaccgct gcgccttatc cggtaactat    4620
cgtcttgagt ccaacccggt aagacacgac ttatcgccac tggcagcagc cactggtaac    4680
aggattagca gagcgaggta tgtaggcggt gctacagagt tcttgaagtg gtggcctaac    4740
tacggctaca ctagaaggac agtatttggt atctgcgctc tgctgaagcc agttaccttc    4800
ggaaaaagag ttggtagctc ttgatccggc aaacaaacca ccgctggtag cggtggtttt    4860
tttgtttgca agcagcagat tacgcgcaga aaaaaaggat ctcaagaaga tcctttgatc    4920
ttttctacgg ggtctgacgc tcagtggaac gaaaactcac gttaagggat tttggtcatg    4980
acattaacct ataaaaatag gcgtatcacg aggccctttc gtctcgcgcg tttcggtgat    5040
gacggtgaaa acctctgaca catgcagctc ccggagacgg tcacagcttg tctgtaagcg    5100
gatgccggga gcagacaagc ccgtcagggc gcgtcagcgg gtgttggcgg gtgtcggggc    5160
tggcttaact atgcggcatc agagcagatt gtactgagag tgcaccatat ggacatattg    5220
tcgttagaac gcggctacaa ttaatacata accttatgta tcatacacat acgatttagg    5280
tgacactata gaacggcgcg cca                                            5303

<210> SEQ ID NO 35
<211> LENGTH: 8031
<212> TYPE: DNA
<213> ORGANISM: Artificial
<220> FEATURE:
<223> OTHER INFORMATION: Plasmid pDS3 (orientation 2)
<220> FEATURE:
<221> NAME/KEY: misc_feature
<222> LOCATION: (1546)..(1546)
<223> OTHER INFORMATION: n is a, c, g, or t

<400> SEQUENCE: 35
tcgactctag aggccggccg atccatgccc ttcatttgcc gcttattaat taatttggta     60
acagtccgta ctaatcagtt acttatcctt cccccatcat aattaatctt ggtagtctcg    120
aatgccacaa cactgactag tctcttggat cataagaaaa agccaaggaa caaaagaaga    180
caaaacacaa tgagagtatc ctttgcatag caatgtctaa gttcataaaa ttcaaacaaa    240
aacgcaatca cacacagtgg acatcactta tccactagct gatcaggatc gccgcgtcaa    300
gaaaaaaaaa ctggaccccc aaagccatgc acaacaacac gtactcacaa aggtgtcaat    360
cgagcagccc aaaacattca ccaactcaac ccatcatgag ccctcacatt tgttgtttct    420
aacccaacct caaactcgta ttctcttccg ccacctcatt tttgtttatt tcaacacccg    480
tcaaactgca tgccaccccg tggccaaatg tccatgcatg ttaacaagac ctatgactat    540
aaatagctgc aatctcggcc caggtttttca tcatcaagaa ccagttcaat atcctagtac    600
accgtattaa agaatttaag atatactgcg gccgcttggg gggctatgga agactttctt    660
agttagttgt gtgaataagc aatgttggga gaatcgggac tacttatagg ataggaataa    720
```

```
aacagaaaag tattaagtgc taatgaaata tttagactga taattaaaat cttcacgtat      780
gtccacttga tataaaaacg tcaggaataa aggaagtaca gtagaattta aaggtactct      840
ttttatatat acccgtgttc tcttttggc tagctagttg cataaaaaat aatctatatt       900
tttatcatta ttttaaatat cttatgagat ggtaaatatt tatcataatt tttttactal     960
ttatttatta tttgtgtgtg taatacatat agaagttaat tacaaatttt atttactttt    1020
tcattatttt gatatgattc accattaatt tagtgttatt atttataata gttcatttta    1080
atcttttgt atatattatg cgtgcagtac tttttttccta catataacta ctattacatt    1140
ttatttatat aatattttta ttaatgaatt ttcgtgataa tatgtaatat tgttcattat    1200
tatttcagat tttttaaaaa tatttgtgtt attatttatg aaatatgtaa ttttttttagt   1260
atttgatttt atgatgataa agtgttctaa attcaaaaga aggggggaaag cgtaaacatt    1320
aaaaaacgtc atcaaacaaa aacaaaatct tgttaataaa gataaaactg tttgttttga    1380
tcactgttat ttcgtaatat aaaaacatta tttatattta tattgttgac aaccaaattt    1440
gcctatcaaa tctaaccaat ataatgcatg cgtggcaggt aatgtactac catgaactta    1500
agtcatgaca taataaaccg tgaatctgac caatgcatgt acctanctaa attgtatttg    1560
tgacacgaag caaatgattc aattcacaat ggagatggga aacaaataat gaagaaccca    1620
gaactaagaa agcttttctg aaaaataaaa taaaggcaat gtcaaaagta tactgcatca    1680
tcagtccaga aagcacatga tatttttta tcagtatcaa tgcagctagt tttattttac     1740
aatatcgata tagctagttt aaatatattg cagctagatt tataaatatt tgtgttatta    1800
tttatcattt gtgtaatcct gttttttagta tttttagttta tatatgatga taatgtattc  1860
caaatttaaa agaagggaaa taaatttaaa caagaaaaaa agtcatcaaa caaaaaacaa    1920
atgaaagggt ggaaagatgt taccatgtaa tgtgaatgtt acagtatttc ttttattata    1980
gagttaacaa attaactaat atgattttgt taataatgat aaaatatttt ttttattatt    2040
atttcataat ataaaaatag tttacttaat ataaaaaaaa ttctatcgtt cacaacaaag    2100
ttggccacct aatttaacca tgcatgtacc catggaccat attaggtaac catcaaacct    2160
gatgaagaga taaagagatg aagacttaag tcataacaca aaaccataaa aaacaaaaat    2220
acaatcaacc gtcaatctga ccaatgcatg aaaaagctgc aatagtgagt ggcgacacaa    2280
agcacatgat tttcttacaa cggagataaa accaaaaaaa tatttcatga caacctaga    2340
acaaataaag cttttatata ataaatatat aaataaataa aggctatgga ataatatact    2400
tcaatatatt tggattaaat aaattgttgg cggggttgat atatttatac acacctaaag    2460
tcacttcaat ctcattttca cttaactttt attttttttt tcttttattt tatcataaag    2520
agaatattga taatatactt tttaacatat ttttatgaca tttttttattg gtgaaaactt   2580
attaaaaatc ataaattttg taagttagat ttatttaaag agttcctctt cttattttaa    2640
attttttaat aaattttaa ataactaaaa tttgtgttaa aaatgttaaa aaatgtgtta     2700
ttaacccttc tcttcgagga cctgcaggtc gacggcgcgc ccgatcatcc ggatatagtt    2760
cctcctttca gcaaaaaacc cctcaagacc cgtttagagg ccccaagggg ttatgctagt    2820
tattgctcag cggtggcagc agccaactca gcttcctttc gggctttgtt agcagcggga    2880
tcgatccaag ctgtacctca ctattccttt gccctcggac gagtgctggg gcgtcggttt    2940
ccactatcgg cgagtacttc tacacagcca tcggtccaga cggccgcgct tctgcgggcg    3000
atttgtgtac gcccgacagt cccggctccg gatcggacga ttgcgtcgca tcgaccctgc    3060
```

```
gcccaagctg catcatcgaa attgccgtca accaagctct gatagagttg gtcaagacca   3120
atgcggagca tatacgcccg gagccgcggc gatcctgcaa gctccggatg cctccgctcg   3180
aagtagcgcg tctgctgctc catacaagcc aaccacggcc tccagaagaa gatgttggcg   3240
acctcgtatt gggaatcccc gaacatcgcc tcgctccagt caatgaccgc tgttatgcgg   3300
ccattgtccg tcaggacatt gttggagccg aaatccgcgt gcacgaggtg ccggacttcg   3360
gggcagtcct cggcccaaag catcagctca tcgagagcct cgcgacgga cgcactgacg   3420 gtgtcgtcca tcacagtttg ccagtgatac acatggggat cagcaatcgc gcatatgaaa   3480
tcacgccatg tagtgtattg accgattcct tgcggtccga atgggccgaa cccgctcgtc   3540
tggctaagat cggccgcagc gatcgcatcc atagcctccg cgaccggctg cagaacagcg   3600
ggcagttcgg tttcaggcag gtcttgcaac gtgacaccct gtgcacggcg ggagatgcaa   3660
taggtcaggc tctcgctgaa ttccccaatg tcaagcactt ccggaatcgg gagcgcggcc   3720
gatgcaaagt gccgataaac ataacgatct ttgtagaaac catcggcgca gctatttacc   3780
cgcaggacat atccacgccc tcctacatcg aagctgaaag cacgagattc ttcgccctcc   3840
gagagctgca tcaggtcgga gacgctgtcg aacttttcga tcagaaactt ctcgacagac   3900
gtcgcggtga gttcaggctt ttccatgggt atatctcctt cttaaagtta aacaaaatta   3960
tttctagagg gaaaccgttg tggtctccct atagtgagtc gtattaattt cgcgggatcg   4020
agatcgatcc aattccaatc ccacaaaaat ctgagcttaa cagcacagtt gctcctctca   4080
gagcagaatc gggtattcaa caccctcata tcaactacta cgttgtgtat aacggtccac   4140
atgccggtat atacgatgac tggggttgta caaaggcggc aacaaacggc gttcccggag   4200
ttgcacacaa gaaatttgcc actattacag aggcaagagc agcagctgac gcgtacacaa   4260
caagtcagca aacagacagg ttgaacttca tccccaaagg agaagctcaa ctcaagccca   4320
agagctttgc taaggcccta acaagcccac caaagcaaaa agcccactgg ctcacgctag   4380
gaaccaaaag gcccagcagt gatccagccc caaaagagat ctcctttgcc ccggagatta   4440
caatggacga tttcctctat ctttacgatc taggaaggaa gttcgaaggt gaaggtgacg   4500
acactatgtt caccactgat aatgagaagg ttagcctctt caatttcaga aagaatgctg   4560
acccacagat ggttagagag gcctacgcag caggtctcat caagacgatc tacccgagta   4620
acaatctcca ggagatcaaa taccttccca agaaggttaa agatgcagtc aaaagattca   4680
ggactaattg catcaagaac acagagaaag acatatttct caagatcaga agtactattc   4740
cagtatggac gattcaaggc ttgcttcata accaaggca agtaatagag attggagtct   4800
ctaaaaaggt agttcctact gaatctaagg ccatgcatgg agtctaagat tcaaatcgag   4860
gatctaacag aactcgccgt gaagactggc gaacagttca tacagagtct tttacgactc   4920
aatgacaaga gaaaatcttc gtcaacatg gtggagcacg acactctggt ctactccaaa   4980
aatgtcaaag atacagtctc agaagaccaa agggctattg acttttca acaaggata    5040 atttcgggaa acctcctcgg attccattgc ccagctatct gtcacttcat cgaaaggaca   5100
gtagaaaagg aaggtggctc ctacaaatgc catcattgcg ataaaggaaa ggctatcatt   5160
caagatgcct ctgccgacag tggtcccaaa gatggacccc cacccacgag gagcatcgtg   5220
gaaaaagaag acgttccaac cacgtcttca agcaagtgg attgatgtga catctccact   5280
gacgtaaggg atgacgcaca atcccactat ccttcgcaag acccttcctc tatataagga   5340
agttcatttc atttggagag gacacgctcg agctcatttc tctattactt cagccataac   5400
aaaagaactc ttttctcttc ttattaaacc atgaaaaagc ctgaactcac gcgacgtct   5460
```

```
gtcgagaagt tctgatcga aaagttcgac agcgtctccg acctgatgca gctctcggag    5520
ggcgaagaat ctcgtgcttt cagcttcgat gtaggagggc gtggatatgt cctgcgggta    5580
aatagctgcg ccgatggttt ctacaaagat cgttatgttt atcggcactt tgcatcggcc    5640
gcgctcccga ttccggaagt gcttgacatt ggggaattca gcgagagcct gacctattgc    5700
atctcccgcc gtgcacaggg tgtcacgttg caagacctgc ctgaaaccga actgcccgct    5760
gttctgcagc cggtcgcgga ggccatggat gcgatcgctg cggccgatct tagccagacg    5820
agcgggttcg gcccattcgg accgcaagga atcggtcaat acactacatg gcgtgatttc    5880
atatgcgcga ttgctgatcc ccatgtgtat cactggcaaa ctgtgatgga cgacaccgtc    5940
agtgcgtccg tcgcgcaggc tctcgatgag ctgatgcttt gggccgagga ctgccccgaa    6000
gtccggcacc tcgtgcacgc ggatttcggc tccaacaatg tcctgacgga caatggccgc    6060
ataacagcgg tcattgactg gagcgaggcg atgttcgggg attcccaata cgaggtcgcc    6120
aacatcttct tctggaggcc gtggttggct tgtatggagc agcagacgcg ctacttcgag    6180
cggaggcatc cggagcttgc aggatcgccg cggctccggg cgtatatgct ccgcattggt    6240
cttgaccaac tctatcagag cttggttgac ggcaatttcg atgatgcagc ttgggcgcag    6300
ggtcgatgcg acgcaatcgt ccgatccgga gccgggactg tcgggcgtac acaaatcgcc    6360
cgcagaagcg cggccgtctg gaccgatggc tgtgtagaag tactcgccga tagtggaaac    6420
cgacgcccca gcactcgtcc gagggcaaag gaatagtgag gtacctaaag aaggagtgcg    6480
tcgaagcaga tcgttcaaac atttggcaat aaagtttctt aagattgaat cctgttgccg    6540
gtcttgcgat gattatcata taatttctgt tgaattacgt taagcatgta ataattaaca    6600
tgtaatgcat gacgttattt atgagatggg tttttatgat tagagtcccg caattataca    6660
tttaatacgc gatagaaaac aaaatatagc gcgcaaacta ggataaatta tcgcgcgcgg    6720
tgtcatctat gttactagat cgatgtcgaa tcgatcaacc tgcattaatg aatcggccaa    6780
cgcgcgggga gaggcggttt gcgtattggg cgctcttccg cttcctcgct cactgactcg    6840
ctgcgctcgg tcgttcggct gcggcgagcg gtatcagctc actcaaaggc ggtaatacgg    6900
ttatccacag aatcagggga taacgcagga agaacatgt gagcaaaagg ccagcaaaag    6960
gccaggaacc gtaaaaaggc cgcgttgctg gcgtttttcc ataggctccg ccccctgac    7020
gagcatcaca aaaatcgacg ctcaagtcag aggtggcgaa acccgacagg actataaaga    7080
taccaggcgt ttccccctgg aagctccctc gtgcgctctc ctgttccgac cctgccgctt    7140
accggatacc tgtccgcctt tctcccttcg ggaagcgtgg cgctttctca atgctcacgc    7200
tgtaggtatc tcagttcggt gtaggtcgtt cgctccaagc tgggctgtgt gcacgaaccc    7260
cccgttcagc ccgaccgctg cgccttatcc ggtaactatc gtcttgagtc aacccggta    7320
agacacgact tatcgccact ggcagcagcc actggtaaca ggattagcag agcgaggtat    7380
gtaggcggtg ctacagagtt cttgaagtgg tggcctaact acggctacac tagaaggaca    7440
gtatttggta tctgcgctct gctgaagcca gttaccttcg gaaaaagagt tggtagctct    7500
tgatccggca aacaaaccac cgctggtagc ggtggttttt tgtttgcaa gcagcagatt    7560
acgcgcagaa aaaaggatc tcaagaagat cctttgatct tttctacggg gtctgacgct    7620
cagtggaacg aaaactcacg ttaagggatt ttggtcatga cattaaccta taaaaatagg    7680
cgtatcacga ggccctttcg tctcgcgcgt ttcggtgatg acggtgaaaa cctctgacac    7740
atgcagctcc cggagacggt cacagcttgt ctgtaagcgg atgccgggag cagacaagcc    7800
```

```
cgtcagggcg cgtcagcggg tgttggcggg tgtcggggct ggcttaacta tgcggcatca    7860
gagcagattg tactgagagt gcaccatatg gacatattgt cgttagaacg cggctacaat    7920
taatacataa ccttatgtat catacacata cgatttaggt gacactatag aacggcgcgc    7980
caagcttgga tctcctgcag gatctggccg gccggatctc gtacggatcc g             8031

<210> SEQ ID NO 36
<211> LENGTH: 9616
<212> TYPE: DNA
<213> ORGANISM: Artificial
<220> FEATURE:
<223> OTHER INFORMATION: PLasmid SH60
<220> FEATURE:
<221> NAME/KEY: misc_feature
<222> LOCATION: (2502)..(2502)
<223> OTHER INFORMATION: n is a, c, g, or t

<400> SEQUENCE: 36
ggccgcgtca tcaactattc caagctacgt atttgggagt tgtggagta cagcaagatg     60 atatacctag acgtgatat ccaagttttt gacaacattg accacttgtt tgacttgcct    120
gataactact tctatgcggt gatggactgt ttctgtgagc aacttgggg ccacactaaa    180 caatatcaga tcggttactg ccagcagtgc ccccataagg ttcagtggcc cactcacttt    240
gggcccaaac ctcctctcta tttcaatgct ggcatgtttg tgtatgagcc caatttggct    300
acttaccgtg acctccttca aacagtccaa gtcacccagc ccacttcctt tgctgaacag    360 gatttttga acatgtactt caaggacaaa tataggccaa ttcctaatgt ctacaatctt    420
gtgctggcca tgctgtggcg tcaccctgag aacgttgagc ttgacaaagt taaagtggtt    480
cactactgtg ctgctgggtc taagccttgg aggtacactg ggaagtgact cgaggtcatc    540
aattactcca agctacgtat ttgggagttc gtggagtaca agaagacgat atacctagac    600
ggtgacatcc aagtatttgg aaacatagac cacttgtttg atctgcctga taattatttc    660
tatgcggtga tggattgttt ctgcgagaag acttggagcc acacccctca gttccagatt    720
gggtactgcc aacagtgccc tgataaggtt caatggccct ctcactttgg ttccaaacct    780
cctctatatt tcaatgctgg catgtttgtt tatgagccta atctcgacac ctaccgtgat    840
cttctccaaa ctgtccaact caccaagccc acttcttttg ctgagcagga ctttctcaac    900
atgtacttca aggacaagta caagccaata ccgaacatgc acaaccttgt gctggccatg    960
ttgtggcgtc accctgaaaa tgttgaactt gataaagttc aagtggttca ttactgtgct   1020
gctgggtcta agccttggag gttcactggg aagtaactgc aggtcatcaa ctactccaag   1080
ctccgtatat gggagtttgt ggagtacagc aagatgatat acttggacgg agacattgag   1140
gtatatgaga acatagacca cctatttgac ctacctgatg gtaacttta cgctgtgatg   1200 gattgtttct gcgagaagac atggagtcac acccctcagt acaaggtggg ttactgccag   1260
caatgcccgg agaaggtgcg gtggcccacc gaattggtc agccccttc tctttacttc   1320 aacgctggca tgttcgtgtt cgaacccaac atcgccacct atcatgacct attgaaaacg   1380
gtgcaagtca ccactccac ctcgttcgct gaacaagatt tcttgaacat gtacttcaag   1440
gacatttaca agccaatccc tttaaattac aatcttgtcc tcgccatgct gtggcgccac   1500
ccggaaaacg ttaaattaga ccaagtcaag gttgttcact attgcgcagc ggggtccaag   1560
ccatggagat atacggggaa gtagcggccg cttggggggc tatggaagac tttcttagtt   1620
agttgtgtga ataagcaatg ttgggagaat cgggactact tataggatag gaataaaaca   1680
gaaaagtatt aagtgctaat gaaatatttta gactgataat taaaatcttc acgtatgtcc   1740
```

```
acttgatata aaaacgtcag gaataaagga agtacagtag aatttaaagg tactcttttt    1800
atatataccc gtgttctctt tttggctagc tagttgcata aaaaataatc tatattttta    1860
tcattatttt aaatatctta tgagatggta aatatttatc ataatttttt ttactattat    1920
ttattatttg tgtgtgtaat acatatagaa gttaattaca aattttattt acttttttcat   1980 tattttgata tgattcacca ttaatttagt gttattattt ataatagttc attttaatct    2040
ttttgtatat attatgcgtg cagtactttt ttcctacata taactactat tacattttat    2100
ttatataata ttttttattaa tgaattttcg tgataaatatg taatattgtt cattattatt   2160
tcagattttt taaaaatatt tgtgttatta tttatgaaat atgtaattt tttagtatt     2220 gattttatga tgataaagtg ttctaaattc aaagaaggg ggaaagcgta aacattaaaa     2280
aacgtcatca aacaaaaaca aaatcttgtt aataaagata aaactgtttg ttttgatcac    2340
tgttatttcg taatataaaa acattattta tatttatatt gttgacaacc aaatttgcct    2400
atcaaatcta accaatataa tgcatgcgtg gcaggtaatg tactaccatg aacttaagtc    2460
atgacataat aaaccgtgaa tctgaccaat gcatgtacct anctaaattg tatttgtgac    2520
acgaagcaaa tgattcaatt cacaatggag atgggaaaca aataatgaag aacccagaac    2580
taagaaagct tttctgaaaa ataaaataaa ggcaatgtca aaagtatact gcatcatcag    2640
tccagaaagc acatgatatt tttttatcag tatcaatgca gctagtttta ttttacaata    2700
tcgatatagc tagtttaaat atattgcagc tagatttata atatttgtg ttattattta    2760 tcatttgtgt aatcctgttt ttagtatttt agtttatata tgatgataat gtattccaaa    2820
tttaaaagaa gggaaataaa tttaaacaag aaaaaaagtc atcaaacaaa aaacaaatga    2880
aagggtggaa agatgttacc atgtaatgtg aatgttacag tatttctttt attatagagt    2940
taacaaatta actaatatga ttttgttaat aatgataaaa tatttttttt attattattt    3000
cataatataa aaatagttta cttaatataa aaaaaattct atcgttcaca acaaagttgg    3060
ccacctaatt taaccatgca tgtacccatg gaccatatta ggtaaccatc aaacctgatg    3120
aagagataaa gagatgaaga cttaagtcat aacacaaaac cataaaaaac aaaaatacaa    3180
tcaaccgtca atctgaccaa tgcatgaaaa agctgcaata gtgagtggcg acacaaagca    3240
catgattttc ttcaacggaa gataaaaacca aaaaaatatt tcatgaacaa cctagaacaa    3300
ataaagcttt tatataataa atatataaat aaataaaggc tatggaataa tatacttcaa    3360
tatatttgga ttaaataaat tgttggcggg gttgatatat ttatacacac ctaaagtcac    3420
ttcaatctca ttttcactta acttttattt ttttttttctt tttatttatc ataaagagaa    3480
tattgataat atacttttta acatatttt atgacatttt ttattggtga aaacttatta    3540
aaaatcataa attttgtaag ttagatttat ttaaagagtt cctcttctta ttttaaattt    3600
tttaataaat ttttaaataa ctaaaatttg tgttaaaaat gttaaaaaat gtgttattaa    3660
cccttctctt cgaggacctg caggtcgacg gcgcgcccga tcatccggat atagttcctc    3720
ctttcagcaa aaaaccccctc aagacccgtt tagaggcccc aagggggttat gctagttatt    3780 gctcagcggt ggcagcagcc aactcagctt cctttcgggc tttgttagca gccggatcga    3840
tccaagctgt acctcactat tccttttgccc tcggacgagt gctggggcgt cggtttccac    3900
tatcggcgag tacttctaca cagccatcgg tccgacgggc cgcgcttctg cgggcgattt    3960
gtgtacgccc gacagtcccg gctccggatc ggacgattgc gtcgcatcga ccctgcgccc    4020
aagctgcatc atcgaaattg ccgtcaacca agctctgata gagttggtca agaccaatgc    4080
```

```
ggagcatata cgcccggagc cgcggcgatc ctgcaagctc cggatgcctc cgctcgaagt    4140
agcgcgtctg ctgctccata caagccaacc acggcctcca gaagaagatg ttggcgacct    4200
cgtattggga atccccgaac atcgcctcgc tccagtcaat gaccgctgtt atgcggccat    4260
tgtccgtcag gacattgttg gagccgaaat ccgcgtgcac gaggtgccgg acttcggggc    4320
agtcctcggc ccaaagcatc agctcatcga gagcctgcgc gacggacgca ctgacggtgt    4380
cgtccatcac agtttgccag tgatacacat ggggatcagc aatcgcgcat atgaaatcac    4440
gccatgtagt gtattgaccg attccttgcg gtccgaatgg gccgaacccg ctcgtctggc    4500
taagatcggc gcagcgatc gcatccatag cctccgcgac cggctgcaga acagcgggca    4560
gttcggtttc aggcaggtct tgcaacgtga caccctgtgc acggcgggag atgcaatagg    4620
tcaggctctc gctgaattcc ccaatgtcaa gcacttccgg aatcgggagc gcggccgatg    4680
caaagtgccg ataaacataa cgatctttgt agaaaccatc ggcgcagcta tttacccgca    4740
ggacatatcc acgccctcct acatcgaagc tgaaagcacg agattcttcg ccctccgaga    4800
gctgcatcag gtcggagacg ctgtcgaact tttcgatcag aaacttctcg acagacgtcg    4860
cggtgagttc aggcttttcc atgggtatat ctccttctta agttaaaca aaattatttc    4920 tagagggaaa ccgttgtggt ctccctatag tgagtcgtat taatttcgcg ggatcgagat    4980
cgatccaatt ccaatcccac aaaaatctga gcttaacagc acagttgctc ctctcagagc    5040
agaatcgggt attcaacacc ctcatatcaa ctactacgtt gtgtataacg gtccacatgc    5100
cggtatatac gatgactggg gttgtacaaa ggcggcaaca aacggcgttc ccggagttgc    5160
acacaagaaa tttgccacta ttacagaggc aagagcagca gctgacgcgt acacaacaag    5220
tcagcaaaca gacaggttga acttcatccc caaggagaa gctcaactca gcccaagag    5280 cttttgctaag gccctaacaa gcccaccaaa gcaaaaagcc cactggctca cgctaggaac    5340
caaaaggccc agcagtgatc cagccccaaa agagatctcc tttgccccgg agattacaat    5400
ggacgatttc ctctatcttt acgatctagg aaggaagttc gaaggtgaag gtgacgacac    5460
tatgttcacc actgataatg agaaggttag cctcttcaat ttcagaaaga atgctgaccc    5520
acagatggtt agagaggcct acgcagcagg tctcatcaag acgatctacc cgagtaacaa    5580
tctccaggag atcaaatacc ttcccaagaa ggttaaagat gcagtcaaaa gattcaggac    5640
taattgcatc aagaacacag agaaagacat atttctcaag atcagaagta ctattccagt    5700
atggacgatt caaggcttgc ttcataaacc aaggcaagta atagagattg gagtctctaa    5760
aaaggtagtt cctactgaat ctaaggccat gcatggagtc taagattcaa atcgaggatc    5820
taacagaact cgccgtgaag actggcgaac agttcataca gagtctttta cgactcaatg    5880
acaagaagaa aatcttcgtc aacatggtgg agcacgacac tctggtctac tccaaaaatg    5940
tcaaagatac agtctcagaa gaccaaaggg ctattgagac ttttcaacaa aggataattt    6000
cgggaaacct cctcggattc cattgcccag ctatctgtca cttcatcgaa aggacagtag    6060
aaaaggaagg tggctcctac aaatgccatc attgcgataa aggaaaggct atcattcaag    6120
atgcctctgc cgacagtggt cccaaagatg gacccccacc cacgaggagc atcgtggaaa    6180
aagaagacgt tccaaccacg tcttcaaagc aagtggattg atgtgacatc tccactgacg    6240
taagggatga cgcacaatcc cactatcctt cgcaagaccc ttcctctata taaggaagtt    6300
catttcattt ggagaggaca cgctcgagct catttctcta ttacttcagc cataacaaaa    6360
gaactctttt ctcttcttat taaaccatga aaaagcctga actcaccgcg acgtctgtcg    6420
agaagtttct gatcgaaaag ttcgacagcg tctccgacct gatgcagctc tcggagggcg    6480
```

```
aagaatctcg tgctttcagc ttcgatgtag gagggcgtgg atatgtcctg cgggtaaata    6540
gctgcgccga tggtttctac aaagatcgtt atgtttatcg gcactttgca tcggccgcgc    6600
tcccgattcc ggaagtgctt gacattgggg aattcagcga gagcctgacc tattgcatct    6660
cccgccgtgc acagggtgtc acgttgcaag acctgcctga aaccgaactg cccgctgttc    6720
tgcagccggt cgcggaggcc atggatgcga tcgctgcggc cgatcttagc cagacgagcg    6780
ggttcggccc attcggaccg caaggaatcg gtcaatacac tacatggcgt gatttcatat    6840
gcgcgattgc tgatccccat gtgtatcact ggcaaactgt gatggacgac accgtcagtg    6900
cgtccgtcgc gcaggctctc gatgagctga tgctttgggc cgaggactgc cccgaagtcc    6960
ggcacctcgt gcacgcggat ttcggctcca acaatgtcct gacggacaat ggccgcataa    7020
cagcggtcat tgactggagc gaggcgatgt tcggggattc ccaatacgag gtcgccaaca    7080
tcttcttctg gaggccgtgg ttggcttgta tggagcagca gacgcgctac ttcgagcgga    7140
ggcatccgga gcttgcagga tcgccgcggc tccggcgta tatgctccgc attggtcttg     7200
accaactcta tcagagcttg gttgacggca atttcgatga tgcagcttgg gcgcagggtc    7260
gatgcgacgc aatcgtccga tccggagccg ggactgtcgg gcgtacacaa atcgcccgca    7320
gaagcgcggc cgtctggacc gatggctgtg tagaagtact cgccgatagt ggaaaccgac    7380
gccccagcac tcgtccgagg gcaaaggaat agtgaggtac ctaaagaagg agtgcgtcga    7440
agcagatcgt tcaaacattt ggcaataaag tttcttaaga ttgaatcctg ttgccggtct    7500
tgcgatgatt atcatataat ttctgttgaa ttacgttaag catgtaataa ttaacatgta    7560
atgcatgacg ttatttatga gatgggtttt tatgattaga gtcccgcaat tatacattta    7620
atacgcgata gaaaacaaaa tatagcgcgc aaactaggat aaattatcgc gcgcggtgtc    7680
atctatgtta ctagatcgat gtcgaatcga tcaacctgca ttaatgaatc ggccaacgcg    7740
cggggagagg cggtttgcgt attgggcgct cttccgcttc ctcgctcact gactcgctgc    7800
gctcggtcgt tcggctgcgg cgagcggtat cagctcactc aaaggcggta atacggttat    7860
ccacagaatc aggggataac gcaggaaaga acatgtgagc aaaaggccag caaaaggcca    7920
ggaaccgtaa aaaggccgcg ttgctggcgt ttttccatag gctccgcccc cctgacgagc    7980
atcacaaaaa tcgacgctca agtcagaggt ggcgaaaccc gacaggacta taaagatacc    8040
aggcgtttcc ccctggaagc tccctcgtgc gctctcctgt tccgaccctg ccgcttaccg    8100
gatacctgtc cgcctttctc ccttcgggaa gcgtggcgct ttctcaatgc tcacgctgta    8160
ggtatctcag ttcggtgtag gtcgttcgct ccaagctggg ctgtgtgcac gaaccccccg    8220
ttcagcccga ccgctgcgcc ttatccggta actatcgtct tgagtccaac ccggtaagac    8280
acgacttatc gccactggca gcagccactg gtaacaggat tagcagagcg aggtatgtag    8340
gcggtgctac agagttcttg aagtggtggc ctaactacgg ctacactaga aggacagtat    8400
ttggtatctg cgctctgctg aagccagtta ccttcggaaa aagagttggt agctcttgat    8460
ccggcaaaca aaccaccgct ggtagcggtg gttttttgt ttgcaagcag cagattacgc      8520
gcagaaaaaa aggatctcaa gaagatcctt tgatcttttc tacggggtct gacgctcagt    8580
ggaacgaaaa ctcacgttaa gggattttgg tcatgacatt aacctataaa aataggcgta    8640
tcacgaggcc ctttcgtctc gcgcgtttcg gtgatgacgg tgaaaacctc tgacacatgc    8700
agctcccgga gacggtcaca gcttgtctgt aagcggatgc cgggagcaga caagcccgtc    8760
agggcgcgtc agcgggtgtt ggcgggtgtc ggggctggct taactatgcg gcatcagagc    8820
```

| | |
|---|---|
| agattgtact gagagtgcac catatggaca tattgtcgtt agaacgcggc tacaattaat | 8880 |
| acataacctt atgtatcata cacatacgat ttaggtgaca ctatagaacg gcgcgccaag | 8940 |
| cttggatctc ctgcaggatc tggccggccg gatctcgtac ggatccgtcg actctagagg | 9000 |
| ccggccgatc catgcccttc atttgccgct tattaattaa tttggtaaca gtccgtacta | 9060 |
| atcagttact tatccttccc ccatcataat taatcttggt agtctcgaat gccacaacac | 9120 |
| tgactagtct cttggatcat aagaaaaagc caaggaacaa aagaagacaa acacaatga | 9180 |
| gagtatcctt tgcatagcaa tgtctaagtt cataaaattc aaacaaaaac gcaatcacac | 9240 |
| acagtggaca tcacttatcc actagctgat caggatcgcc gcgtcaagaa aaaaaaactg | 9300 |
| gaccccaaaa gccatgcaca acaacacgta ctcacaaagg tgtcaatcga gcagcccaaa | 9360 |
| acattcacca actcaaccca tcatgagccc tcacatttgt tgtttctaac ccaacctcaa | 9420 |
| actcgtattc tcttccgcca cctcattttt gtttatttca acaccgtca aactgcatgc | 9480 |
| caccccgtgg ccaaatgtcc atgcatgtta acaagaccta tgactataaa tagctgcaat | 9540 |
| ctcggcccag gttttcatca tcaagaacca gttcaatatc ctagtacacc gtattaaaga | 9600 |
| atttaagata tactgc | 9616 |

<210> SEQ ID NO 37
<211> LENGTH: 1585
<212> TYPE: DNA
<213> ORGANISM: Artificial
<220> FEATURE:
<223> OTHER INFORMATION: Not1 fragment

<400> SEQUENCE: 37

| | |
|---|---|
| ggccgcgtca tcaactattc caagctacgt atttgggagt tgtggagta cagcaagatg | 60 |
| atatacctag acggtgatat ccaagttttt gacaacattg accacttgtt tgacttgcct | 120 |
| gataactact tctatgcggt gatggactgt ttctgtgagc caacttgggg ccacactaaa | 180 |
| caatatcaga tcggttactg ccagcagtgc ccccataagg ttcagtggcc cactcacttt | 240 |
| gggcccaaac ctcctctcta tttcaatgct ggcatgtttg tgtatgagcc caatttggct | 300 |
| acttaccgtg acctccttca aacagtccaa gtcacccagc ccacttcctt tgctgaacag | 360 |
| gattttttga acatgtactt caaggacaaa tataggccaa ttcctaatgt ctacaatctt | 420 |
| gtgctggcca tgctgtggcg tcaccctgag aacgttgagc ttgacaaagt taaagtggtt | 480 |
| cactactgtg ctgctgggtc taagccttgg aggtacactg ggaagtgact cgaggtcatc | 540 |
| aattactcca agctacgtat ttgggagttc gtggagtaca agaagacgat ataccctagac | 600 |
| ggtgacatcc aagtatttgg aaacatagac cacttgtttg atctgcctga taattatttc | 660 |
| tatgcggtga tggattgttt ctgcgagaag acttggagcc acacccctca gttccagatt | 720 |
| gggtactgcc aacagtgccc tgataaggtt caatggccct ctcactttgg ttccaaacct | 780 |
| cctctatatt tcaatgctgg catgtttgtt tatgagccta atctcgacac ctaccgtgat | 840 |
| cttctccaaa ctgtccaact caccaagccc acttcttttg ctgagcagga ctttctcaac | 900 |
| atgtacttca aggacaagta caagccaata ccgaacatgt acaacttgt gctggccatg | 960 |
| ttgtggcgtc accctgaaaa tgttgaactt gataaagttc aagtggttca ttactgtgct | 1020 |
| gctgggtcta agccttggag gttcactggg aagtaactgc aggtcatcaa ctactccaag | 1080 |
| ctccgtatat gggagtttgt ggagtacagc aagatgatat acttggacgg agacattgag | 1140 |
| gtatatgaga acatagacca cctatttgac ctacctgatg gtaacttta cgctgtgatg | 1200 |
| gattgtttct gcgagaagac atggagtcac accccctcagt acaaggtggg ttactgccag | 1260 |

```
caatgcccgg agaaggtgcg gtggcccacc gaattgggtc agccccttc tctttacttc    1320 aacgctggca tgttcgtgtt cgaacccaac atcgccacct atcatgacct attgaaaacg    1380
gtgcaagtca ccactcccac ctcgttcgct gaacaagatt tcttgaacat gtacttcaag    1440
gacatttaca agccaatccc tttaaattac aatcttgtcc tcgccatgct gtggcgccac    1500
ccggaaaacg ttaaattaga ccaagtcaag gttgttcact attgcgcagc ggggtccaag    1560
ccatggagat atacggggaa gtagc                                          1585
```